(12) United States Patent
Mostov et al.

(10) Patent No.: US 7,404,954 B2
(45) Date of Patent: Jul. 29, 2008

(54) METHODS OF TARGETING AGENTS TO CELLS EXPRESSING THE POLYMERIC IMMUNOGLOBULIN RECEPTOR

(75) Inventors: Keith E. Mostov, San Francisco, CA (US); Steven J. Chapin, San Diego, CA (US); Janice Richman-Eisenstat, Winnepeg (CA)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 11/038,956

(22) Filed: Jan. 19, 2005

(65) Prior Publication Data

US 2005/0201932 A1    Sep. 15, 2005

Related U.S. Application Data

(62) Division of application No. 09/818,247, filed on Mar. 26, 2001, now Pat. No. 6,855,810.

(60) Provisional application No. 60/192,197, filed on Mar. 27, 2000, provisional application No. 60/192,198, filed on Mar. 27, 2000.

(51) Int. Cl.
*A61K 39/40*    (2006.01)
*G01N 33/53*    (2006.01)

(52) U.S. Cl. ..................... 424/139.1; 435/7.1

(58) Field of Classification Search ............ None
See application file for complete search history.

(56) References Cited

U.S. PATENT DOCUMENTS

| | | | |
|---|---|---|---|
| 6,042,833 A | 3/2000 | Mostov et al. | |
| 6,046,037 A | 4/2000 | Hiatt et al. | |
| 6,340,743 B1 | 1/2002 | Mostov et al. | |
| 6,440,419 B1 | 8/2002 | Hein et al. | |

OTHER PUBLICATIONS

Cochlovius et al., Modern Drug Discovery, 2003, pp. 33-38.*
Bost et al., Immunol. Invest. 1988; pp. 577-586, vol. 17.
Bendayan J., Histochem. Cytochem. 1995, pp. 881-886, vol. 43.
Breitfeld, P.P. et al. "Expression and analysis of the polymeric immunoglobulin receptor in madin-darby canine cells using retroviral vectors," Chapter 13 in *Methods in Cell. Biol.* 1989, pp. 329-337, vol. 32.
Breitfeld, P.P. et al. "Postendocytotic sorting of the ligand for the polymeric immunoglobulin receptor in madin-darby canine kidney cells," *J. Cell Biology* 1989, pp. 475-486, vol. 109.
Eiffert, H. et al. "Die primärstruktur der menschlichen freien sekretkomponente und die anordnung der disulfidbrüken," *Physiol. Chem.* 1984, pp. 1489-1495, vol. 365 (English abstract included).
Ferkol, T. et al. "Gene transfer into respiratory epithelial cells by targeting the polymeric immunoglobulin receptor," *J. Clin. Invest.* Nov. 1993, pp. 2394-2400, vol. 92.

Ferkol, T. et al. "Gene transfer into the airway epithelium of animals by targeting the polymeric immunoglobulin receptor," *J. Clin. Invest.* 1995, pp. 493-502, vol. 95.
Hudson, L. and Hay, F.C., eds. *Practical Immunology.* 2nd Edition, Blackwell Scientific Publications, Oxford, London, 1980, pp. 192-202.
Mazanec, M.B. et al. "Intracellular neutralization of influenza virus by immunoglobulin A anti-hemagglutinin monoclonal antibodies," *J. Virol.* Feb. 1995, pp. 1339-1343, vol. 69, No. 2.
Mostov, K.E. "Transepithelial transport of immunoglobulins," *Ann. Rev. Immunol.* 1994, pp. 63-84, vol. 12.
Mostov, K.E. et al. "The receptor for transepithelial transport of IgA and IgM contains multiple immunoglobulin-like domains," *Nature* Mar. 1, 1984, pp. 37-43, vol. 308.
Mostov, K.E. et al. "Receptor-mediated transcellular transport of immunoglobulin: synthesis of secretory component as multiple and larger transmembrane forms," *PNAS USA* Dec. 1980, pp. 7257-7261, vol. 77, No. 12.
Piskurich, J.F. et al. "Molecular cloning of the mouse polymeric Ig receptor," *J. of Immunol.* 1995, pp. 1735-1747, vol. 154.
Solari, R. et al. "Antibodies recognizing different domains of the polymeric immunoglobulin receptor," *J. Biol. Chem.* 1985, pp. 1141-1145, vol. 260, No. 2.
Solari, R. et al. "Distribution and processing of the polymeric immunoglobulin receptor in the rat hepatocyte: morphological and biochemical characterization of subcellular fractions," *J. Histochem. & Cytochem.* 1986, pp. 17-23, vol. 34, No. 1.
Williams, G. "Novel antibody reagents: production and potential," *TIBTECH* Feb. 1988, pp. 36-42, vol. 6.
Wu, G.Y. and Wu, C.H. "Receptor-mediated in vitro gene transformation by a soluble DNA carrier system," *J. Biol. Chem.* 1987, pp. 4429-4432, vol. 262.

* cited by examiner

*Primary Examiner*—Michail A Belyavskyi
(74) *Attorney, Agent, or Firm*—Townsend and Townsend and Crew LLP

(57) ABSTRACT

The invention provides compositions and methods for specific binding to a region of the polymeric immunoglobulin receptor (pIgR) of a cell with the provisos that the ligand does not substantially bind to the most abundant form of the secretory component (SC) of pIgR present in an organ of interest of an animal of interest under physiological conditions, and does not bind to the pIgR stalk. In some embodiments, the ligand decreases cleavage of SC from the stalk by at least one-third. The ligands and methods of the invention can be used with both birds and mammals. In more preferred embodiments, the animal is a mammal. In the most preferred embodiment, the animal is a human. The ligand may be targeted into the cell or may undergo retrograde transcytosis and release at the basolateral side of the cell, and may comprise a biologically active composition.

7 Claims, 5 Drawing Sheets

Figure 1:
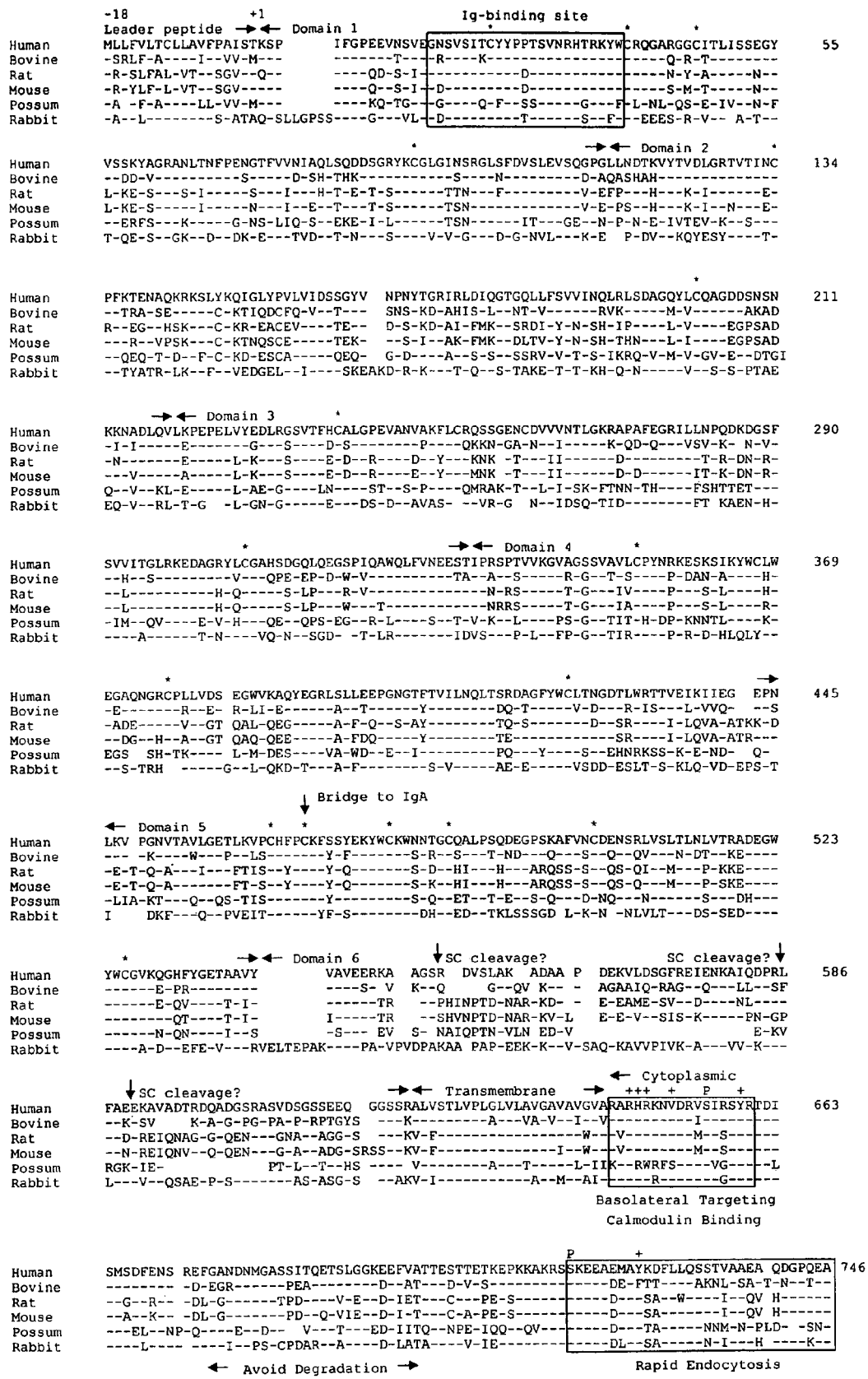

```
         10         20         30         40         50         60
          |          |          |          |          |          |
    MLLFVLTCLL AVFPAISTKS PIFGPEEVNS VEGNSVSITC YYPPTSVNRH TRKYWCRQGA 70         80         90        100        110        120
          |          |          |          |          |          |
    RGGCITLISS EGYVSSKYAG RANLTNFPEN GTFVVNIAQL SQDDSGRYKC GLGINSRGLS 130        140        150        160        170        180
          |          |          |          |          |          |
    FDVSLEVSQG PGLLNDTKVY TVDLGRTVTI NCPFKTENAQ KRKSLYKQIG LYPVLVIDSS 190        200        210        220        230        240
          |          |          |          |          |          |
    GYVNPNYTGR IRLDIQGTGQ LLFSVVINQL RLSDAGQYLC QAGDDSNSNK KNADLQVLKP 250        260        270        280        290        300
          |          |          |          |          |          |
    EPELVYEDLR GSVTFHCALG PEVANVAKFL CRQSSGENCD VVVNTLGKRA PAFEGRILLN 310        320        330        340        350        360
          |          |          |          |          |          |
    PQDKDGSFSV VITGLRKEDA GRYLCGAHSD GQLQEGSPIQ AWQLFVNEES TIPRSPTVVK 370        380        390        400        410        420
          |          |          |          |          |          |
    GVAGSSVAVL CPYNRKESKS IKYWCLWEGA QNGRCPLLVD SEGWVKAQYE GRLSLLEEPG 430        440        450        460        470        480
          |          |          |          |          |          |
    NGTFTVILNQ LTSRDAGFYW CLTNGDTLWR TTVEIKIIEG EPNLKVPGNV TAVLGETLKV 490        500        510        520        530        540
          |          |          |          |          |          |
    PCHFPCKFSS YEKYWCKWNN TGCQALPSQD EGPSKAFVNC DENSRLVSLT LNLVTRADEG 550        560        570        580        590        600
          |          |          |          |          |          |
    WYWCGVKQGH FYGETAAVYV AVEERKAAGS RDVSLAKADA APDEKVLDSG FREIENKAIQ 610        620        630        640        650        660
          |          |          |          |          |          |
    DPRLFAEEKA VADTRDQADG SRASVDSGSS EEQGGSSRAL VSTLVPLGLV LAVGAVAVGV 670        680        690        700        710        720
          |          |          |          |          |          |
    ASARHRKNVD RVSIRSYRTD ISMSDFENSR EFGANDNMGA SSITQETSLG GKEEFVATTE 730        740        750        760
          |          |          |          |
    STTETKEPKK AKRSSKEEAE MAYKDFLLQS STVAAEAQDG PQEA
```

FIGURE 2

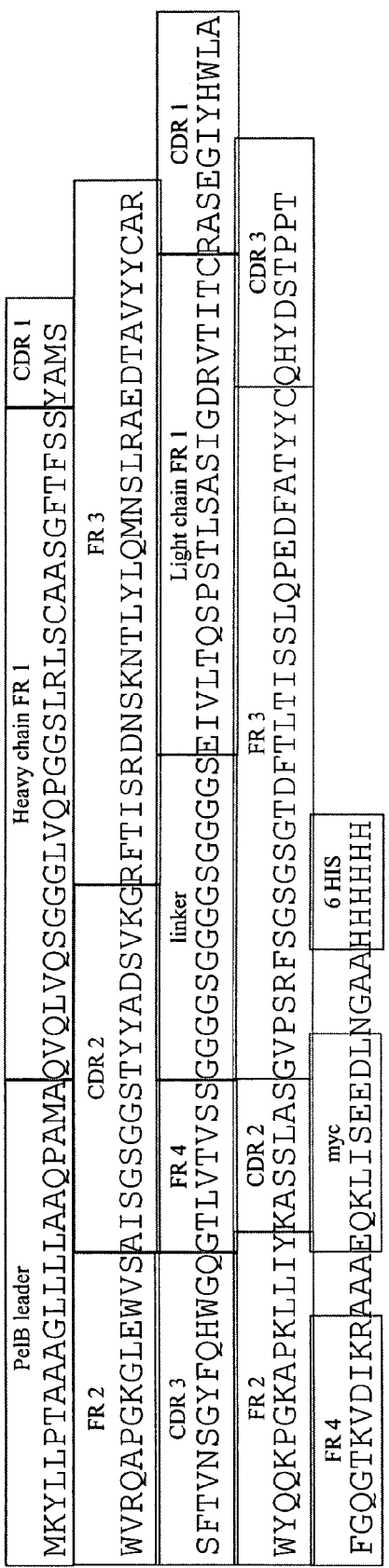

The amino acid sequence of the secreted form of the ScFv 4A is shown. The ScFv consists of a pelb leader (for secretion in E. coli), a heavy chain variable region, a linker sequence (GGGS repeated three times), a light chain variable region, a myc epitope tag and a 6HIS tag (for purification by Immobilized Metal-ion Affinity Chromatography (IMAC)). The framework (FR) and complementarity-determining regions (CDR) of the heavy chain and light chain are indicated.

FIGURE 5

US 7,404,954 B2

METHODS OF TARGETING AGENTS TO CELLS EXPRESSING THE POLYMERIC IMMUNOGLOBULIN RECEPTOR

CROSS-REFERENCES TO RELATED APPLICATIONS

This application is a divisional application of U.S. patent application Ser. No. 09/818,247, filed Mar. 26, 2001, now U.S. Pat. No. 6,855,810, which claims priority from U.S. Provisional Patent Application No. 60/192,197, filed Mar. 27, 2000, and U.S. Provisional Patent Application No. 60/192,198, filed Mar. 27, 2000. The contents of all of these applications are incorporated herein by reference.

STATEMENT AS TO RIGHTS TO INVENTIONS MADE UNDER FEDERALLY SPONSORED RESEARCH AND DEVELOPMENT

This invention was made with government support under grant number AI39161 awarded by the National Institute of Allergy and Infectious Diseases of the U.S. National Institutes of Health. The government has certain rights in the invention.

FIELD OF THE INVENTION

The present invention relates, in general, to compositions and methods for the specific binding of a ligand to a region of the polymeric immunoglobulin receptor ("pIgR") which is not within the stalk nor in the most abundant species of the secretory component as it exists in an organ or on a tissue of interest, for internalization into, or transport across, a cell which secretes pIgR.

BACKGROUND OF THE INVENTION

One of the most challenging problems facing the pharmaceutical and biopharmaceutical industries is delivering therapeutic agents past the various semi-permeable membranes within the body. Particularly in the case of macromolecules, the obstacle to cost effective or convenient treatment is often due to the lack of an adequate drug delivery system. In turn, this issue dictates whether production of a drug is economically feasible. Thus, the search for alternative delivery systems often rivals the search for new drugs themselves.

Gene transfer methods can be viewed as a paradigm of macromolecular drug delivery. These methods can be divided into three categories: physical (e.g., electroporation, direct gene transfer, and particle bombardment), chemical (e.g., proteinoids, microemulsions, and liposomes), and biological (e.g., virus-derived vectors, and receptor-mediated uptake). Among biological transfer methods, receptor-mediated uptake is a particularly promising approach. Targeting a ligand to an endocytosed receptor acts as a means to ferry that ligand into the cell. One drawback of receptor-mediated systems, however, has been their general reliance on intravenous administration, which severely limits their use.

Mucosal epithelial cells line a number of readily accessible tissues such as those found in the upper respiratory and gastrointestinal tracts. The accessibility of these cells make them an attractive target for drug delivery. See, e.g., Ferkol et al., J. Clin. Invest. 92:2394-2400 (1993); Ferkol et al., J. Clin. Invest. 95:493-502 (1995). Retrograde transport of an antibody from the lumenal to the basolateral surface of epithelial cells has been reported, albeit at very low levels. Breitfeld et al., J. Cell Biol. 109:475-486 (1989). In that study, movement across the cell was followed by binding an antibody to the secretory component of polymeric immunoglobulin receptor ("pIgR"). Relative to the level of basolateral to apical transport, Breitfeld et al. reported that less than 5% of the transport was retrograde in nature. The nominal level of counter-transport minimizes the utility of secretory component as a means to deliver biologically active compositions into cells. Moreover, due to the abundance of cleaved pIgR in the lumen, binding of ligand to cleaved pIgR, rather than the intact pIgR of the cell surface, would diminish the utility of pIgR counter-transport as a mechanism of drug delivery.

In commonly-assigned application Ser. No. 08/856,383, now U.S. Pat. No. 6,042,833, it was reported that a stalk remained on the surface of the cell following cleavage of the secretory component ("SC"). It was further found that ligands could be targeted to the stalk and thereafter undergo internalization and retrograde transport. As useful as this is, the stalk represents a limited target for ligands and it would be helpful to have additional targets for ligands which can be internalized and which are not diluted by binding in substantial amounts to cleaved pIgR.

BRIEF SUMMARY OF THE INVENTION

This invention provides ligands that bind specifically to a region of a polymeric immunoglobulin receptor (pIgR) of a cell of an animal, which pIgR when cleaved has a stalk region which remains attached to the cell and a secretory component (SC) which exists in an organ of interest in several forms, provided that the ligands do not substantially bind to the most abundant form of SC present in the organ of interest and provided further that the ligands do not substantially bind to the stalk of said pIgR under physiological conditions. The ligands can bind to the pIgR of birds or of mammals. With regard to mammals, the ligands can bind to the pIgR of a mammal selected from the group consisting of pig, cow, horse, sheep, goat, cat, dog, and human. The ligands can be, for example, an antibody, a humanized antibody, a recombinant single chain variable region fragment of an antibody or a disulfide stabilized variable region fragment.

In some preferred embodiments, the ligands bind to a peptide derived from human pIgR (SEQ ID NO:1), which peptide is selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In some particularly preferred embodiments, the ligands bind to an epitope selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16). The organ of interest may be selected from the group consisting of a small intestine, a large intestine, a liver-biliary tree, a salivary gland, a stomach, a lung, a vagina, a uterus, a lacrimal gland, a mammary gland, a nasal passage, and a sinus.

The ligands may comprise a binding component for binding to pIgR and a biologically active component. In one set of embodiments, the biologically active component is a nucleic acid encoding the wildtype cystic fibrosis transmembrane conductance regulator. In other sets of embodiments, the biologically active component is selected from the group consisting of a nucleic acid, a protein, a radioisotope, a lipid, a carbohydrate, a peptidomimetic, an anti-inflammatory, an antibiotic, and an anti-infective. In yet another embodiment, the biologically active component is a small molecule.

In one set of embodiments, the invention provides ligands that binds specifically to a region of a polymeric immunoglobulin receptor (pIgR) of a cell of an animal, which pIgR has an initial cleavage site and which upon initial cleavage has a stalk region which remains attached to the cell and a secretory component (SC) which exists in an organ of interest in several forms, provided that the ligand does not substantially bind to the most abundant form of SC present in the organ of interest and provided further that the ligand does not substantially bind to a peptide comprising 31 amino acids that are cell-membrane-proximal to the initial cleavage site.

In another group of embodiments, the invention provides a method of introducing a ligand into a cell of an organ of interest in an animal, which cell expresses a polymeric immunoglobulin receptor, by binding the ligand to a region of the polymeric immunoglobulin receptor, with the provisos that (a) the ligand does not substantially bind to a form of secretory component which is the most abundant form present in the organ of interest under physiological conditions and (b) the ligand does not substantially bind to a stalk region of the pIgR, thereby permitting introduction of the ligand into the cell. In some of these embodiments, the ligand is an antibody, and may be a recombinant single chain variable region fragment of an antibody, or a disulfide stabilized variable region fragment, either of which may be humanized. The ligand can selectively bind to a peptide derived from human pIgR (SEQ ID NO:1), which peptide is selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In some preferred embodiments, the ligand binds to an epitope selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16).

The method further encompasses embodiments wherein the ligand is further defined as having a binding component for selectively binding to pIgR and a biologically active component. The biologically active component may be a nucleic acid which encodes the wildtype cystic fibrosis transmembrane conductance regulator. In other embodiments, the biologically active component may be selected the group consisting of a nucleic acid, a protein, a radioisotope, a lipid, a carbohydrate, a peptidomimetic, an anti-inflammatory, an antibiotic, and an anti-infective. In yet another embodiment, the biologically active component is a small molecule. The cell may be a mammalian cell, especially an epithelial cell. The organ of interest may be selected from the group consisting of a small intestine, a large intestine, a liver-biliary tree, a stomach, a salivary gland, a lung, a vagina, a uterus, a lacrimal gland, a mammary gland, a nasal passage, and a sinus.

In another group of embodiments, the invention provides a method of introducing a ligand into a cell of an organ of interest in an animal, which cell expresses a polymeric immunoglobulin receptor (pIgR), which pIgR has an initial cleavage site which, upon initial cleavage has a stalk region, the method comprising binding the ligand to a region of the pIgR, with the provisos that (a) the ligand does not substantially bind to a form of secretory component which is the most abundant form present in the organ of interest under physiological conditions; (b) the ligand does not substantially bind to a stalk region of the pIgR; and (c) the ligand does not bind to an extracellular epitope within the first 31 amino acids that are cell membrane proximal to the initial cleavage site of the pIgR, thereby permitting introduction of the ligand into the cell.

Yet another method provided by the invention is a method of increasing the rate by which a first ligand which binds to secretory component (SC) is internalized into a cell secreting a polymeric immunoglobulin receptor (pIgR) from an apical surface by (a) binding the pIgR with a second ligand, which second ligand inhibits proteolytic cleavage of SC by at least one-third, and further which second ligand does not substantially bind to a stalk remaining attached to the cell after proteolytic cleavage, and (b) binding the first ligand to the SC, thereby permitting internalization into said cell of the SC to which the first ligand is bound.

The invention further provides ligands that binds specifically to a region of a polymeric immunoglobulin receptor (pIgR) of a cell, provided that binding of the ligand reduces proteolytic cleavage of secretory component (SC) by at least one-third compared to the cleavage of SC from a cell in the absence of binding of the ligand and provided further that the ligand does not substantially bind to a stalk of said pIgR remaining after proteolytic cleavage under physiological conditions. The ligand may be an antibody, a scFv, a recombinant single chain variable region fragment of an antibody, a disulfide stabilized variable region fragment ("dsFv"), a humanized scFv, or a humanized dsFv. The ligands may bind to a peptide derived from human pIgR (SEQ ID NO:1), selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In one set of embodiments, the ligand binds to an epitope selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16).

The ligand may further be a binding component of a molecule comprising a biologically active component. In some embodiments, the biologically active component may be selected from the group consisting of: a nucleic acid, a protein, a radioisotope, a lipid, a carbohydrate, a peptidomimetic, an anti-inflammatory, an antibiotic, and an anti-infective. In yet another embodiment, the biologically active component is a small molecule. In yet another, the biologically active component is a nucleic acid encoding the wildtype cystic fibrosis transmembrane conductance regulator.

In yet another set of embodiments. the invention provides a conjugate, fusion protein, or complex, said conjugate fusion protein or complex comprising a ligand that binds specifically to a region of a polymeric immunoglobulin receptor (pIgR) of a cell and a biologically active component, provided that binding of the conjugate, fusion protein, or complex to pIgR reduces proteolytic cleavage of secretory component (SC) by at least one-third compared to the cleavage of SC from a cell in the absence of binding of the conjugate, fusion protein, or complex and provided further that the conjugate, fusion protein, or complex does not substantially bind to a stalk of said pIgR remaining after proteolytic cleavage under physiological conditions.

In another set of embodiments, the invention provides methods of introducing a ligand into a cell expressing a polymeric immunoglobulin receptor (pIgR) by attaching the ligand to a region of the pIgR, provided that (a) binding of the ligand reduces proteolytic cleavage of secretory component (SC) by at least one-third compared to the cleavage of SC from a cell in the absence of the ligand, and (b) the ligand does not substantially bind to a stalk of said pIgR remaining after proteolytic cleavage under physiological conditions, thereby permitting introduction of the ligand into the cell. The ligand may be, for example, an antibody, a humanized antibody, a scFv, a recombinant single chain variable region fragment of an antibody, or a disulfide stabilized variable region. The ligand preferably binds to a peptide derived from human pIgR (SEQ ID NO:1), selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In some embodiments, the ligand binds to an epitope of pIgR selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16). The ligand may have a binding component for selectively binding to a region of pIgR and a biologically active component. The biologically active component may be selected from the group consisting of: a nucleic acid, a protein, a radioisotope, a lipid, a carbohydrate, a peptidomimetic, an anti-inflammatory, an antibiotic, and an anti-infective. In one set of embodiments, the biologically active component is a small molecule. The animal can be a mammal. In one embodiment, the biologically active component is a nucleic acid encodes the wildtype cystic fibrosis transmembrane conductance regulator. The cell can be a mammalian cell, especially an epithelial cell. The ligand can bind to the pIgR at the apical surface of the cell. The ligand can then be transcytosed to the basolateral side of the cell, and may remain attached or can be released from the pIgR at the basolateral surface of the cell. The SC can exist in several forms in an organ of interest, provided that the ligand (a) does not bind to the most abundant form of SC present in the organ of interest, and (b) does not bind to a stalk remaining on an extracellular surface of a cell of the organ of interest after pIgR cleavage. The organ of interest can be selected from the group consisting of a small intestine, a large intestine, a liver-biliary tree, a stomach, a salivary gland, a lung, a vagina, a uterus, a lacrimal gland, a mammary gland, a nasal passage, and a sinus.

The invention further relates to methods of attaching a ligand to a cell expressing a polymeric immunoglobulin receptor comprising the step of binding the ligand to the receptor with the provisos that (a) the ligand reduces proteolytic cleavage of secretory component (SC) by at least one-third compared to the cleavage of SC from a cell in the absence of the ligand, and (b) the ligand does not substantially bind to a stalk of said pIgR remaining after proteolytic cleavage under physiological conditions, thereby attaching the ligand to the cell. The method can permit the ligand to be internalized into the cell after binding.

The invention also provides a method of attaching a conjugate, fusion protein, or complex to a cell expressing a polymeric immunoglobulin receptor, said conjugate, fusion protein, or complex comprising a ligand that binds to a region of pIgR and a biologically active component, said method comprising the step of binding the ligand to the receptor with the provisos that (a) the ligand reduces proteolytic cleavage of secretory component (SC) by at least one-third compared to the cleavage of SC from a cell in the absence of the ligand, and (b) the ligand does not substantially bind to a stalk of said pIgR remaining after proteolytic cleavage under physiological conditions, thereby attaching the conjugate, fusion protein, or complex to the cell.

The invention further provides a method of transcytosing a ligand from an apical to a basolateral side of a cell of an organ of interest in an animal, which cell expresses a polymeric immunoglobulin receptor (pIgR), by binding the ligand to a region of the polymeric immunoglobulin receptor, with the provisos that (a) the ligand does not substantially bind to a form of secretory component which is the most abundant form present in the organ of interest under physiological conditions and (b) the ligand does not substantially bind to a stalk region of the pIgR, thereby permitting introduction of the ligand into the cell. The ligand may be, for example, an antibody, a humanized antibody, a recombinant single chain variable region fragment of an antibody, or a disulfide stabilized variable region fragment. The ligand may selectively bind to a peptide derived from human pIgR (SEQ ID NO:1), which peptide is selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In one set of preferred embodiments, the ligand may bind to an epitope selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16). In some embodiments of the method, the ligand may further be defined as having a binding component for selectively binding to pIgR and a biologically active component. The biologically active component is selected from the group consisting of a nucleic acid, a peptide, a protein, a radioisotope, a lipid, a carbohydrate, a peptidomimetic, an anti-inflammatory, an antisense oligonucleotide, an antibiotic, and an anti-infective. In one set of embodiments, the biologically active component can be a small molecule. The method can be used with respect to a mammalian cell, and especially where the cell is an epithelial cell. The organ of interest can be selected from the group consisting of a small intestine, a large intestine, a liver-biliary tree, a stomach, a salivary gland, a lung, a vagina, a uterus, a lacrimal gland, a mammary gland, a nasal passage, and a sinus.

The invention further provides a method of transcytosing a ligand from an apical to a basolateral side of a cell of an organ of interest in an animal, which cell expresses a polymeric immunoglobulin receptor (pIgR), which pIgR has an initial cleavage site which, upon initial cleavage has a stalk region, the method comprising binding the ligand to a region of the pIgR, with the provisos that (a) the ligand does not substantially bind to a form of secretory component which is the most abundant form present in the organ of interest under physiological conditions; (b) the ligand does not substantially bind to a stalk region of the pIgR; and (c) the ligand does not bind to an extracellular epitope within the first 31 amino acids that are cell membrane proximal to the initial cleavage site of the pIgR, thereby permitting introduction of the ligand into the cell.

Figure 3:
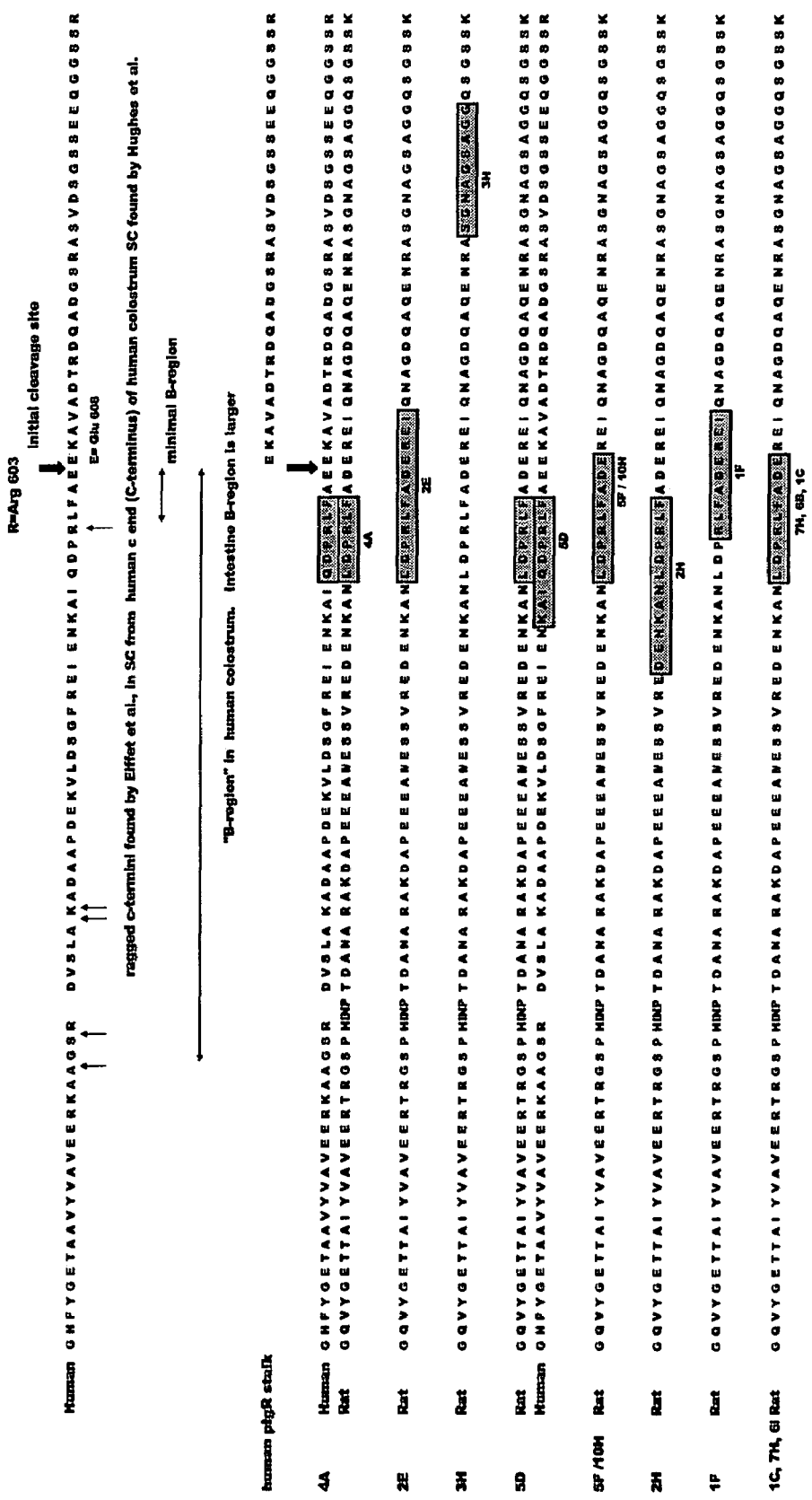
Figure 4:
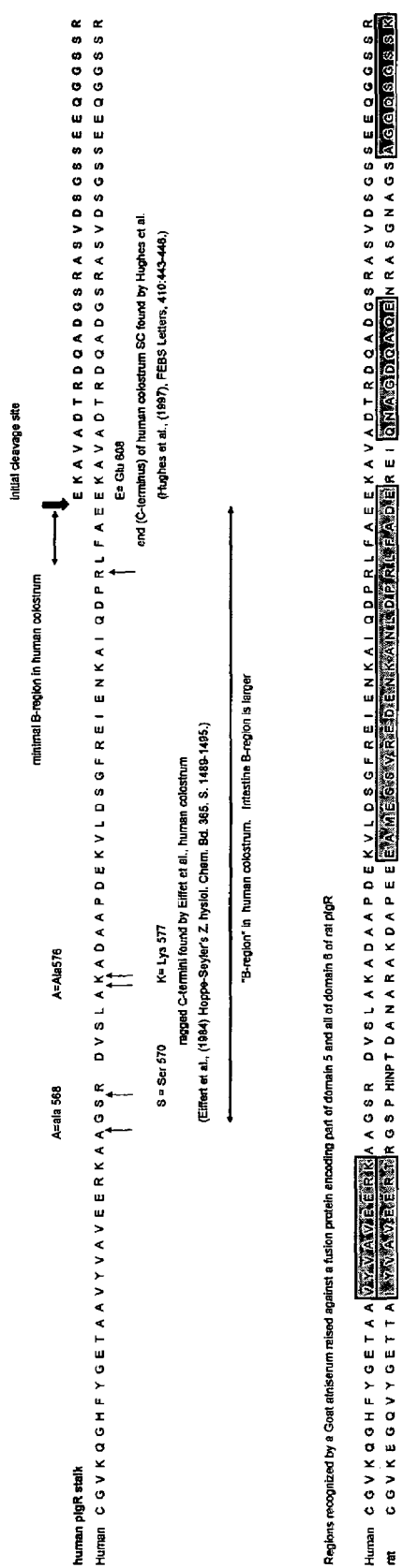

The invention additionally provides a method of transcytosing a ligand from an apical to a basolateral side of a cell of an organ of interest in an animal, which cell expresses a polymeric immunoglobulin receptor (pIgR), by attaching the ligand to a region of the pIgR, provided that (a) binding of the ligand reduces proteolytic cleavage of secretory component (SC) by at least one-third compared to the cleavage of SC from a cell in the absence of the ligand, and (b) the ligand does not substantially bind to a stalk of said pIgR remaining after proteolytic cleavage under physiological conditions, thereby permitting transcytosis of the ligand from the apical side to the basolateral side of the cell. The ligand can be, for example, an antibody, including a humanized antibody, a scFv (including a recombinant single chain variable region fragment of an antibody), and a disulfide stabilized variable region. The ligand can bind to a peptide derived from human pIgR (SEQ ID NO:1), selected from the group consisting of: Lys487-Arg603, Lys487-Glu607, Lys487-Val611, Lys487-Arg615, Lys487-Ala618, Cys520-Arg603, Cys520-Glu607, Cys520-Val611, Cys520-Arg615, Cys520-Ala618, Lys577-Arg603, Lys577-Glu607, Lys577-Val611, Lys577-Arg615, Lys577-Ala618, Ser574-Arg603, Ser574-Glu607, Ser574-Val611, Ser574-Arg615, Ser574-Ala618, Val560-Arg603, Val560-Glu607, Val560-Val611, Val560-Arg615, Val560-Ala618, Cys544-Arg603, Cys544-Glu607, Cys544-Val611, Cys544-Arg615, and Cys544-Ala618. In some preferred embodiments, the ligand binds to an epitope of pIgR selected from the group consisting of QDPRLF (SEQ ID NO:10), LDPRLF (SEQ ID NO:11), KAIQDPRLF (SEQ ID NO:12), LDPRLFADEREI (SEQ ID NO:13), DENKANLDPRLF (SEQ ID NO:14), RLFADEREI (SEQ ID NO:15), and LDPRLFADE (SEQ ID NO:16).

In one group of embodiments of this method, the ligand is further defined as having a binding component for selectively binding to a region of pIgR and a biologically active component. The biologically active component can be a nucleic acid, a peptide, a protein, a radioisotope, a lipid, a carbohydrate, a peptidomimetic, an anti-inflammatory, an antisense oligonucleotide, an antibiotic, and an anti-infective. In one group of embodiments, the biologically active component is a small molecule. The animal can be a mammal, and the cell can be a mammalian cell, and preferably is an epithelial cell.

The invention further provides a method of increasing the rate by which a first ligand which binds to secretory component (SC) is transcytosed from an apical to a basolateral side of a cell of an organ of interest in an animal, which cell expresses a polymeric immunoglobulin receptor (pIgR) from an apical surface by (a) binding the pIgR at the apical side of said cell with a second ligand, which second ligand inhibits proteolytic cleavage of SC by at least one-third, and further which second ligand does not substantially bind to a stalk remaining attached to the cell after proteolytic cleavage, and (b) binding the first ligand to the SC, thereby permitting transcytosis of the SC to which the first ligand has bound from the apical to the basolateral side of said cell.

BRIEF DESCRIPTION OF THE DRAWINGS

FIG. 1. FIG. 1 shows an alignment of the sequences of the human (SEQ ID NO:1), bovine (SEQ ID NO:2), rat (SEQ ID NO:3), mouse (SEQ ID NO:4), possum (SEQ ID NO:5), and rabbit (SEQ ID NO:6) pIgR, including a leader sequence (labeled "Leader peptide" in the Figure) which is not present in the mature pIgR molecule. Residues identical to those of the human sequence at the same location are shown as dashes, residues differing at a particular point are shown. Ends of domains are denoted by opposed arrows. Some of the cleavage sites for the secretory component suggested by the experimental evidence (see text) are marked by vertical arrows. The box in the top portion of the figure labeled "Ig-binding site" denotes the site at which IgA binds to pIgR and is not the intended target of the ligands discussed herein. The vertical arrow labeled "Bridge to IgA" designates a cysteine which forms a disulfide bond to IgA. Stars designate the cysteine residues. The opposed arrows to the left of the label "Transmembrane" denote the end of the transmembrane domain and the start of the extracellular portion of pIgR. The extracellular portion of pIgR closest to the transmembrane domain comprises the stalk. Note: as described in more detail in the text, the numbering of the residues of human pIgR in FIG. 1 does not include the 18 residue leader sequence counted in the numbering system used in the SWISS-PROT database and followed in the text.

FIG. 2. FIG. 2 shows the sequence of human pIgR (SEQ ID NO:1) as set forth in the SWISS-PROT database under accession number P01833. The amino acids in the sequence are set forth in standard single-letter code.

FIG. 3 FIG. 3 shows the results of experiments mapping the epitopes of pIgR recognized by various scFv antibodies from a human library. The lines marked "Human" set forth a portion of the amino acid sequence of human pIgR (the portion set forth is SEQ ID NO:17), encompassing part of domain 5 and all of domain 6. The sequences marked "Rat" set forth a corresponding portion of the amino acid sequence of rat pIgR (the portion set forth is SEQ ID NO:18). A further line sets forth the sequence of the human pIgR stalk (SEQ ID NO:19). The downward arrows denote the initial cleavage site of pIgR. The upward arrows denote various C termini of the SC of human colostrum found by Eiffert et al. or by Hughes et al. The shorter horizontal, double-ended arrow denotes the minimal colostrum B region, which is bounded by the initial pIgR cleavage site on the C terminal side, and by the C terminus found by Hughes et al. on the other. The longer horizontal, double-ended arrow denotes the maximal colostrum B region, bounded by the initial cleavage site on the C terminal side of the B region and by the most amino terminal residue found by Eiffert et al. on the other. It should be noted that other organs, such as the intestine, have more and greater concentrations of proteases, so the B region in those organs is expected to be bigger. The number and letter combinations, such as "4A," denote particular scFvs. The shaded boxes show the epitopes to which the designated scFv bound. As shown, certain epitopes were bound by more than one scFv.

FIG. 4 FIG. 4 shows the results of studies mapping the epitopes of pIgR recognized by polyclonal antibodies raised in a goat in response to immunizations with a fusion protein comprising a portion of rat pIgR. The lines labeled "Human" set forth a portion of the human pIgR sequence than used in FIG. 3 (the sequence in this Figure is SEQ ID NO:20). The line labeled "Rat" sets forth a portion of the rat pIgR sequence (the sequence used in this Figure is SEQ ID NO:21). The downward facing, upward facing and horizontal arrows are as described for FIG. 3. The shaded boxes show where the polyclonal antibodies bound in the mapping studies.

FIG. 5 FIG. 5 shows the amino acid sequence (SEQ ID NO:22) of a secreted form of scFv 4A, bearing two labels: the FLAG® (SEQ ID NO:22) epitope and an epitope from the myc oncogene, as well as a six-histidine tail for easy purification. PelB leader: PelB leader promotes secretion of the peptide from *E. coli*. FLAG®: FLAG® (SEQ ID NO:22) epitope. Heavy chain FR: Framework region of immunoglobulin heavy chain. Light chain FR: Framework region of immunoglobulin light chain. CDR: complementarity determining region. Numbers after the abbreviations designate the particular numbered region, e.g., CDR3 designates complementarity determining region 3, which is considered in the art to have the greatest contact with the target epitope of the antigen. Linker: linker peptide used in 4A construct (GGGS=SEQ ID NO:23). myc: epitope from myc oncogene recognized by commercially available antibodies. 6 HIS: 6 histidine tail.

DETAILED DESCRIPTION

Introduction

The present invention is directed to a ligand that binds specifically to a portion of a polymeric immunoglobulin receptor (pIgR) of a cell with the provisos that the ligand does not substantially bind to the most abundant species (or form) of the secretory component present in an animal tissue, organ, or lumen, or to the stalk remaining on the extracellular surface of the cell after pIgR is cleaved. The invention provides, inter alia, methods of attaching and introducing a ligand into a cell expressing pIgR.

After transport to the apical surface of epithelial cells, the pIgR undergoes an initial cleavage and the secretory component (sometimes hereafter abbreviated as "SC"), comprising the bulk of the molecule, is released into the extracellular space, while a residual extracellular region of pIgR (the "stalk") remains accessible on the cell surface. Newly-cleaved SC contains a carboxy-terminal region adjacent to the cleavage site which is rapidly degraded by proteases to provide the SC typically found in the lumenal space, such as the mammalian intestine. Hereafter, the region of the SC adjacent to the cleavage site which undergoes further proteolytic digestion or secondary cleavage following cleavage from intact pIgR is sometimes referred to as the "B region."

Since the B region is rapidly degraded, the most abundant form of the SC present in the extracellular space (for example, SC present in the animal intestine and, in particular, the mammalian small and large intestines) does not contain it. Hereafter, this processed SC is referred to interchangeably as the "most abundant form," "most abundant species," or "major species" of SC present in an organ of interest (such as in the lumen of the intestine or on the surface of the lung) or on a tissue of interest (such as on the surface of nasal or sinus passages, etc.) when the distinction from newly-cleaved, but as yet unprocessed, SC is necessary. In the intestinal tract, which has particularly high levels of proteases, some of the SC may undergo further proteolysis, but a substantial amount of the SC survives intestinal degradation and is excreted in the feces. While the level of proteases is highest in the intestines, proteases exist in the lumen of other organs and on mucosal surfaces. Thus, degradation of the B region is not limited to the intestinal tract.

While rapid, the cleavage of the pIgR at the apical surface is not instantaneous. Thus, there exists a limited pool of uncleaved, intact pIgR at the cell surface. As the pIgR is cleaved and the SC undergoes rapid processing, however, the epitopes to which ligands directed to the B region bind are destroyed. This offers a surprising advantage to using ligands targeted to this region compared to ligands targeted to the remaining, much larger, portion of the SC. Because the epitopes to which ligands targeted to the B region are rapidly degraded after pIgR cleavage, a high proportion of ligands directed to the B region bind to intact pIgR and are available for internalization and transcytosis to the basolateral surface of the cell. In contrast, ligands directed to other portions of the SC will bind both to intact pIgR and to SC present in the extracellular space; thus, a markedly smaller proportion of such ligands will bind to intact pIgR than will ligands targeted to the B region. Since ligands bound to free SC do not internalize into a pIgR-expressing cell, these ligands will not be available to be transcytosed from the apical surface to the basolateral surface of the cell, and a correspondingly higher amount of such ligands will have to be introduced to accomplish transcytosis of a given amount of ligand to the basolateral surface. Thus, if retrograde transport of the ligand from the lumen to the basolateral side of a pIgR-expressing cell is desired, it is advantageous if the ligand binds to the B region rather than to portions of the SC not within the B region. This advantage of ligands targeted to the B region has not previously been recognized or exploited in the art.

Even more advantageously, ligands can be directed specifically to the area of or around the initial cleavage site at which SC is severed from the stalk, thereby inhibiting cleavage of secreted pIgR. For example, ligands directed to this region can sterically block access of proteases to the cleavage site. A higher proportion of such ligands will be internalized into the pIgR-secreting cell compared to ligands which bind to areas of the SC on the N-terminal side of the B region, for two reasons. First, since the ligand prevents the pIgR from being cleaved, the intact pIgR is available to be reinternalized, along with the ligand. Second, ligands which inhibit cleavage are unlikely to bind to free SC since free SC is unlikely to have the epitope or other conformation recognized by a ligand which has this functionality. Thus, such ligands are especially advantageous.

In some embodiments, the ligand itself may not be large enough to impede access of a protease to the initial pIgR cleavage site, but the ligand may be conjugated, fused, or complexed to another moiety (such as a peptide, nucleic acid, antibody, radioisotope, lipid, carbohydrate, small molecule, peptidomimetic, radioisotope, antibiotic, anti-infective, or the like), and the conjugate, fusion protein, or complex may be large enough to impede access by the protease. These conjugates, fusions, and complexes are also within the scope of the present invention.

The ability of ligands or of conjugates, fusions, or complexes, to inhibit or block cleavage of the SC can be readily determined by assays determining the rate of SC cleavage in the presence and in the absence of the ligand, conjugate, fusion, or complex. A number of assays are known in the art; an exemplary assay, using a pulse-chase technique, is set forth in the Examples.

The present invention has utility as a means of transporting therapeutic or diagnostic compositions to, into (endocytosis) or across (transcytosis) a cell expressing pIgR. Thus the invention can be used to transport biologically active compositions such as proteins, nucleic acids, or detectable labels specifically to cells expressing pIgR. The invention also provides a means of labeling and distinguishing epithelial cells from among a mixed cell population in pathology studies. Further, since pIgR expression is reduced in carcinomas relative to normal epithelium, the labeling of pIgR has utility as a diagnostic adjunct in endoscopic or radiologic procedures. Additionally, binding of therapeutic ligands to pIgR has utility in extending the duration of the ligands in the lumen of various passageways and increasing their effectiveness.

The invention can be used in a number of contexts. pIgR is secreted on mucosal surfaces throughout the body, including the gastrointestinal tract, most if not all of the genito-urinary tract, the entire respiratory system, from nose and sinuses to the aveloli of the lung, and the lacrimal glands of the eye. Thus, the invention can be used, for example, to deliver agents to (a) the gastrointestinal tract, including the stomach, small intestine, or large intestine, through oral administration or endoscopic administration, (b) the mouth, and specifically the salivary glands, by, for example, cannulation of the glands, (c) the liver-biliary tree, by endoscopic retrograde cannulation of the pancreatic duct or bile duct (these are a common duct in most humans), (d) to the nose or sinuses, by nose drops or sprays, (e) to the lung, typically by inhalation of aerosolized mists (see, e.g., U.S. Pat. Nos. 5,960,792, 5,934,272, 5,906, 202, and 5,622,162) or finely dispersible dry powders (see, e.g., U.S. Pat. Nos. 5,740,794, and 5,458,135), (f) to the vagina, by spray, douche, or suppository, (g) to the uterus, typically by spray, (h) to the anus, typically by suppository, (i) to the mammary gland, typically by cannulation, to treat infectious, hormonal, or other conditions, and, (j) to the eyes, and especially the conjunctiva, by eye drops or opthalmic ointments. These applications permit localized delivery of the therapeutic agent to an affected organ or tissue, often with higher concentrations than can be easily achieved with systemic administration. For example, a therapeutic agent can be delivered to the tissues surrounding the conjunctiva or lacrimal gland or associated structures and ducts in a person with an infectious or inflammatory eye condition by using eye drops incorporating the compositions of the invention.

The ligands and methods of the invention can generally be used to deliver compositions to animals which express pIgR and in which a secretory component of pIgR is cleaved away, leaving a stalk. In some embodiments, for example, the invention is used in birds, which are known to express SC. The invention is especially useful for birds reared for human consumption, such as chickens, turkeys, ducks, and ostriches. These birds are raised commercially in flocks and the invention provides a new and convenient method of administering veterinary compositions to one or more members of a flock. The invention can also be used, however, with respect to individual birds, such as parrots, cockatiels, and macaws, being raised for sale or kept as pets, as well as to other birds, such as sea birds rescued from oil slicks, to which veterinary attention may be directed.

In preferred embodiments, the invention is used to deliver compositions to mammals. In veterinary uses, the invention can be used as a means of administering therarpeutic compositions to pigs, sheep, goats, cows, dogs, cats, horses, and other farm and domestic animals. In one group of embodiments, the invention can be used to deliver therapeutic formulations to populations of wild animals, such as raccoons, foxes, bison, elk, rodents, and the like, to reduce the likelihood of their spreading disease to farm animals or human populations. In the most preferred embodiments, the invention is used to administer compositions of interest, such as therapeutic compositions, to humans.

Definitions

Unless defined otherwise herein, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology*, Harper Perennial, NY provide one of skill with a general dictionary of many of the terms used in this invention. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. For purposes of the present invention, the following terms are defined below.

By "pIgR" or "polymeric immunoglobulin receptor" is meant the receptor which is expressed in mucosal epithelial cells, including airway epithelial cells, submucosal gland cells, intestinal cells, nasal epithelium, breast, oral mucosa, urinary and reproductive tract epithelium, and conjunctival tissue, and is implicated in basolateral to apical transcytosis of dimeric immunoglobulin A (dIgA) and/or pentameric IgM. Both mammals and birds express pIgR. The nucleic acid and amino acid sequence of the polymeric immunoglobulin receptor has been identified in a variety of taxonomically diverse species. See, Piskurich et al., *Journal of Immunology* 154:1735-1747 (1995); the amino acid sequences for human pIgR (SEQ ID NO:1), bovine pIgR (SEQ ID NO:2), rat pIgR (SEQ ID NO:3), mouse pIgR (SEQ ID NO:4), possum pIgR (SEQ ID NO:5) and rabbit pIgR (SEQ ID NO:6) are set forth in FIG. 1. As explained in more detail below, the most common current numbering system for pIgR counts the leader sequence and therefore accords the residues a position 18 places higher than the numbers set forth for the same residues in FIG. 1.

By "stalk" is meant the extracellular component of the polymeric immunoglobulin receptor (pIgR) that corresponds to that region of pIgR that is bound to the cell following cleavage of that segment of pIgR which constitutes the secretory component. The stalk is present regardless of whether the segment of pIgR which corresponds to secretory component is cleaved or uncleaved from pIgR.

By "secretory component" or "SC" is meant that extracellular portion of pIgR which is generally cleaved following basolateral to apical transcytosis. Typically, the secretory component comprises the dimeric IgA (dIgA) binding portion of pIgR. Secretory component is typically released into the lumen with or without dIgA bound to the secretory component.

The term "B region" refers to a portion of SC which undergoes rapid proteolytic digestion or secondary cleavages after cleavage of the SC from intact pIgR in an tissue of interest or organ of interest which secretes pIgR. The B region is therefore absent from the majority of free SC as it exists, for example, in the mammalian small and large intestines. The SC, and the proteolytic processes which result in the degradation of the "B region," also occur in certain non-mammalian animals, such as birds. The term "B region" therefore further relates as appropriate to the portion of the SC of birds, such as chickens and turkeys, which rapidly degrades after cleavage of the SC.

The terms "major species," "most abundant species," and "most abundant form" are generally used interchangeably herein and refer to the most abundant form of the SC in the organ of interest or on the tissue of interest of an animal species under consideration. For example, with respect to oral administration to the intestine of an animal, the terms refer to the most abundant form in the intestinal tract of the animal and, with reference to humans, refers to the most abundant form in the human intestinal tract.

A "tissue of interest" refers to those tissues, such as those of the nasal cavity, the paranasal sinuses, and the lacrimal glands of the eyes, which secrete pIgR into adjacent fluids, such as mucus in the nasal passages in the case of the nasal cavity or tears on the conjunctiva in the case of the lacrimal glands, but which are not conveniently described as being part of a discrete organ.

An "organ of interest" refers to an organ containing a lumen or other internal space (such as the interior surface of the lung or of the uterus) into which pIgR is secreted and to which a practitioner wishes to deliver ligands of the invention. Suitable organs include the organs of the gastrointestinal tract, the liver-biliary tree, the lungs, the vagina, and the uterus. References herein to the most abundant form of SC in the organ refer to the most abundant form of SC in the lumen or internal space of the organ.

The distinction between a "tissue of interest" and an "organ of interest" is made herein for clarity in discussions relating to the definition of the major form of SC present. In a "tissue of interest," the major form of the SC is that in the fluids (such as mucus or tear) on the surfaces around the pIgR-secreting cells. Thus, the major form of the SC in the nasal passages is the major form found in the mucus inside the nose. In an "organ of interest," the major form of SC is that found within the lumen of the organ (such as the intestine) or in a internal space into which the organ (such as the uterus or vagina) secretes pIgR, and, in the case of organs in which the major form of the SC may be different at different sites (such as in the small intestine, where the number and concentration of proteases may be different in the duodenum and in the ileum), it generally means at the site of intended administration. Except where necessary for clarity, as used herein, the term "tissue of interest" is encompassed herein by the term "organ of interest."

By "ligand" or "ligand binding moiety", is meant all molecules capable of specifically binding to the polymeric immunoglobulin receptor (pIgR). Ligands include, but are not limited to, antibodies, proteins, peptides, nucleic acids, lipids, and carbohydrates.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments, or pFv fragments. The term "antibody" also includes antigen binding forms of antibodies (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1997).

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

A "targeting moiety" is the portion of an immunoconjugate intended to target the immunoconjugate to cells of interest. Typically, the targeting moiety is an antibody, a scFv, a dsFv, an Fab, or an F(ab')$_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient. It further includes nucleic acids, including antisense molecules. As used herein, it further encompasses prophylatic and therapeutic vaccines, such as proteins which are intended to cause a heightened immune response to an infectious disease or a cancer, as well as nucleic acids encoding such proteins.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell to which the moiety is delivered by the targeting moiety or to identify the presence of the immunoconjugate. Thus, the effector moiety can be, for example, a therapeutic moiety or a detectable label, such as a radiolabel or a fluorescent label.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "contacting" includes reference to placement in direct physical association.

An "expression plasmid" comprises a nucleotide sequence encoding a molecule of interest, which is operably linked to a promoter.

As used herein, the term "anti-pIgR" in reference to an antibody, includes reference to an antibody which is generated against pIgR. In preferred embodiments, the pIgR is a primate pIgR such as human pIgR. In a preferred embodiment, the antibody is generated against human pIgR synthesized by a non-primate mammal after introduction into the animal of cDNA which encodes human pIgR.

As used herein, the term "polypeptide" includes proteins, fusion proteins, oligopeptides and polypeptide derivatives, with the exception that peptidomimetics are considered to be small molecules herein. Although they are polypeptides, antibodies and their derivatives are described separately.

A "protein" is a molecule having a sequence of amino acids that are linked to each other in a linear molecule by peptide bonds. The term protein refers to a polypeptide that is isolated from a natural source, or produced from an isolated cDNA using recombinant DNA technology; and has a sequence of amino acids having a length of at least about 200 amino acids.

A "fusion protein" is a type of recombinant protein that has an amino acid sequence that results from the linkage of the amino acid sequences of two or more normally separate polypeptides. In the context of the present invention, the term usually refers to a ligand, such as an antibody, linke to a biologically active molecule, such as a chemotherapeutic agent or an anti-infective.

A "protein fragment" is a proteolytic fragment of a larger polypeptide, which may be a protein or a fusion protein. A proteolytic fragment may be prepared by in vivo or in vitro proteolytic cleavage of a larger polypeptide, and is generally too large to be prepared by chemical synthesis. Proteolytic fragments have amino acid sequences having a length from about 200 to about 1,000 amino acids.

An "oligopeptide" is a polypeptide having a short amino acid sequence (i.e., 2 to about 200 amino acids). An oligopeptide is generally prepared by chemical synthesis. Although oligopeptides and protein fragments may be otherwise prepared, it is possible to use recombinant DNA technology and/or in vitro biochemical manipulations. For example, a nucleic acid encoding an amino acid sequence may be prepared and used as a template for in vitro transcription/translation reactions.

A "polypeptide derivative" includes without limitation mutant polypeptides, chemically modified polypeptides, and peptidomimetics. The polypeptides or derivatives may generally be prepared by solid phase synthetic methods as taught in, e.g., Merrifield (1964), J. Am. Chem. Soc., 85: 2149; Stewart and Young (1984), Solid Phase polypeptide Synthesis, Pierce Chemical Company, Rockford, Ill.; Bodansky and Bodanszky (1984), The Practice of polypeptide Synthesis, Springer-Verlag, New York; Atherton and Sheppard (1989), Solid Phase polypeptide Synthesis: A Practical Approach, IRL Press, New York, or by recombinant techniquest using polynucleotide sequences encoding the polypeptides. For example, fusion proteins are typically prepared using recombinant DNA technology.

A "derivative" of a polypeptide is a compound that is not, by definition, a polypeptide, i.e., it contains at least one chemical linkage that is not a peptide bond. Thus, polypeptide derivatives include without limitation proteins that naturally undergo post-translational modifications such as, e.g., glycosylation. Preferred polypeptide derivatives retain a desirable attribute, which may be biological activity; more preferably, a polypeptide derivative is enhanced with regard to one or more desirable attributes, or has one or more desirable attributes not found in the parent polypeptide.

A polypeptide having an amino acid sequence identical to that found in a protein prepared from a natural source is a "wildtype" polypeptide. "Mutant polypeptides" can be prepared by chemical synthesis, including without limitation combinatorial synthesis. Mutant polypeptides larger than oligopeptides can be prepared using recombinant DNA technology by altering the nucleotide sequence of a nucleic acid encoding a polypeptide. Although some alterations in the nucleotide sequence will not alter the amino acid sequence of the polypeptide encoded thereby ("silent" mutations), many will result in a polypeptide having an altered amino acid sequence that is altered relative to the parent sequence. Such altered amino acid sequences may comprise substitutions, deletions and additions of amino acids, with the proviso that such amino acids are naturally occurring amino acids.

Polypeptides having deletions or insertions of naturally occurring amino acids may be synthetic oligopeptides that result from the chemical synthesis of amino acid sequences that are based on the amino acid sequence of a parent polypeptide but which have one or more amino acids inserted or deleted relative to the sequence of the parent polypeptide. Insertions and deletions of amino acid residues in polypeptides having longer amino acid sequences may be prepared by directed mutagenesis.

The term "polypeptide" includes those having one or more chemical modification relative to another polypeptide, i.e., chemically modified polypeptides. The polypeptide from which a chemically modified polypeptide is derived may be a wildtype protein, a mutant protein or a mutant polypeptide, or polypeptide fragments thereof; an antibody or other polypeptide ligand according to the invention including without limitation single-chain antibodies, bacterial proteins and polypeptide derivatives thereof; or polypeptide ligands prepared according to the disclosure. Preferably, the chemical modification(s) confer(s) or improve(s) desirable attributes of the polypeptide but does not substantially alter or compromise the biological activity thereof. Desirable attributes include but are limited to increased shelf-life; enhanced serum or other in vivo stability; resistance to proteases; and the like. Such modifications include by way of non-limiting example N-terminal acetylation, glycosylation, and biotinylation.

Substitution of unnatural amino acids for natural amino acids in a subsequence of a polypeptide can confer or enhance desirable attributes including biological activity. Such a substitution can, for example, confer resistance to proteolysis by exopeptidases acting on the N-terminus. The synthesis of polypeptides with unnatural amino acids is routine and known in the art.

Different host cells will contain different post-translational modification mechanisms that may provide particular types of post-translational modification of a fusion protein if the amino acid sequences required for such modifications is present in the fusion protein. A large number (~100) of post-translational modifications have been described. One skilled in the art will be able to choose appropriate host cells, and design chimeric genes that encode protein members comprising the amino acid sequence needed for a particular type of modification. Glycosylation is one type of post-translational chemical modification that occurs in many eukaryotic systems, and may influence the activity, stability, pharmacogenetics, immunogenicity and/or antigenicity of proteins.

Another type of post-translation modification is the phosphorylation of a free hydroxyl group of the side chain of one or more Ser, Thr or Tyr residues. Protein kinases catalyze such reactions. Phosphorylation is often reversible due to the action of a protein phosphatase, an enzyme that catalyzes the dephosphorylation of amino acid residues. Differences in the chemical structure of amino terminal residues result from different host cells, each of which may have a different chemical version of the methionine residue encoded by a start codon, and these will result in amino termini with different chemical modifications. For example, many or most bacterial proteins are synthesized with an amino terminal amino acid that is a modified form of methionine, i.e, N-formyl-methionine (fMet). In eukaryotes, acetylation of the initiator methionine residue, or the penultimate residue if the initiator methionine has been removed, typically occurs co- or post-translationally. The acetylation reactions are catalyzed by N-terminal acetyltransferases (NATs, a.k.a. N-alpha-acetyl-transferases), whereas removal of the initiator methionine residue is catalyzed by methionine aminopeptidases (for reviews, see Bradshaw et al., Trends Biochem. Sci. 23:263-267, 1998; and Driessen et al., CRC Crit. Rev. Biochem. 18:281-325, 1985). Amino terminally acetylated proteins are said to be "N-acetylated," "N alpha acetylated" or simply "acetylated."

A polypeptide mimetic ("peptidomimetic") is a molecule that mimics the biological activity of a polypeptide but is no longer peptidic in chemical nature. By strict definition, a peptidomimetic is a molecule that contains no peptide bonds (that is, amide bonds between amino acids). However, the term peptidomimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the polypeptide on which the peptidomimetic is based. As a result of this similar active-site geometry, the peptidomimetic has effects on biological systems that are similar to the biological activity of the polypeptide. There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that are not experienced with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference].

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

By "bind(s) specifically" or "specifically bind(s)" or "attached" or "attaching" is meant the preferential association of a ligand, in whole or part, with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific binding, may be distinguished as mediated through specific recognition of the target molecule. Typically specific binding results in a much stronger association between the delivered molecule and cells bearing the target molecule than between the bound molecule and cells lacking the target molecule. Specific binding typically results in greater than 2 fold, preferably greater than 5 fold, more preferably greater than 10 fold and most preferably greater than 100 fold increase in amount of bound ligand (per unit time) to a cell or tissue bearing the target molecule as compared to a cell or tissue lacking the target molecule or marker.

By "biologically active component" is meant a compound which, in vivo, directly causes or inhibits an increase or decrease in cellular transcription, translation, receptor binding, active or passive transport, cell signaling, signal transduction, cell division, cell differentiation, cell death, cell adhesion, cell movement, cell morphology, metabolism, enzyme activity, apoptosis, protein degradation, protein movement (e.g., secretion), protein stability, or phosphorylation. Biologically active components also comprise diagnostic compositions which allow the foregoing events to be assessed.

A "biologically active component—ligand conjugate" refers to a chimeric molecule comprised of a biologically active component coupled to a targeting moiety, such as an antibody or a scFv, which confers on the conjugate the ability to bind selectively to a target. In the case of a scFv for example, the target is typically a cell bearing an antigen to which the scFv specifically binds.

By "domain" or "substructure" of a protein is meant a portion of a protein, which portion has a defined functionality. Such domains or substructures include catalytic domains of enzymes, regulatory domains of enzymes, cytoplasmic domains of transmembrane proteins, signaling domains, such as src homology domain 2 and domain 3 (known in the art as SH2 and SH3), and the pleckstrin homology domain. Fragments of antibodies which retain antigen recognition, such as Fab, scFv, dsFv, and the like, also can be considered domains or substructures of proteins for purposes of this invention.

By "not substantially bind" is meant that no more than 15% of a ligand which specifically binds to a target molecule is bound to a particular non-target molecule. More preferably, no more than 10% is bound to the non-target molecule, even more preferably less than 5%, and most preferably less than 1%.

The term "physiological conditions" is used herein in two meanings. With reference to culturing cells or the like, it means an extracellular milieu having conditions (e.g., temperature, pH, and osmolarity) which allows for the sustenance or growth of a cell of interest. With reference to the species of secretory component (SC) which is most abundant under such conditions, "physiological conditions" refers to the conditions normally present in the organ of interest or tissue of interest, such as the lumen of the small or large intestine.

By "humanized antibody" is meant an antibody which comprises a non-human amino acid sequence but whose constant region has been altered to reduce immunogenicity in humans.

By "apical surface" is meant that surface of a cell to which intact pIgR is transcytosed to after endocytosis from the basolateral surface. Generally, the apical surface of the cell adjoins a lumen and once pIgR is secreted from the cell surface, the pIgR is cleaved to release the secretory component, leaving a region proximal to the cell (the stalk) attached.

By "basolateral surface" is meant that surface of a cell from which intact pIgR is delivered to after synthesis in the endoplasmic reticulum and passage through the Golgi complex.

By "transcytosed" or "transcytosis" is meant conveyance from one plasma membrane of the cell to another via an intracellular route. Typically, transcytosis occurs from the basolateral to apical or apical to basolateral plasma membrane of the cell. "Retrograde" motion is motion from the apical to the basolateral surfaces of the cell.

By "cell membrane proximal" is meant next to or nearer the cell membrane.

By "extracellular" is meant the region extending outward from the lipid bilayer encompassing a cell.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table 1:

TABLE 1

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table 2 each contain amino acids that are conservative substitutions for one another:

TABLE 2

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *PROTEINS*, W.H. Freeman and Company, New York (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The Polymeric Immunoglobulin Receptor

The nucleic acid and amino acid sequence of the polymeric immunoglobulin receptor has been identified in a variety of taxonomically diverse species. See, Piskurich et al., *Journal of Immunology* 154:1735-1747 (1995). The alignment and sequences of a number of mammalian pIgRs are shown in Mostov, K. E. and Kaetzel, C. "Immunoglobulin transport and the polymeric immunoglobulin receptor," In: *Mucosal Immunology*, P. L. Ogra, et al., (eds.), Academic Press, Inc., New York, pp. 181-211 ($2^{nd}$ ed., 1999) (hereafter, "Mostov and Kaetzel"). The amino acid sequences for the pIgR of for a number of mammalian species have been aligned and set forth in the art. Identification of pIgR from other species can be accomplished by any number of methods well known to those of skill in the art. For example, using published pIgR sequences, a nucleic acid probe to pIgR can be constructed. The probe typically should be derived from a conserved region of pIgR. Hybridization of the probe to a genomic or cDNA library can be used to identify pIgR in an unknown species. It will be understood by the skilled artisan that the nucleic acid sequence of the pIgR probe should generally be that of the species most closely related to the probed species. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, New York.

In an alternative approach, pIgR or peptide fragments thereof (e.g., secretory component) can be used to create antibodies to screen expression libraries. See, e.g., Ferkol et al., *J. Clin. Invest*. 95:493-502 (1995). These and other methods well known to the skilled artisan may be found, for example, in Berger and Kimmel, *Guide to Molecular Cloning Techniques*, Methods in Enzymology volume 152 Academic Press, Inc., San Diego, Calif. (Berger); Sambrook et al. (1989) *Molecular Cloning—A Laboratory Manual* (2nd ed.) Vol. 1-3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Confirmation of the identity of a nucleic acid or protein as encoding pIgR may be had by such approaches as constructing antibodies to the putative pIgR protein and confirming the ability of these antibodies to bind to a protein having the characteristics of pIgR (e.g., being present on the surface of epithelial cells, binding of dimeric IgA or pentameric IgM, etc.).

The nucleic acid and amino acid sequence of the polymeric immunoglobulin receptor has been identified in a variety of taxonomically diverse species. See, Piskurich et al., *Journal of Immunology* 154:1735-1747 (1995). The sequence of human pIgR is set forth, inter alia, in Eiffert et al., Hoppe Seyler's Z. Physiol. Chem. Bd. 365, S.1489-1495 (1984), and in Hughes et al., FEBS Letters 410:443-446 (1997), and further set forth in SWISS-PROT, a curated protein sequence database maintained by the European Molecular Biology Laboratory Data Library, under accession number P01833 (the sequence is publicly available on the World Wide Web by entering "expasy.ch/cgi-bin/" followed by "sprot-search-ac?P01833"). The numbering in SWISS-PROT (see, e.g., SEQ ID NO:1) includes an 18-residue leader sequence; thus, references to particular residues in the SWISS-PROT database are 18 numbers higher than the numbers accorded the same residues by references which do not include the leader sequence (such as Hughes et al. and the Mostov and Kaetzel reference), even though they refer to the same protein. References herein to one or more numbered residues of human pIgR are to the residues as numbered in the SWISS-PROT database. The SWISS-PROT database also reports that an alanine to valine variant has been found at position 580 of the sequence. Ligands that bind to B regions containing this or other similar variants are encompassed within the present invention. Such variants include variants of the sequence set forth in SWISS-PROT so long as they do not destroy the function of the variant pIgR molecule as a receptor for polymeric immunoglobulin and do not destroy the ability of the variant pIgR molecule to internalize and transcytose a ligand bound to it. Assays for determining internalization and transcytosis of a bound ligand are set forth in the Examples.

Methods of alignment of sequences for comparison are well-known in the art. Optimal alignment of sequences for comparison may be conducted by the local homology algorithm of Smith and Waterman (1981) *Adv. Appl. Math*. 2: 482; by the homology alignment algorithm of Needleman and Wunsch (1970) *J. Mol. Biol*. 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237-244 and Higgins and Sharp (1989) *CABIOS* 5: 151-153; Corpet, et al. (1988) *Nucleic Acids Research* 16, 10881-90; Huang, et al. (1992) *Computer Applications in the Biosciences* 8, 155-65, and Pearson, et al. (1994) *Methods in Molecular Biology* 24, 307-31. Alignment is also often performed by inspection and manual alignment. The alignment and sequences of a number of mammalian pIgRs are shown in Mostov, K. E. and Kaetzel, C. "Immunoglobulin transport and the polymeric immunoglobulin receptor," In: *Mucosal Immunology*, P. L. Ogra, et al., (eds.), Academic Press, Inc., New York, pp. 181-211 ($2^{nd}$ ed., 1999).

Identification of pIgR

The nucleic acid and amino acid sequence of the polymeric immunoglobulin receptor has been identified in a variety of taxonomically diverse species. See, Piskurich et al., *Journal of Immunology* 154:1735-1747 (1995). The alignment and sequences of a number of mammalian pIgRs are shown in Mostov, K. E. and Kaetzel, C. "Immunoglobulin transport and the polymeric immunoglobulin receptor," In: *Mucosal Immunology*, P. L. Ogra, et al., (eds.), Academic Press, Inc., New York, pp. 181-211 (2nd ed., 1999) (hereafter, "Mostov and Kaetzel"). The amino acid sequences for the pIgR of six mammalian species are aligned and set forth in FIG. 1. Identification of pIgR from other species can be accomplished by any number of methods well known to those of skill in the art. For example, using published pIgR sequences, a nucleic acid probe to pIgR can be constructed. The probe typically should be derived from a conserved region of pIgR. Hybridization of the probe to a genomic or cDNA library can be used to identify pIgR in an unknown species. It will be understood by the skilled artisan that the nucleic acid sequence of the pIgR probe should generally be that of the species most closely related to the probed species. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, New York.

In an alternative approach, pIgR or peptide fragments thereof (e.g., secretory component) can be used to create antibodies to screen expression libraries. See, e.g., Ferkol et al., *J. Clin. Invest.* 95:493-502 (1995). These and other methods well known to the skilled artisan may be found, for example, in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Confirmation of the identity of a nucleic acid or protein as encoding pIgR may be had by such approaches as constructing antibodies to the putative pIgR protein and confirming the ability of these antibodies to bind to a protein having the characteristics of pIgR (e.g., being present on the surface of epithelial cells, binding of dimeric IgA or pentameric IgM, etc.).

Identification of the Initial SC Cleavage Site

A putative heptapeptide consensus sequence which identifies the cleavage site of pIgR and thereby defines the amino terminus of the stalk has previously been identified. The sequence Phe-Ala-X-Glu, where X is a polar or charged amino acid, was identified as immediately preceding this putative cleavage site. Piskurich et al., *Journal of Immunology* 154:1735-1747 (1995).

It appears now that there is some conflicting evidence regarding the cleavage site and that there may be different cleavage sites depending on the particular species and the particular organ in which the pIgR is expressed. Thus, the C-terminus of the B region may vary according to the particular species of organism under consideration. One of skill can, however, readily determine whether a particular ligand binds to the B region of any particular species of organism. Where the sites of cleavage differ among the organs of a particular organism, the relevant B region for purposes of this invention is preferably that of the animal's intestinal tract. The cleavage liberates the secretory component and defines its initial carboxy terminus. The carboxy terminus of secretory component is then altered by secondary cleavage events (e.g., exopeptidase or endopeptidase activity) to yield secondary carboxy termini.

Mostov and Kaetzel, supra, reviews and summarizes much of the available information regarding SC cleavage. They note that Hughes et al., FEBS Letters 410:443-446 (1997), isolated human colostrum SC from a single individual and showed that the C terminal residue was Arg585. In contrast, earlier work published in German (Eiffert, et al, Hoppe Seyler's Z. Physiol. Chem. Bd. 365, S.1489-1495 (1984), found a "ragged" (i.e. variable C-terminus of SC from human colostrum (pooled from several individuals). The C-termini that they reported were Ala550, Gly551, Ser552, Ala558, and Lys559. (The numbering of the residues in Eiffert et al. is considered by those of skill to be off by one. The numbering of the residues set forth in the text have been corrected to their accepted numbering as set forth in the SWISS-PROT database (see SEQ ID NO:2), and in other sources. For ease of reference, the numbering used by those of skill is used in the text herein. In Eiffert et al., the residues mentioned above were designated Ala449, Gly550, Ser551, Ala557, and Lys558, respectively.) The predominant species ended in Ser552.

It appears that in human mammary gland (at least during the first few days post partum when colostrum is being produced) an initial cleavage occurs at Arg585 or even closer to the C-terminus. Subsequently, secondary cleavages occur to chew the C-terminus back to between Ala550 and Lys559. It thus appears that Eiffert et al were studying SC that had been subject to secondary cleavages, whereas Hughes et al. had studied SC that either had not been subject to secondary cleavage, or at least to less secondary cleavage than Eiffert et al.'s samples. Some of the putative cleavage sites are denoted in FIG. 1 (which is taken from Mostov and Kaetzel) by vertical arrows.

Thus, in the mammary gland, the N terminus of the B region can start, for example, from Lys 559, from the most abundant C-terminus, Ser551, found by Eiffert et al., or from Ala550. In tissues other than mammary gland, there may be additional secondary cleavages, so the B region may extend even further towards the N-terminal region of the protein. This is more likely to occur in the intestinal tract, where the level of proteases is much higher than that present in colostrum. Ahnen et al (J. Clin. Invest 77:1841-1848 (1986)) reported that SC isolated from the lumen of rat intestine had a molecular weight 10,000 to 20,000 Daltons smaller than SC from rat bile. They hypothesized that the SC in the rat intestinal lumen had undergone more secondary cleavage, accounting for the decrease in MW. They did not report the C-terminal residues of any of these forms of SC, so the exact sites of cleavage were not shown. Based on the size of SC isolated from the intestinal lumen by Ahnen et al. though, it appears that the N terminal end of the B region (and, thus, the C terminal end of fully processed free SC) commences at or about the residue marked "Bridge to IgA" in FIG. 1.

The exact N-terminal boundary of the B region is likely to be variable. This is to be expected, as secondary cleavages (especially exoproteases) may leave a ragged end. This merely means that a ligand targeted to the terminal portions of the B region may or may not bind in small amounts to a free SC which still has the target epitope present. In more preferred embodiments, the ligands are targeted to epitopes which are promptly degraded on all or most SC after cleavage and are therefore always within a B region. Any particular ligand can be tested for whether it binds to the B region, to the stalk, or to the major species of SC present in an organ of interest or on a tissue of interest by assays known in the art, including the exemplary assays set forth in the Examples. One Example demonstrates the use of SC from the lumen of the intestines of sacrificed Cynomologous monkeys. SC from the gastrointestinal tract of monkeys and other mammals can further also be obtained by, for example, taking fluid samples from the colon by endoscopy. Samples of human intestinal SC can be obtained directly by such procedures as endoscopy, sigmoidoscopy, or colonoscopy, or by surgical procedures. Similarly, samples from the lung or uterus can be obtained by endoscopy or surgical procedures. Samples from organs such as the vagina and from tissues such as the nasal passages and lacrimal glands can be obtained by swabs and other routine medical procedures. Once obtained, sample can be treated with a "cocktail" of protease inhibitors to prevent further degradation of the pIgR and of any cleaved SC, and to permit determination of the major form of SC present in the sample.

Sequences of pIgR from different species can be aligned, as in FIG. 1. It should be noted that FIG. 1 employs various gaps and insertions to align the sequences of the different species and the numbering used is a "unified" numbering that does not correspond to any one species. The sequence of human pIgR is set forth, inter alia, in Eiffert et al., supra, and in Hughes et al., supra, and further set forth in SWISS-PROT, a curated protein sequence database maintained by the European Molecular Biology Laboratory Data Library, under accession number P01833 (the sequence is set forth herein as FIG. 2 and is publicly available on the World Wide World at, e.g., expasy.ch/cgi-bin/sprot-search-ac?P01833). The numbering in SWISS-PROT includes the 18-residue leader sequence shown in FIG. 1; thus, references to particular residues in the SWISS-PROT database are 18 numbers higher than the numbers accorded the same residues by references which do not include the leader sequence (such as Hughes et al.), even though they refer to the same protein. References below to one or more numbered residues of human pIgR are to the residues as numbered in the SWISS-PROT database.

Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237-244 and Higgins and Sharp (1989) *CABIOS* 5: 151-153; Corpet, et al. (1988) *Nucleic Acids Research* 16, 10881-90; Huang, et al. (1992) *Computer Applications in the Biosciences* 8, 155-65, and Pearson, et al. (1994) *Methods in Molecular Biology* 24, 307-31. Alignment is also often performed by inspection and manual alignment.

In another approach, secretory component can be isolated from fluids in the apical lumen (e.g., vaginal mucus, milk, and bile) or on surfaces proximal to the secreting cells (e.g., nasal mucus, tears) and sequenced by amino acid sequencing methods well known to those of skill such as Edman degradation, or mass spectrometry. Eiffert et al., Hoppe-Seyler's *Z. Physiol. Chem.* 365:1489-1495 (1984). Among the various secondary carboxyl ends defined by secondary cleavage events, the carboxy terminal amino acid adjacent to the cleavage site can be identified.

Identification of the Stalk

The stalk can be identified by a variety of techniques well known to those of skill. For example, cells expressing pIgR can be subjected to proteolytic cleavage, the cleaved product washed away, the cell sonicated, the remaining portion of pIgR immobilized by antibodies generated against the cytoplasmic domain, and the protein then subjected to standard chemical degradation to determine the sequence of the amino acids on the N-terminal side of the transmembrane domain, thereby defining the stalk. Alternatively, the putative stalk region of the species of interest can be immobilized on a support. A library of scFv, such as human scFv, displayed as fusion proteins on filamentous phage, is then screened for phage displaying scFv that bind to the immobilized stalk. After several rounds of enrichment, phage which bind to the stalk can be selected and its binding to the stalk confirmed by ELISA. DNA from phage of interest can then be subcloned into expression vectors to facilitate larger scale production.

In preferred embodiments, the stalk is identified by use of antibodies specific for the first 15-30 amino acids of pIgR extracellular to the transmembrane domain of the species of interest. An exemplary protocol for generating antibodies identifying the stalk region of pIgR is set forth in Example 1. Peptides that correspond to the pIgR stalks of mouse, rat, human, bovine, and rabbit are set forth as SEQ ID NOS:2, 3, 4, 5, and 6 of U.S. Pat. No. 6,042,833. In particular, SEQ ID NO:4 of the '833 patent sets forth the peptide corresponding to the stalk of human pIgR as: Glu-Lys-Ala-Val-Ala-Asp-Thr-Arg-Asp-Gln-Ala-Asp-Gly-Ser-Arg-Ala-Ser-Val-Asp-Ser-Gly-Ser-Ser-Glu-Glu-Gln-Gly-Gly-Ser-Ser-Arg. In preferred embodiments, the ligands of the invention do not substantially bind to an extracellular epitope within the first 33 amino acids that are cell membrane proximal to the initial pIgR cleavage site.

Cells Expressing pIgR

The present invention broadly pertains to eukaryotic cells. The pIgR expressing cell of the present invention is preferably a mammalian cell and more preferably a mammalian epithelial cell that normally secretes IgA. Mammalian cells can be transfected with a nucleic acid encoding pIgR isolated, synthesized or otherwise derived from one or more desired species. Methods of transfecting and expressing genes in mammalian cells are known in the art. Transducing cells with viral vectors can involve, for example, incubating viruses with cells within the viral host range under conditions and concentrations necessary to cause infection. See, e.g., Methods in Enzymology, vol. 185, Academic Press, Inc., San Diego, Calif. (D. V. Goeddel, ed.) (1990) or M. Krieger, Gene Transfer and Expression—A Laboratory Manual, Stockton Press, New York, N.Y., (1990) and the references cited therein.

The culture of cells which can be used in the present invention include cell lines and cultured cells from tissue is well known in the art. Freshney (*Culture of Animal Cells, a Manual of Basic Technique*, Wiley-Liss, New York (3$^{rd}$ ed., 1994)) and the references cited therein provides a general guide to the culture of cells. The nucleic acid sequences encoding pIgR from the desired species may be expressed in a variety of eukaryotic host cells, including yeast, and various higher eukaryotic cells such as the COS, CHO and HeLa cells lines and myeloma cell lines as well as MDCK and human colon carcinoma derived cells such as Caco2. The recombinant protein gene will be operably linked to appropriate expression control sequences for each host. For eukaryotic cells, the control sequences will include a promoter and preferably an enhancer derived, for example, from immunoglobulin genes, SV40, cytomegalovirus, etc., and a polyadenylation sequence, and may include splice donor and acceptor sequences.

Binding Ligands to the pIgR B Region

The specific ligand is not critical to this invention and various ligands may be used. A host of methods for construction and selection of ligands such as nucleic acids, proteins or peptides (collectively, "peptides), or antibodies, or small organic or inorganic molecules (e.g., U.S. Pat. No. 5,143,854; WO 90/15070; WO 92/10092; WO 96/11878) having the desired specific binding characteristics are well known in the art. Preferably, ligands of the present invention will, under physiological conditions, not bind to the stalk and will not substantially bind to the major species of the secretory component of pIgR present in the tissue or organ of interest (for example, the mammalian intestine) under physiological conditions (that is, that the ligand will not bind to a portion of mature SC after completion of the secondary proteolytic cleavages which occur following cleavage of the SC from intact pIgR). Typical physiological conditions vary from tissue to tissue and can also vary with certain disease conditions. For example, some intestinal tract conditions may affect the secretion of proteases and alter somewhat the timing and nature of the secondary proteolytic cleavages affecting the most abundant form of the SC present. However, the most abundant form of the SC present in a particular organ or tissue, such as the intestine, lung, vagina, nose, or lacrimal gland, during particular disease states, and in particular organisms, can be determined easily using the assays taught herein.

In preferred embodiments, the ligand further binds to a portion of the SC and inhibits cleavage of the SC from the pIgR by its binding. Without wishing to be bound by theory, it is believed that binding of a ligand to epitopes close to the initial cleavage site sterically inhibit pIgR cleavage by impeding or even blocking access of protease to the cleavage site. Preferably, the ligand inhibits cleavage by at least one-quarter (25%). In more preferred embodiments, binding of the ligand inhibits SC cleavage by 30 %, 33⅓%, 40%, 50%, 60%, 66%, 70%, 75%, or even higher percentages. In some preferred embodiments, the ligand binds to an epitope present in intact pIgR prior to cleavage but which is not present in the pIgR stalk once cleavage has occurred. Thus, in this group of embodiments, the ligands typically bind to epitopes which span the cleavage site, but do not bind to epitopes present in the stalk after the pIgR is cleaved. Such ligands do not, for example, bind to a peptide consisting of the first 31 amino acids counting from the surface of cell membrane to the pIgR initial cleavage site and, in a further group of embodiments, do not bind to a peptide consisting of the first 33 amino acids counting from the surface of cell membrane to the pIgR initial cleavage site.

Antibodies, including polyclonal, monoclonal, or recombinant single chain Fv antibodies, can be constructed for use as ligands in the present invention. Methods of producing polyclonal and monoclonal antibodies are known to those of skill in the art. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497; See, Huse et al. (1989) *Science* 246: 1275-1281; and Ward, et al. (1989) *Nature* 341: 544-546. Birch and Lennox, *Monoclonal Antibodies: Principles and Applications*, Wiley-Liss, New York, N.Y. (1995).

As noted above, an exemplary protocol for generating antibodies identifying the stalk region of pIgR is set forth in Example 1. The same protocol can be employed to generate antibodies against the B region by substituting peptides selected from the B region of the animal species of interest for the peptides of the stalk region in the Example (FIG. 1 sets forth the amino acid sequences of the pIgR for a number of species). The Examples further set forth a protocol by which polyclonal goat antibodies were generated to peptides generated from a portion of the sequence of rat pIgR (the portion of rat pIgR used comprises the B region and the stalk).

In general, peptides from anywhere within the B region can be used. Typically, such antibodies will be generated by using a peptide sequence selected from about the first 50 amino acid residues adjacent to the primary pIgR cleavage site, on the side distal from the surface of the pIgR-expressing cell. More preferably, the peptide chosen should be selected from about the first 40 amino acid residues and even more preferably from about the first 30 amino acid residues. The length of the particular peptide chosen should be long enough to act by itself as an antigen; shorter peptides should be coupled to a hapten to generate an immunogenic response. While any peptides of the B region can be tested for their ability to raise antibodies specific for the B region, the following are exemplary of peptides from the human sequence which can be used to generate ligands of the invention: Lys487-Arg603; Lys487-Glu607; Lys487-Val611; Lys487-Arg615; Lys487-Ala618; Cys520-Arg603; Cys520-Glu607; Cys520-Val611; Cys520-Arg615; Cys520-Ala618; Lys577-Arg603; Lys577-Glu607; Lys577-Val611; Lys577-Arg615; Lys577-Ala618; Ser574-Arg603; Ser574-Glu607; Ser574-Val611; Ser574-Arg615; Ser574-Ala618; Val560-Arg603; Val560-Glu607; Val560-Val611; Val560-Arg615; Val560-Ala618; Cys544-Arg603; Cys544-Glu607; Cys544-Val611; Cys544-Arg615; and Cys544-Ala618.

Following the nomenclature of the art, the peptides are set forth listing their first and last amino acid residues, in three letter code, and their position in the sequence of the intact molecule (to avoid confusion, amino acid residues of the SC and the stalk are also referred to where appropriate by their position in the sequence of the intact pIgR molecule). As previously noted, the numbering used herein for referring to residues of human pIgR is that set forth in SWISS-PROT under accession number P01833, as shown in FIG. 2. Thus, for example, the first peptide consists of the amino acid residue Lysine at position 487 of the sequence set forth in SWISS-PROT through and including the Arginine at position 603 of the SWISS-PROT sequence.

Alternatively, one can generate antibodies against full-length pIgR and screen the antibodies against peptides of the B region to select those which specifically bind to the B region. A number of techniques are known in the art for such selections. Conveniently, one can perform the selection by immobilizing the peptides of interest on a support, such as a dish or on beads on a column, and running over the surface of the dish or the beads the medium containing the antibodies. Antibodies which do not recognize the B region will not bind, and can be washed off the surfaces, leaving behind those which do bind to the B region peptides. If desired, the antibodies can then be eluted from the surface and screened against peptides of the stalk (such as those of various exemplary species set forth above in the section on identification of the stalk), or of the processed SC, or both, if desired, to ensure that the antibodies are not reactive with the stalk or with the SC. If desired, antibodies passing these screens can then be tested to determine whether they inhibit cleavage of SC, as set forth in the next section.

In a variation on this technique, polyclonal antibodies were raised in goats to a glutathione-S-transferase ("GST")-fusion peptide in which the fusion peptide comprised the rat pIgR B region and stalk. (GST was used not only to permit recombinant expression of the fusion peptide, but also ready purification of the peptide on glutathione columns). Antibodies raised in goats challenged with the fusion peptide were screened against 15-mer peptides immobilized in 96-well microtiter plates and detected by ELISAs, as described in the Examples.

It should be noted that the B region and the stalk are regions without significant sequence identity (see, for example, the sequences of pIgR of six species set forth in FIG. 1). Accordingly, it is not generally necessary to test antibodies which bind to the B region to confirm that they do not also bind to the stalk. Antibodies which bind to epitopes spanning the initial pIgR cleavage site can, however, be tested against peptides of the stalk sequence to confirm that the epitope to which the antibodies bind is one that exists in intact pIgR, but that does not bind to the pIgR stalk following the initial cleavage of pIgR. In preferred embodiments, the ligands of the invention do not bind to an epitope within the first 33 amino acids that are cell membrane proximal to the initial pIgR cleavage site.

Other suitable techniques for antibody or peptide ligand preparation include selection of libraries of recombinant antibodies/peptides in phage or similar vectors. High affinity antibodies and peptides to the B region can be rapidly isolated by using phage display methods to express recombinant single chain Fv (scFv) fragments or peptide ligands on the phage surface. Briefly, genes encoding the surface protein of a phage are altered so as to allow the insertion of an antibody or peptide gene which is expressed as a fusion protein on the surface of the phage that carries the gene. The phage expressing the desired antibody or peptide ligand can be selectively enriched and isolated by virtue of its affinity/avidity for the B region. The DNA encoding the ligand is packaged in the same phage and which allows the gene encoding the ligand to be isolated. A variety of such methods are amply discussed in the literature and well known to the skilled artisan. See, e.g., Winter et al., *Annu. Rev. Immunol.* 12:433-455 (1994); Marks et al., *J. Mol. Biol.* 222:581-597 (1991); Vaughan et al., *Nature Biotechnology* 14:309-314 (1996), U.S. Pat. Nos. 4,642,334; 4,816,397; 4,816,567; 4,704,692; WO 86/01533; WO 88/09344; WO 89/00999; WO 90/02809; WO 90/04036; EP 0 324 162; EP 0 239 400.

In chemical peptide synthesis, a procedure termed "Divide, Couple and Recombine" (DCR) has been used to produce combinatorial peptide libraries. See, Furka et al., *Int. J. Pept. Protein Res.* 37:487-493 (1991) and Houghten et al., *Nature* 354:84-86 (1991). As an alternative to DCR, peptide mixtures have also been made by direct coupling of monomer mixtures. See, Rutter et al., U.S. Pat. No. 5,010,175. The use of such methods to produce mixtures of other linear polymers, such as "peptoids", has been suggested. See, Simon, et al., *Proc. Natl. Acad. Sci. USA* 89:9367-9371 (1992). In oligonucleotide synthesis, "degenerate" or "wobble" mixtures of oligonucleotide products can be made by, for example, delivery of equimolar mixtures of monomers to an oligonucleotide polymer at specific steps during synthesis. See, Atkinson and Smith, in M Gait, ed., "Oligonucleotide Synthesis. A Practical Approach", (IRL Press, Oxford, U.K., 1994), pp 35-81. These methods of synthesizing peptides or oligonucleotides provide large numbers of compounds for testing which, if active, can be readily identified.

The techniques described above can be used to select antibodies which bind to the B region of humans, or of a non-human species of interest which secretes pIgR. As noted in the Introduction, such animals include birds, such as chickens, turkeys, ducks, and ostriches, farm animals, such as cows, pigs, sheep, rabbits, and goats, primates, such as chimpanzees and rhesus monkeys, animals kept at pets, such as cats and dogs, and laboratory animals such as mice and rats. Suitable peptides can be selected by analogy to the peptides set forth above with respect to the human sequence.

Preferably, ligands will be constructed to minimize immunogenicity in the host as, for example, by maximizing the number of autologous (self) sequences present in the ligand. Accordingly, chimeric antibodies having non-xenogenic variable regions are preferred. Particularly preferred are the use of antibodies in which xenogenic portions are excluded, or are essentially limited to the complementarity determining regions as in humanized antibodies.

Assaying for Inhibition of Cleavage

In preferred embodiments, the ligands binding to the B region inhibit cleavage of the SC from intact pIgR. A number of means exist for determining whether a given ligand inhibits pIgR cleavage. In general, one of skill is aware that inhibition of cleavage can be determined by distinguishing free SC from SC still incorporated into pIgR. Thus, any assay which can determine the rate of formation of free SC can potentially be used as an assay for determining the ability of a ligand to inhibit cleavage.

In a simple example, a culture of cells expressing pIgR can be divided into separate samples and the samples cultured under identical conditions. The ligand being tested can then be added to one sample, while an equal amount of the carrier fluid (such as MEM, 5% fetal bovine serum, and the like) is added to the second sample as a control. The supernatant from the two samples can then be run onto affinity columns containing immobilized antibodies to SC or to pIgR, and any bound SC can then be eluted and measured, typically by running a western blot and probing with anti-SC antibodies. A ligand inhibiting cleavage will result in less free SC being present in the test sample compared to the sample to which the carrier alone is added. One can also measure the level of pIgR associated with the pIgR-expressing cells by western blotting. The amount of pIgR associated with the cells will go up as the cleavage of pIgR is inhibited. If desired, the proteins producted by the cells, such as pIgR, can be labeled prior to the study to facilitate detection of the SC captured in the assay. Conveniently, this can be done by providing the cell with cysteine labeled with $^{35}$S. An exemplary assay for determining inhibition of cleavage by yet another method, radioactive pulse-chase labeling is set forth in Example 8. This method is preferred since it provides a more direct measurement of cleavage rate.

The Major Form of SC Present in an Organ or Tissue, and Methods of Assaying for it SC is secreted by cells lining various organs and tissues. For example, SC is secreted by both the small and the large intestine, and the concentration of proteases diminishes in a gradient proceeding from the small to the large intestine. Additionally, some of the fluid bathing the epithelial cells in the intestine may have originated in other tissues and organs which secrete pIgR, such as the salivary glands and the stomach, which also have different protease concentrations. The most abundant form may also vary according to physiological conditions, With respect to the intestine, for example, the most abundant form may vary in part depending on factors such as how much food is in the intestine, the type of food ingested, the presence of diarrhea or constipation, and the like. The most abundant form may also vary in part according to pathological states, such as inflammation or infection of the organ in question. It is contemplated, however, that the most abundant form of the SC throughout the intestinal tract will be that in which the B region has been digested, and indeed, given the concentration of proteases in the intestinal tract, the B region will generally be somewhat larger than it is in organs in which lower amounts or different kinds of proteases are present. The actual form of the SC which is the most abundant in a particular physiological condition or during a particular pathological state can be determined by assays such as those set forth herein. Similarly, the most abundant form of the SC present in other organs or tissues, such as the lung, vagina, nose, sinuses, uterus, and lacrimal glands of the eye will depend on the particular proteases present in the organ and their concentration, but it is contemplated that the most abundant form will be that in which the B region has been digested.

The invention contemplates that compositions of the invention will be tailored to the major species of SC present in the organ of interest. For organs and tissues which can be easily accessed, such as the conjunctiva of the eyes, the passages of the nasal cavity, the vagina, and the anus, the compositions can be applied directly in, for example, eye drops, nasal spray, or vaginal or anal suppositories, respectively. For organs and tissues which are less easily accessible, such as portions of the gastrointestinal tract, the compositions can be administered by cannulation or other methods of direct delivery, or, often more conveniently, by oral administration.

Where oral delivery to the small or large intestine is desired, it may be desirable to protect the compositions from degradation in the mouth and stomach. A number of technologies are known in the art for protecting compositions from acid and premature proteolytic digestion. Such technologies include enteric coatings, encapsulation, polymer coats, hydrogel coats, and capsules. See generally, Gennaro et al., eds., Remington's Pharmaceutical Sciences, 17th ed., Mack Publishing Co., Easton, Pa. (1985).

A number of means exist for determining the major species of SC present in a tissue or organ of interest. If the invention is to be used with respect to a particular animal species, and the most abundant form of SC present in the organ or tissue of that animal species has not previously been identified, it will be desirable to determine it. For tissues or organs which are not readily accessible, samples from non-human animals can be obtained by a number of means, including sacrificing the animals and extracting the contents of their lungs, intestines or other organs of interest. This is likely the most convenient way to obtain samples from most of the animals raised for meat, such as chickens, turkeys, ducks, sheep, pigs, and cows, since they are killed and their internal organs removed in the course of processing. Samples from humans, primates, and other animals can be obtained in the course of surgery or, often more conveniently, by endoscopy. Samples of fluids from organs or tissues which are readily accessible, such as tears, nasal secretions, and vaginal fluids, can be obtained by simple swabs or other routine sampling procedures. If desired, samples can be taken from both healthy animals and those with particular disease conditions to establish the most abundant form of SC present in the particular organ or tissue in normal individuals and in those with particular disease states.

Once a sample of a fluid from a tissue or organ is available, the most abundant form of SC present can be determined by any of a number of means. In general, one of skill will appreciate that the different forms of SC in the sample can be distinguished on the basis of their molecular weight and electrophoretic properties and identified by SC-specific antibodies. Thus, the species of SC can conveniently be distinguished by subjecting the sample to SDS-polyacrylamide gel electrophoresis, followed by western blotting. The identity of the SC species present in the blot can be confirmed by the use of antibodies for portions of the SC expected to be present in all species of SC. For example, the N-terminal portion of the SC would not be expected to be degraded by the proteases which degrade the C-terminal portion (the portion proximal to the site of cleavage from pIgR) and should therefore be present on both freshly cleaved SC and on SC in which the B region has been degraded.

An exemplary assay for determining the major species of SC in an organ of is set forth in Example 7.

Ligand Binding and Testing

Binding (i.e., attachment) of the ligand to the pIgR B region may be at the basolateral or the apical surface. Thus, the ligand can be endocytosed basolaterally or apically, or be subject to apical to basolateral, or basolateral to apical transcytosis. The fate of the ligand, or any element thereof, will vary according to its physico-chemical characteristics. Accordingly, the properties of the ligand may be selected or designed to perform the desired function at the cell surface, within the endosome, or following transcytosis. For example, varying the sensitivity of a ligand to proteolytic or reducing environments can be used to determine the distribution of ligand bound, internalized, or transported across the cell. Where desirable, a ligand may be designed to remain specifically bound to the cell following attachment or transcytosis or, alternatively, to be released into the extracellular milieu on the basolateral side of the cell following apical to basolateral transcytosis. Thus, the properties of any of the various elements of the ligand, including the binding component, biologically active component or linker, may be designed or selected to allow for different degrees of affinity, stability, or activity at different intracellular compartments or surfaces of the cell, as desired.

A. Ex Vivo Testing of Ligand Binding

In vitro binding of the ligand to the pIgR B region may be conveniently assessed by measuring endocytosis or transcytosis of bound ligand in epithelial cells, and particularly those of humans. "Endocytosis" refers generally to the phenomenon of a cell ingesting material, e.g., by phagocytosis or pinocytosis. Receptor-mediated endocytosis provides an efficient means of causing a cell to ingest material which binds to a cell surface receptor. See, Wu and Wu (1987) J. Biol. Chem. 262:4429-4432; Wagner et al. (1990) Proc. Natl. Acad. Sci. USA 87:3410-3414, and EP-A 10388 758. Any number of well known methods for assaying endocytosis may be used to assess binding. For example, binding, transcytosis, and internalization assays are described at length in Breitfeld et al. J. Cell Biol. 109:475-486 (1989).

Apical endocytosis is conveniently measured by binding a ligand such as a Fab fragment of an antibody to the B region at the apical surface of Madin-Darby canine kidney (MDCK) cells at 4° C., warming to 37° C. for brief periods (0-10 min), and cooling the cells back down to 4° C. Methods of pIgR expression in MDCK cells are well known in the art. Breitfeld et al., *Methods in Cell Biology* 32:329-337 (1989). Fab remaining on the surface are removed by stripping at pH 2.3. Intracellular Fab are those that remain cell-associated after the stripping, while surface-bound Fab are those removed by the acid wash. Controls for non-specific sticking include using pre-immune Fab and/or MDCK cells that are not transfected with pIgR.

Transcytosis can be readily assessed by allowing MDCK cells to bind the Fab at the apical surface at 4° C., warming up to 37° C. for 0-240 min, and then measuring the amount of Fab delivered into the basolateral medium. This basolaterally-delivered Fab is compared to the sum of Fab that remains associated with the cells (intracellular or acid-stripped) and the Fab released back into the apical medium. Alternatively, transcytosis can be assessed by continuously exposing cells to the Fab in the apical medium and measuring accumulation of Fab in the basolateral medium. This method avoids cooling the cells, but does not provide the kinetics of transporting a single cohort of ligand. In both methods, degradation of the Fab can be assessed by running aliquots of the transcytosed Fab on SDS-PAGE and probing a Western blot with appropriate antibodies. Non-specific transport (e.g. due to fluid phase endocytosis and transcytosis, or paracellular leakage between cells) can be controlled for by using MDCK cells that are not transfected with the pIgR and/or pre-immune Fab.

B. In Vivo Testing of Ligand Binding

Transcytosis in vivo may conveniently be assessed using pathogen-free experimental animals, such as Sprague-Dawley rats. For example, labeled ligand (e.g., radioiodinated antibody) can be administered orally in any of a variety of formulations which have been developed to deliver pharmaceutical agents to the intestine without digestion in the stomach. Alternatively, the ligands can also be delivered surgically by cannulation of the intestine. An exemplary protocol for such an assay is set forth in the Examples, below. As will be understood by those of skill in the art, a "label" is a composition detectable by spectroscopic, photochemical, biochemical, immunochemical, enzymatic, electromagnetic, radiochemical, or chemical means such as fluorescence, chemifluoresence, or chemiluminescence. Apical to basolateral transcytosis can be readily determined by measuring delivery of the ligand into the circulation as determined by the presence of label. The integrity of the ligand recovered from the circulation can be assessed by analyzing the ligand on SDS-polyacrylamide gel electrophoresis. Similar assays can be employed using eye drops to deliver agents to the conjunctiva or lacrimal glands of the eyes, using nose drops to deliver agents to the mucosal surfaces of the nose or nasal sprays to deliver agents to the sinuses, or using vaginal suppositories or washes to deliver agents to the mucosal surfaces of the vagina.

C. Antibody Production

Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, *Nature* 256:495-497 (1975); and particularly (Chowdhury, P. S., et al., *Mol. Immunol.* 34:9 (1997)), which discusses one method of generating monoclonal antibodies.

To immunize with pIgR-coding DNA, pIgR-coding cDNA is introduced into a plasmid so that transcription of the coding sequence is under the control of a promoter such as the CMV promoter. The plasmid is then injected into an animal, either subcutaneously, intradermally, intraperitoneally, etc. As a result, the pIgR cDNA is transcribed in the animal into mRNA, pIgR is translated from the mRNA, the translated protein undergoes proper post-translational modifications and is expressed on the surface of cells which synthesized pIgR. The animal raises antibodies to pIgR and the sera is monitored for antibody titer.

Optionally, in addition to the coding region and regulatory elements, the plasmid carries an ampicillin resistance (Amp) gene. The Amp gene is known to have immunostimulatory sequences for Th1 responses necessary for increased antibody production (Sato, et al., *Science* 273:352-354 (1996)).

As described above, in preferred embodiments, the monoclonal antibody is a scFv. Methods of making scFv antibodies have been described. See, Huse, et al., supra; Ward, et al. *Nature* 341:544-546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

D. Binding Affinity of Antibodies

Binding affinity for a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a $K_D$ in the lower ranges. $K_D$=[Ab-Ag]/[Ab][Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible non-covalent associations such as electrostatic attraction, Van der Waals forces and hydrogen bonds. This method of defining binding specificity applies to single heavy and/or light chains, CDRs, fusion proteins or fragments of heavy and/or light chains, that are specific for pIgR if they bind pIgR alone or in combination.

The dissociation constant is also described in the art in terms of the constants by which a molecule binds to another (the "$K_{on}$") and dissociates from that molecule (the "$K_{off}$"). As reported herein, the scFv of the invention have surprisingly high rates of retrograde transcytosis and basolateral release compared to all other antibodies tested to date. Without being bound by theory, it appears that this may be due in part to a balance of the $K_{on}$ and $K_{off}$ rates of the antibodies, by which the $K_{on}$ rate is sufficient to permit the antibody to bind to pIgR, but the $K_{off}$ rate is sufficient to permit the release of the antibody at the basolateral surface.

Antibodies to the B Region

A. Antibodies

In one set of preferred embodiments, the ligands of the invention are antibodies which result in surprisingly high rates of retrograde transcytosis of the antibody across pIgR-secreting cells and release on the basolateral surface of these cells. In preferred embodiments, the antibody is a single chain Fv portion of an antibody.

In studies with several antibodies, a version of an anti-B region antibody was developed which has proven useful in monitoring binding and transcytosis. This version of the antibody bears the "FLAG®" peptide (SEQ ID NO:22), a label system commercially available from Sigma (St. Louis, Mo.). Experiments showed that scFvs labeled with the FLAG® peptide (SEQ ID NO:22) and bearing an anti-FLAG® (SEQ ID NO:22) antibody could bind to B region of pIgR, undergo apical to basolateral transcytosis and be released into the basolateral medium. The amino acid sequence of an exemplary scFv labeled with the FLAG® epitope (SEQ ID NO:22), an scFv designated 4AF, is set forth in FIG. 5 (the unlabeled scFv, 4A, is the same sequence, minus the FLAG® epitope (SEQ ID NO:22)). The scFv is labeled with both FLAG® (SEQ ID NO:22) and with an epitope from the myc oncogene. This "FLAG®ged" (SEQ ID NO:22) form of scFv 4A has a pelb sequence to facilitate secretion of the finished protein when produced in *E. coli* (as is well known in the art, different leader sequences would be used to facilitate secretion in other organisms), and a 6-histidine tail to facilitate purification using immobilized metal-ion affinity chromatography ("IMAC"). The unboxed "AAA" residues are part of the Not I site engineered in for cloning. Construction of the scFV is described in the Examples.

In studies with a second scFv, the primer used to add the FLAG® (SEQ ID NO:22) epitope introduced a non-conserved substitution of a valine for a glutamine at a position within the framework region of the scFv. No statistically significant difference was noted between the tagged and the untagged antibody in assays of retrograde trancytosis or basolateral release. This substitution demonstrated that a non-conservative substition in the framework region did not affect the binding and transport properties of the scFv. This is expected since almost all the antigen recognition and binding properties are considered in the art to be localized in the CDRs. See generally, Kuby, J., *Immunology*, 3rd Ed., W.H. Freeman & Co., New York (1997). On the basis of these results, it is expected that conservative substitutions in the framework region would be even less likely to affect ligand internalization into the cell, or transcytosis and release into the basolateral medium. Moreover, conservative substitutions can often also be made in the CDRs without adversely affecting the retrograde transcytosis and release at the basolateral surface of the scFvs. The affect of any substitution or substitutions on these properties can readily be tested by standard assays, such as those set forth in the Examples.

The particular antibodies tested are scFvs. Persons of skill in the art will recognize that other means of making recombinant antibodies are known in the art which permit making antibodies with the favorable properties of the scFvs tested. For example, scFv sequences can be used to produce disulfide stabilized antibodies, wherein the heavy and light chains of the antibody are associated by disulfide bonds rather than a peptide linker. Such variations on the antibodies are expected to work as do the scFv forms, and are contemplated within the scope of the present invention. Formation of scFv and dsFv antibodies are discussed further below.

As noted above, in preferred embodiments of the present invention, the anti-pIgR antibody is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In a particularly preferred embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced. One of skill will realize that conservative variants of the antibodies of the instant invention can be made. Such conservative variants employed in scFv fragments will retain critical amino acid residues necessary for correct folding and stabilizing between the $V_H$ and the $V_L$ regions.

The anti-pIgR antibodies of the invention can be linked to biologically active molecules (sometimes called "effector molecules," or "EM") through the EM carboxyl terminus, the EM amino terminus, through an interior amino acid residue of the EM such as cysteine, or any combination thereof. Similarly, the EM can be linked directly to the heavy or light chains or a framework region of the antibody. Linkage can occur through the antibody's amino or carboxyl termini, or through an interior amino acid residue. Further, multiple EM molecules (e.g., any one of from 2-10) can be linked to the anti-pIgR antibody and/or multiple antibodies (e.g., any one of from 2-5) can be linked to an EM.

In some embodiments of the present invention, the scFv antibody is directly linked to the EM through the light chain or through the heavy chain. Additionally, scFv antibodies can be linked to the EM via its amino or carboxyl terminus. The scFv can, for example, be engineered to contain a cysteine at the amino or the carboxy terminus to permit coupling to a compound through a sulfhydryl-reactive linker.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. No. 4,946,778, U.S. Pat. No. 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length.

In some embodiments, the peptide linker is the sequence is Gly-Gly-Gly-Ser, Gly-Gly-Gly-Ser-Gly-Gly-Gly (SEQ ID NO.:24, optionally, an additional Gly can be on either or both ends), or Gly-Gly-Gly-Gly-Ser (SEQ ID NO.:25) or a concatamer of this sequence, and will preferably comprise 2, 3, 4, 5, or 6 copies of this sequence. It should be noted that glycine is generally preferred in peptide linkers because it is flexible, does not have a side group expected to interfere with the intended biological activity of the linked molecules, and under physiological conditions does not bear a charge. However, it is to be appreciated that some amino acid substitutions within the linker can be made. For example, a valine can be substituted for a glycine.

B. Epitope Binding of Anti-B Region Antibodies

As set forth in the Examples, the epitopes to which phage displaying scFv from a human library bound were mapped using a series of 15-residue peptides. Both human pIgR and rat pIgR sequences were used for mapping. The results of the ELISAs revealed that the scFv bound primarily to regions on the N-terminal side of the major cleavage site. For example, as shown in FIG. 3, scFv 4A bound to the epitope defined by the sequence QDPRLF (SEQ ID NO:10) in human pIgR (residues 600 to 605 of the human sequence as set forth in SWISS-PROT) and to the epitope defined by the sequence LDPRLF in rat pIgR (SEQ ID NO:11) (residues 605-610 of the rat pIgR sequence). Although not tested directly, it appears likely that the "Q" in the human sequence and the "L" in the rat sequence may not be necessary and that the antibody will bind to the epitope defined by the amino acids DPRLF.

As further shown in FIG. 3, the epitope LDPRFL of rat pIgR was also bound by antibody 5D, which also bound to the epitope defined by the sequence KAIQDPRLF (SEQ ID NO:12) of human pIgR. ScFv 2E bound to the epitope defined by the sequence LDPRLFADERI (SEQ ID NO:13) of rat pIgR. ScFv 2H bound to the epitope defined by the sequence DENKANLDPRLF (SEQ ID NO:14). ScFv 1F bound to the epitope defined by the sequence RLFADERI (SEQ ID NO:15). ScFvs 1C, 7H, and 6B all bound to the epitope defined by the sequence LDPRLFADE (SEQ ID NO:16). Since the peptides tested were "staggered" by three residues, the more peptides the antibodies were tested against, the more it was possible to map the precise epitope to which the antibody bound.

C. Immunoassays

The antibodies can be detected and/or quantified using any of a number of well recognized immunological binding assays (see, e.g., U.S. Pat. Nos. 4,366,241; 4,376,110; 4,517, 288; and 4,837,168). For a review of general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., pIgR) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-pIgR antibody. Alternatively, the labeling agent may be a third moiety, such as another antibody, that specifically binds to the antibody/pIgR protein complex.

In one aspect, a competitive assay is contemplated wherein the labeling agent is a second anti-pIgR antibody bearing a label. The two antibodies then compete for binding to the immobilized pIgR. Alternatively, in a non-competitive format, the pIgR antibody lacks a label, but a second antibody specific to antibodies of the species from which the anti-pIgR antibody is derived, e.g., murine, and which binds the anti-pIgR antibody, is labeled. In particular, competitive assays as just described can be used to see if an antibody binds to the same epitope as the scFvs discussed above. Typically, columns are prepared with a pIgR protein or a portion thereof, such as residues 600-605 of the human pIgR sequence, immobilized on the surface. The first column is contacted with a quantity of the antibody being tested (the "test antibody") and is then contacted with a known amount of an scFv which is known to bind to the epitope in question (the "known antibody") has been detectably labeled. The pIgR protein or peptide on the second column is contacted with the same amount of known antibody as used on the first column, but without first being contacted with the known antibody, and the amount of known antibody present on each column is determined. If the amounts of known antibody present on both columns are the same, then the test antibody is considered not to bind to the same epitope as does the known antibody or to inhibit the binding of the known antibody. If the amounts of known antibody bound on the column which was contacted by known antibody but not the test antibody is higher than than the amount of known antibody bound to the column which was first contacted with the test antibody, then the test antibody is considered to bind to the same epitope as does the known antibody or to inhibit the binding of the known antibody to its epitope.

Other proteins, such as Protein A or Protein G, may also be used as the label agent. For example, tests have shown that scFv antibodies of the invention bind Protein A. These proteins are normal constituents of the cell walls of streptococcal bacteria. Other proteins known in the art, such as Protein L, may also be used. These proteins exhibit a strong non-immunogenic reactivity with immunoglobulin constant regions from a variety of species (see, generally Kronval, et al., J. Immunol. 111: 1401-1406 (1973); and Akerstrom, et al., J. Immunol. 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-pIgR antibodies in a sample containing the antibodies generally comprises the steps of contacting the sample with an antibody which specifically reacts, under immunologically reactive conditions, to the pIgR/antibody complex.

Assaying Antibody Transcytosis and Release

Binding (i.e., attachment) of the ligands of the invention to pIgR is typically at the apical surface. Thus, the ligand is typically endocytosed apically and subject to apical to basolateral (retrograde) transcytosis. The fate of the ligand, or any element thereof, will vary according to its physico-chemical characteristics. Accordingly, the properties of the ligand may be selected or designed to perform the desired function following transcytosis. For example, varying the sensitivity of a ligand to proteolytic or reducing environments can be used to determine the distribution of ligand bound, internalized, or transported across the cell. Thus, the properties of any of the various elements of the ligand, including the binding component, biologically active component or linker, may be designed or selected to allow for different degrees of affinity, stability, or activity at different intracellular compartments or surfaces of the cell, as desired.

As noted in the Introduction, the antibodies of the invention bind to pIgR and undergo reverse transcytosis from the apical surface of a pIgR-secreting epithelial cell and are released into the extracellular fluid at the basolateral side of the cell at rates that are at least twice that of the polyclonal antibodies developed by Brietfield et al., and which are at least twice that of all other polyclonal and scFv antibodies tested to date when measured, for instance, in standard assays. An exemplary assay by which transcytosis and release can be measured is set forth in the Examples, below. Studies with radiolabeled scFv tested by this assay have demonstrated that over a twelve hour period, as much as 15% of the starting amount of antibody introduced into an in vitro culture underwent reverse transcytosis and was released into the medium in contact with the basolateral surface of the pIgR-secreting cells in the culture. Tests with an scFv conjugated to a second antibody (in this case, an antibody against a FLAG® peptide (SEQ ID NO:22) expressed in frame with the scFv, as explained in the Examples) following the same assay procedure showed that this complex similarly underwent reverse transcytosis and was released into the medium in contact with the basolateral surface of the pIgR-secreting cells in the culture at rates significantly higher than those reported by Breitfeld et al. for their uncomplexed antibodies.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, a therapeutic agent may be used to ameliorate a symptom or a cause of a disease. Or, compositions of the invention may comprise a diagnostic agent whose such as a radiolabel may be used to visualize circulation or other aspects of a pratitioner's concern.

With the therapeutic agents and antibodies herein provided, one of skill can readily construct a variety of clones containing functionally equivalent nucleic acids, such as nucleic acids which differ in sequence but which encode the antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res*. 12:6159-6168 (1984); and, the solid support method of U.S. Pat. No. 4,458,066. Chemical synthesis produces a-single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding anti-pIgR antibodies can be modified. Modification by site-directed mutagenesis is well known in the art. Nucleic acids encoding anti-pIgR antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-pIgR scFv antibody into a vector which comprises the cDNA encoding a biologically active component (sometimes called an "effector molecule," or "EM"). The insertion is made so that the scFv and the EM are read in frame, that is in one continuous polypeptide which contains a functional Fv region and a functional EM region.

Once the nucleic acids encoding an anti-pIgR antibody of the present invention or a conjugate employing such an antibody are isolated and cloned, one may express the desired protein in recombinantly engineered cells, such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-pIgR antibody, or an immunoconjugate formed using an anit-pIgR antibody) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

In addition to recombinant methods, antibodies and conjugates employing antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

Egress of the Ligand from the Endosome

A number of methods well known to the skilled artisan may be used to transport ligand, or any portion thereof, out of the endosome.

A poly-L-lysine/nucleic acid complex bound to a ligand which binds specifically to the B region can be used for efficient transfection. Methods of complexing nucleic acids to antibodies are known in the art. See, e.g., Ferkol et al., *J. Clin. Invest.*, 92:2394-2400 (1993); and Ferkol et al., *J. Clin. Invest.*, 95:493-502 (1995).

In another approach, poly-L-lysine can be linked, such as by genetic fusion or chemical linkers, to a ligand that binds specifically to the pIgR B region. In turn, this complex can be linked to defective adenovirus. Curiel and co-workers have demonstrated that naked plasmid DNA bound electrostatically to poly-L-lysine or poly-L-lysine-transferrin which has been linked to defective adenovirus mutants can be delivered to cells with transfection efficiencies approaching 90%. The adenovirus-poly-L-lysine-DNA conjugate binds to the normal adenovirus receptor and is subsequently internalized by receptor-mediated endocytosis. This approach has been used to obtain as much as a 1000-fold increase in expression of gene therapy vectors. Herpes viruses have similar properties. Curiel et al. (1991) *Proc Natl Acad Sci USA* 88:8850-8854; Cotten et al. (1992) *Proc Natl Acad Sci USA* 89:6094-6098; Curiel et al. (1992) *Hum Gene Ther* 3:147-154; Wagner et al. (1992) *Proc Natl Acad Sci USA* 89:6099-6103; Michael et al. (1993) *J Biol Chem* 268:6866-6869; Curiel et al. (1992) *Am J Respir Cell Mol Biol* 6:247-252, and Harris et al. (1993) *Am J Respir Cell Mol Biol* 9:441-447); Gao et al. (1993) *Hum. Gene Ther.* 4:17-24; Curiel et al. U.S. patent application Ser. No. 07/768,039.

In yet another approach using influenza virus, a hydrophobic peptide in the hemagglutinin can act as a fusion peptide at low pH to effect fusion of the virus with the membrane of the endosome and delivering the virus into the cytoplasm. This peptide has been used in transferrin/peptide/poly-L-lysine/DNA complexes for gene transfer using the transferrin receptor and substantially improved the efficiency of expression. Wagner et al., *Proc. Natl. Acad. Sci USA* 89:7934-7938 (1992). This peptide can be engineered into a ligand for transport of the ligand, or a portion thereof, out of the endosome.

A further approach may employ ricin A. Ricin A chain is capable of penetrating out of endosome and into the cytosol. Beaumell et al., J. Biol. Chem. 268:23661-23669 (1993). A ligand of the present invention may be linked to ricin A, such as by genetic fusion or chemical linkers.

EXAMPLES

The following examples are offered to illustrate, but not to limit the claimed invention.

Example 1

This Example describes a method of producing and assaying for antibodies and Fab fragments which specifically bind to the rabbit pIgR stalk region. Among other things, such antibodies can be used as negative controls in assays for determining that ligands bind to the B region rather than to the pIgR stalk.

The membrane-spanning segment of the rabbit pIgR begins at the Valine residue at position 630. The sequence of the twenty three extracellular residues of the rabbit pIgR that precede the membrane-spanning segment is: 607-AspProAlaSerGlySerArgAlaSerValAsp AlaSerSerAlaSerGlyGlnSerGlySerAlaLys-629 (SEQ ID NO:7).

Two peptides were synthesized (Immuno-Dynamics, Inc., La Jolla, Calif.) representing the extracellular, membrane proximal 16 and 23 amino acids of pIgR. A C-terminal cysteine was added for conjugation purposes. Peptide sequences (in single letter code) were: DPA SGS RAS VDA SSA SGQ SGS AKC (SEQ ID NO:8) for the primary peptide; and the subsequence peptide: ASV DAS SAS GQS GSA KC (SEQ ID NO:9). Half of each amount of peptide was conjugated to keyhole limpet hemocyanin (KLH) (by Immuno-Dynamics, Inc).

The KLH-conjugated peptides were sent to Lampire Biological Laboratories (Pipersville, Pa.) for production of chicken antibodies in two chickens per peptide. Lampire's standard protocol for chicken immunization was followed by collection of pre-immune eggs and a pre-immune test bleed; intramuscular injection of 2 mg of peptide with Freund's complete suspension at project initiation; intramuscular injection of 0.5 mg of peptide with Freund's incomplete suspension week 1; intramuscular injection of 0.25 mg of peptide with Freund's incomplete suspension week 2; rest week 3; intramuscular injection of 0.25 mg of peptide with Freund's incomplete suspension week 4; rest week 5, and test bleed week 6. Daily egg collection began around week 6 and monthly test bleeds were collected. Eggs were delivered monthly.

Upon arrival, egg yolks were carefully separated from egg whites, and stored at 4° C. in 50-80 mls of basic buffer (0.01M sodium phosphate pH 7.5, 0.1M NaCl, 0.01% azide) per egg yolk until processed for extracting chicken antibody ("IgY"). IgY was extracted from batches of stored egg yolks by a series of PEG precipitations followed by a series of ammonium sulfate precipitations, according to the method of Polson et al. *Immunol Commun.* 9:475 (1980)). Briefly, solid PEG (polyethylene glycol, MW 8000) was added to yolks in basic buffer to 3.5% by weight of PEG to volume of diluted yolk, and stirred at room temperature until dissolved. The solution was centrifuged at 14,000 g for 10 min at 20° C. and decanted through a funnel containing a loose layer of absorbent cotton gauze. More PEG was added to the clear filtrate for a final PEG concentration of 12% to precipitate the IgA. After sedimenting the precipitate by centrifuging at 14,000 g for 10 min at 20° C., the precipitate was dissolved in 60 ml of basic buffer per yolk and an equal volume of 24% PEG in basic buffer was added to reform the precipitate. The precipitate was centrifuged twice more at 14,000 g for 10 min at 20° C. to remove all residual PEG solution. Pellets were dissolved in 30 mls of basic buffer per egg yolk, and the protein was precipitated in 50% saturated $(NH_4)_2SO_4$ by slowly adding an equal volume of saturated $(NH_4)_2SO_4$. and by stirring overnight at 4° C. The precipitate was centrifuged at 14,000 g for 10 min at 4° C. and the pellet was washed in an equal volume of cold 50% $(NH_4)_2SO_4$. The precipitate was centrifuged again at 14,000 g for 10 min at 4° C., dissolved in PBS without calcium or magnesium, pH 7.5, and dialyzed extensively in PBS to remove all $(NH_4)_2SO_4$. Purity of the IgY preparation was confirmed by SDS-PAGE (approx. 90-95%), and quantitation of IgY was estimated by measuring the absorbance at 280 nm and using an extinction coefficient of 1.3.

Affinity purification of IgY from chickens injected with the primary peptide of SEQ ID NO:7 was accomplished by first covalently linking the peptide to SULFOLINK coupling gel (Pierce Chemical Company), which allows binding specifically to sulfhydryl groups such as that on the C-terminal cysteine of the peptide. A 3 ml column was made with 3 mg of peptide according to the product instructions. Briefly, a 3 ml column was equilibrated with 6 column volumes of 50 mM Tris, 5 mM EDTA, pH 8.5, and then 3 mg of the primary peptide SEQ ID NO:7 in 3 ml 50 mM Tris, 5 mM EDTA pH 8.5 were added to the column for mixing at room temperature for 15 min. The column gel and peptide were incubated for another 30 min without mixing. The peptide buffer was drained off the gel and saved for later testing to confirm coupling efficiency using Ellman's reagent (DTNB (5,5'-dithiobis(2-nitrobenzoic acid), Pierce Chemical Company) which detects sulfhydryl groups. The primary peptide SEQ ID NO:7 does not contain any aromatic amino acid groups and could not be detected spectrophotometrically or by standard protein assay techniques, such as by Bradford analysis. Using Ellman's reagent according to the product instructions for comparison of an aliquot of peptide solution before and after binding to the gel, confirmed 100% binding efficiency. The gel column was washed with 3 column volumes of 50 mM Tris, 5 mM EDTA pH 8.5 before blocking nonspecific binding sites with 3 ml of cysteine solution in 50 mM Tris, 5 mM EDTA pH 8.5 for 15 min mixing at room temperature followed by 30 minutes without mixing. The column was drained, and washed with 16 column volumes of 1M NaCl and then with 16 column volumes of degassed 0.05% sodium azide.

IgY was affinity purified on this peptide-linked SULFOLINK gel according to a modified version of Rosol et al. Veterinary Immunology and Immunopathology, 35:321-337, 1993. Once at room temperature, the column was washed with 10 column volumes of PBS. IgY was recycled on the column for 2 hours. The column was then washed with 10 column volumes of PBS followed by 10 column volumes of phosphate buffered saline (PBS) with 0.5M NaCl. Peptide-specific IgY was eluted with 500 mM glycine pH 2.5 and neutralized with 1M Tris pH 9.5. A UV spectrophotometer and graphing apparatus were used to follow the washing and elution of protein off the column. Samples with a signal at OD280 nm were concentrated in a centriprep 30 (Amicon) to a volume of 500-600 μl.

Fab fragments (known in this context as "Yab fragments" since they are derived from IgY) were made from affinity purified IgY incubated with immobilized pepsin (Pierce Chemical Company) according to product instructions and modified from the method of Akita and Nakai. *Journal of Immunological Methods.* 162:155-164, 1993. Pepsin slurry was washed twice with 16 times the volume of 50 mM sodium acetate buffer pH 4.2, and resuspended in twice the volume of sodium acetate buffer. Affinity purified IgY was incubated with the immobilized pepsin at 37° C. and mixed for 5 hours. One molar Tris-HCl pH 8.0 was added to give a final pH of 7.5. The pepsin mixture was centrifuged at 1000 g for 5 min and the supernatant containing the fragments was added to a CENTRICON 10 filter (Amicon) to remove small Fc fragments. Complete cleavage was confirmed by SDS-PAGE.

Chicken serum from successive test bleeds and IgY extracted from batches of pooled egg yolks were tested by ELISA to confirm recognition of the peptide. Affinity purified IgY and Fab' fragments ("Yab'") were tested for their ability to recognize intact pIgR by western blot. Cell lysates were made from Madin-Darby canine kidney (MDCK) cells and MDCK cells transfected with rabbit pIgR ("pWe"), according to the method of Breitfeld et al. (*Methods in Cell Biology* 32:329-337 (1989)) using 10% NP40 lysis buffer containing 1 µg/ml of protease inhibitors and phenylmethylsulfonyl fluoride (PMSF). Cell lysates were run on a 10% gel under reducing conditions and transferred onto a PVDF (polyvinyldifluoride) membrane (Millipore, Bedford, Mass.). A mouse monoclonal antibody to the cytoplasmic portion of pIgR, SC166 (Solari et al., *Cell*, 36:61-71 (1984)), was used as a positive control antibody, and IgY isolated from pre-Immune yolks was used as a negative control. HRP-conjugated rabbit anti-chicken IgY (Jackson Immunochemicals) and HRP-conjugated rabbit anti-mouse (Biorad) were used as secondary antibodies. IgY from a chicken injected with the primary peptide and IgY from a chicken injected with the subsequence peptide recognized intact pIgR, but IgY from one of the chickens injected with the subsequence antibody did not. Immunofluorescence studies of IgY and Fab fragments (from chickens injected with the primary peptide) with MDCK and pWe cells grown on coverslips, fixed with 4% paraformaldehyde and permeabilized with saponin showed more specific staining of the pIgR-transfected cells (FITC-conjugated rabbit anti-chicken and anti-mouse antibodies obtained from Jackson Immunochemicals). A cell ELISA (modified from M Hahne et al., *Journal of Cell Biology*. 121:655-64, 1993) on fixed and permeabilized cells showed Fab fragment staining 5-fold greater with pWe cells than MDCK cells. These data demonstrate that we successfully raised polyclonal antibodies against the rabbit pIgR stalk peptide and that they recognize intact pIgR.

Example 2

Antibodies directed to desired portions of the pIgR B region can be generated by using peptides of the B region following art recognized techniques, such as those set forth in the preceding Example. Suitable peptides of portions of the B region can be selected from, for example, the sequences shown in FIG. 1. With reference to FIG. 2, suitable examples include: Lys577-Arg603; Lys577-Glu607; Ser574-Arg603; Ser574-Glu607; Val560-Arg603; Val560-Glu607; Cys544-Arg603; and, Cys544-Glu607. Antibodies raised against these or other peptides are then tested against the most abundant form of SC present in the intestine of the animal species of interest; any antibodies that bind to that form of SC are not within the scope of the ligands of the present invention.

Example 3

This Example describes selection of human recombinant single chain variable region fragment (scFv) antibodies by phage display.

Selection of scFv by phage display requires a soluble biotinylated antigen or antigen immobilized on a solid support. Because scFv selected by phage display tend to be low affinity binders and because the soluble antigen may allow selection of higher affinity scFv (R Schier et al., *J. Mol. Biol*. 255:28-43, 1996), the selection approach with soluble antigen is chosen. The pIgR B region peptide corresponding to 23 amino acids of the putative B region of the rabbit pIgR is conjugated to biotin via the sulfhydryl group of the cysteine residue using biotin-BMCC ((1-Biotinamido-4-(4'[maleimidomethyl]cyclohexane-carboxamido)butane) (Pierce Chemical Company, Rockford, Ill.) based on the method described in the product instructions. To ensure that the peptide does not dimerize via the sulfhydryl groups, the peptide is first reduced with 1% sodium borohydride in 0.1M Tris, 5 mM EDTA pH 8.0. The pH of the solution is lowered to pH 5 by adding 1N HCl. Once the solution finishes fizzing, 1M Tris is added back to reach pH 7.0. A 8.5 mM biotin-BMCC solution is prepared by dissolving the biotinylation reagent in DMSO. A 5-fold molar excess of biotin-BMCC is added to the reduced peptide and incubated overnight at 4° C. The biotinylated peptide is separated from free biotin by HPLC with a C18 column with a gradient ranging from 10 to 50% CH3CN over 30 min, with UV detection at 215 nm. Mass spectrometry by electrospray and LSIMS (liquid secondary ion mass spectrometry) identifies the correct peak corresponding to the biotinylated peptide.

The biotinylated primary peptide is incubated with a phage library encoding a large number of different human scFv (approx. $10^{10}$). This phage library is prepared as previously described (Marks et al., *J. Mol. Biol*. 222:581-97, 1991; Marks et al., *Bio/Technology* 10;779-783, 1992; Marks et al., *Bio/Technology* 11:1145-1149, 1993; Griffiths et al., *EMBO J*. 12:725-734, 1993). A total of four rounds of selection, phagemid rescue and expansion in *Escherichia coli* suppressor strain TG-1 are performed as described in Marks et al. (*J. Mol. Biol*. 222:581-97, 1991) with the following modifications. The phage library used is known to contain several streptavidin binders, so the first three rounds of selection include a preclearing step with two 30 min incubations of the phage with streptavidin agarose (Sigma). The phage are then incubated with 5 µg of biotinylated primary peptide for 1 hour. To bind the biotinylated peptide with the attached phage, the peptide-phage solution is incubated with avidin magnetic beads on the first and third rounds for 15 and 5 minutes, respectively, and with streptavidin magnetic beads on the second and fourth rounds for 10 and 5 minutes, respectively. Rescued phage from the fourth round of selection are infected into *Escherichia coli* non-suppressor strain HB2151, and individual phagemid clones are induced to produce soluble scFv fragments with IPTG as described in Marks et al. (*J. Mol. Biol*. 222:581-97, ((1991)).

Bacterial supernatants from the individual clones are analyzed for expression of soluble scFv fragments in a dot blot assay and for binding to biotinylated primary peptide in an ELISA assay (Finnern et al., *Clin. Exp. Immunol*. 102:566-574, 1995). The ELISA assay, however, is modified in the following manner: 96-well microwell plates (Immulon-4) are coated with avidin (10 µg/ml in phosphate buffered saline (PBS)) overnight at 4° C., washed 3 times with PBS, blocked with 2% milk in PBS and bound with biotinylated primary peptide (5 µg/ml in PBS). TMB (3,3',5,5' tetramethylbenzidine) solution (Kirkegaard and Perry) is used as substrate (100 µl/well), and the reaction is stopped with 0.18M $H_2SO_4$ before reading the color reaction in an ELISA reader at a wavelength of 450 nm. Dot blot analysis shows that 66% of the 96 selected colonies of HB2151 infected with phage rescued from the fourth round of selection produces scFv. ELISA assay shows that 43 of the 96 colonies produces scFv that binds to the peptide.

The diversity of all positive clones is determined by PCR screening. The scFv insert of the heavy and light chain is first amplified with the primers LMB3 and fd-Seq1 (Marks et al., *J. Mol. Biol*. 222:581-97, 1991), and then digested with the restriction enzyme BstN1. Clones with different DNA fingerprint patterns are sequenced using a SequiTherm Long-Read cycle sequencing kit (Epicentre Technologies) and a Licor machine. Five unique sequences are identified.

To obtain large amounts of purified scFv for further characterization and use, the five unique scFv are subcloned into the expression vector pUC119 Sfi-NotmycHis, which adds a hexa-histidine tag at the C-terminal end of the scFv (Schier et al., *J. Mol. Biol.*, 255:28-43, 1996).

Example 4

This Example describes targeting of the wildtype cystic fibrosis transconductance regulator (CFTR) gene into mammalian cells expressing pIgR using a variation of the methods disclosed in Ferkol et al., *J. Clin. Invest.*, 92:2394-2400 (1993); and Ferkol et al., *J. Clin. Invest.*, 95:493-502 (1995), each of which is incorporated herein by reference.

An Fab fragment reactive to the B region of pIgR is made and purified by techniques such as that disclosed in Example 1 (but using a B region peptide rather than the pIgR stalk peptide discussed therein). The Fab is linked to poly (L-lysine) (MW 20,000 Daltons) using the heterobifunctional crosslinking reagent N-succinimidyl 3-(2-pyridyldithio)propionate (SPDP) according to the method of Ferkol et al. (1993).

A plasmid comprising the CFTR gene is ligated to a cytomegalovirus early promoter and inserted into the vector pCB6. Thomas et al., *J. Biol. Chem.*, 268:3313-3320 (1993). Complexes of Fab-polylysine-DNA are made by combining plasmid DNA with the Fab-polylysine in 3M NaCl.

The complex is introduced by dissolving it in 0.1 ml of phosphate buffered saline, and placing it into the nares of pathogen-free Sprague-Dawley rats (250-300 grams) lightly anesthetized with Metofane inhalant anesthesia. A micropipet will be used to apply 100 µL of the plasmid in PBS directly into the nares of rats that are manually restrained in the supine position. Rats will be held in this position until the solution has been inhaled. This technique has been shown to result in effective application of the sample onto the nasal mucosa. Shahin et al., *Infection and Immunity* 60:1482-1488 (1992); Gizurarson et al., *Vaccine* 10:101-106 (1992). Transcription of the transfected gene is assayed by immunofluorescence assay of production of the CFTR protein.

Example 5

This Example describes a means of in vivo targeting of exogenous proteins into cells expressing pIgR.

An efficient method to allow egress of proteins from endosomes will employ the protein-Fab complex coupled to adenovirus. This method has been used with a number of receptor systems resulting in as much as a 1000-fold increase in expression. Curiel et al., *J. Respir. Cell Mol. Biol.* 6:247-252 (1992), Curiel et al., *Proc. Natl. Acad. Sci. USA* 88:8850-8854 (1991), Gao et al., *Hum. Gene Ther.* 4:17-24 (1993), each of which is incorporated herein by reference. Coupling is accomplished by biotinylation of the adenovirus and the Fab/poly-lysine followed by cross-linking with avidin. The resultant complex is administered as in the preceding Examples.

Example 6

This Example describes transcytosis of antibodies which specifically bind to the B region, from the apical to basolateral membrane of a MDCK (Madin Darby canine kidney) cell comprising pIgR.

Fab fragments reactive to pIgR are made as described in the preceding Examples. Anti-pIgR B region Fab fragments are radio-iodinated by the iodine monochloride method of Goldstein et al. (*Meth. Enzymol.* 96:241-249, 1983). Radio-iodinated IgA is used as a control ligand. Radio-iodinated Fab fragments or IgA ($10^7$ cpm in 100 µl/well) are added to the apical surface of MDCK and pWe cells grown in a polarized manner for 4 days on 12 mm diameter, 0.4 µm pore size cell culture inserts (Transwells, Costar). Breitfeld et al., *Methods in Cell Biology* 32:329-337 (1989). Radio-labeled Fab fragments are added to cells with and without a 2 h preincubation with the protease inhibitor, leupeptin, 50 µl/ml. After 20 min of apical uptake at 37° C., unbound radio-labeled ligand is washed with MEM (minimal essential medium)/BSA (bovine serum albumen) three times quickly, one 5 min wash and two more quick washes. The apical and basolateral media are collected and changed at 7, 15, 30, 60 and 120 min time points for quantitation in a gamma counter (Beckman Instruments, Palo Alto, Calif.). Cell culture inserts are cut out at 120 min for quantitation in a gamma counter and to calculate the total initial uptake of radioactivity. The background uptake by MDCK cells are subtracted from that by pWe cells to calculate specific recycling and transcytosis of the radiolabeled ligands.

Example 7

This Example sets forth an assay for demonstrating that a ligand binds to the B region of the pIgR, such that the ligand does not bind to a major species of SC present after proteolytic cleavage of the pIgR and does not bind to the stalk of the pIgR.

The principle of the assay is immunoblotting ("western blotting") of pIgR and various fragments of pIgR. The pIgR and its various fragments are first separated by SDS-PAGE, then blotted onto a membrane. The membrane is probed with the test ligand or control antibodies. The membrane is then probed with a secondary antibody which binds to the primary antibody. The membrane is then "developed" with a visualization system, such as the Enhanced Chemiluminescence System, "ECL Plus" kit from Amersham (Amersham Pharmacia Biotech, Piscataway, N.J.)), and the lumninescent light signal is detected by exposing the blot to photographic light. This indicates which fragments of the pIgR do or do not react with the test ligand.

A. Expression of pIgR in Madin-Darby Canine Kidney (MDCK) Cells

A variety of methods have been used to express cloned cDNAs in MDCK cells, both transiently and in stable cell lines. Conveniently, the retroviral pWE vector may be used, although pDOL vector (Korman et al., Proc Natl Acad Sci USA 84(8):2150-4 (1987) may also be used. In the pWE vector, the gene of interest (cloned into the BamHI site) is driven by an internal chicken beta actin promoter. The neomycin-resistance gene is driven by the viral LTR. BglII linkers are added to the pIgR cDNA. This linked DNA can then be inserted into the BamHI site. Once a suitable construct has been made, plasmid DNA is purified by at least one round of CsCl centrifugation. The psiAM packaging cells can be obtained from Richard Mulligan (Cone and Mulligan, Proc Natl Acad Sci USA 81(20):6349-53 (1984)). Cells are maintained in Dulbecco's minimal essential medium (DME) with 10% calf serum (not fetal bovine serum), 100 units/ml penicillin, and 100 µg/ml streptomycin in 5% $CO_2$. Cells are passaged with trypsin-EDTA every 4-7 days. For transfection, a confluent 10-cm dish is divided 1:10 12-24 hours before use, so that cells are ~20% confluent when transfected.

Plasmid DNA, 10 µg in a volume of 5-20 µl is added to 0.5 ml of sterile HBS in a clear plastic tube. (HBS is prepared by combining 4 g NaCl, 0.185 g KCl, 0.05 g $Na_2HPO_4$, 0.5 g dextrose, 2.5 g HEPES in ~450 ml H$_2$0. The pH is adjusted to exactly 7.05 with NaOH. After bringing the volume to 500 ml, the solution is filter-sterilized.) Then, 32 µl of sterile 2 M CaCl$_2$ are added and the tube gently flicked for 20 seconds. The tube is kept at room temperature for 45 minutes to allow a very faint, hazy precipitate to form. The medium is removed from a 10-cm plate of psiAM cells, and the DNA solution is added to the center of the plate. After 10 minutes at room temperature, the plate is gently rocked. After 10 additional minutes, 10 ml of medium are added and the plate placed in the 37° C. CO$_2$ incubator for 4 hours. The medium is removed and 3 ml of a sterile mixture of 85% HBS-15% glycerol are added at room temperature. This is removed after 3.5 minutes and the dish gently washed three times with 10 ml of medium. Finally, 5 ml of medium are added and the dish placed at 37° C. for 18 hours. All necessary biosafety precautions must be observed, and gloves should be worn when handling the virus.

After 18 hours the medium, containing transiently produced virus, is removed. Polybrene (Sigma Chemical Co., St. Louis, Mo.) is added to a final concentration of 8 µg/ml. (A polybrene stock of 0.8 mg/ml is prepared in H$_2$O, filter-sterilized, and kept at −20° C.) The virus stock can be frozen at −80° C., although each freeze-thaw cycle decreases the titer somewhat. The titer obtained varies from 10 to 1000 colony-forming units per ml. Titer is determined by infecting the appropriate cells (in this case MDCK), and counting the number of neomycin-resistant colonies that result. There is considerable batch-to-batch variability in the concentration of the neomycin analog, G418, necessary to use with MDCK cells. G418, obtained from Gibco, is dissolved at 100 mg/ml in 0.2 M HEPES-NaOH (pH 7.9), sterile-filtered, and stored at −20° C. G418 shows slow deterioration over several years of storage. It is necessary to determine the optimal concentration of G418 for each batch of drug. MDCK cells are maintained in MEM with 5% fetal bovine serum (FBS), penicillin, and streptomycin, in 5% CO$_2$. (Calf serum can be used, but fetal serum is preferred because it lacks IgA). A confluent 10-cm plate is split 1:10 into several 10-cm dishes. Various amounts of G418 are added to give 0.1-1 mg/ml final concentration. The media and drugs are changed after 7 days. The concentration of drug that kills all cells after 14 days should be used.

A 60-cm dish of strain II MDCK cells that is roughly 10% confluent is infected. Then, 1-2 ml of transiently produced virus are added to the dish. After 3 hours, 5 ml of medium are added. In 3 days the cells should be confluent. Cells are trypsinized and taken up in 6.5 ml of medium. To a series of six 10-cm dishes, we add 0.1, 0.2, 0.4, 0.8, 1.6, or 3.2 ml of cells. Medium is added to a final volume of 10 ml, and G418 is added. After 7 days, the media and drug are replaced. After 14 days, medium can be replaced without adding G418. Colonies are visible after 10-14 days, and are picked around day 18-25. Colonies should be picked from a plate containing a few well-separated colonies. Circle the desired colonies with a marker on the bottom outside of the plate. Remove all the medium from the plate. Suck the area around each colony dry with a Pasteur pipet and suction hose, using a separate pipet for each colony. Using sterile forceps, an 8-mm glass cloning ring (Bellco) is dipped in autoclaved Vaseline and then placed firmly over the colony. Then, 75 µl of concentrated tryspin-EDTA (0.5% trypsin 5 mM EDTA) are added. The plate is incubated at 37° C. for 5-10 minutes. Cells are monitored by phase-contrast microscopy. When the cells have rounded up, 75 µl of medium are added to each ring. Using a P-200 Rainin Pipetman® (Rainin Instrument Co., Inc., Emeryville, Calif.) and a sterile yellow tip, the cells are pipeted up and down a few times in the ring. Cells are then transferred. Generally, 80-90% of the cells are put into a 35-mm dish for screening and the balance into a 25-cm$^2$ flask as a reserve. The cells are usually screened by metabolic labeling and immunoprecipitation, which is described below. Usually six clones are selected and screened for a given construct.

B. Screening of Clones and Immunoprecipitation

For screening clones, 35-mm dishes of cells are labeled. When cells are confluent or nearly confluent, the medium is removed and the monolayer rinsed with PBS. One-half to 0.6 ml of labeling medium containing 2-3 micro of [$^{35}$S]cysteine (Amersham, ~700-1100 Ci/mmol, 10-15 mCi/ml) is added. Labeling medium is DME formulated without cysteine and supplemented with 5% FBS (dialyzed against 0.15 M NaCl) and 20 mM HEPES-Na, pH 7.3. The monolayer is labeled for 1-2 hours, and the plates are gently rocked every 15 minutes to keep the cells covered. To harvest the cells, the labeling medium is removed. After this, 0.5 ml of SDS lysis buffer (0.5% SDS, 150 mM NaCl, 5 mM EDTA, 100 units/ml Trasylol® (Bayer Corp., Pittsburgh, Pa.), 20 mM triethanolamine-HCl, pH 8.1) is added, and the cells are scraped off the dish with a small, flat, flexible, rubber spatula. The cell lysate is transferred to a 1.5-ml tube and boiled for 2-5 minutes. After cooling at room temperature for at least 15 minutes, the cells are sonicated. Conveniently, a Branson Sonifier® sonicator (Branson Ultrasonics Corp., Danbury, Conn.) with a cup horn attachment may be used. The tube is sonicated at full power for two 30-second bursts, with intervening cooling period. Then, 0.5 ml of 2.5% Triton dilution buffer (2.5% Triton X-100, 100 mM NaCl, 5 mM EDTA, 100 units/ml Trasylol, 0.1% NaN$_3$, 50 mM triethanolamine-HCl, pH 8.6) is added, along with 30 µl of a 50% slurry of Sepharose CL-2B. The tube is mixed by inverting several times. The tube is centrifuged for 5 minutes in a microfuge, and the supernatant is transferred to a new tube. If any particulate material or "globs" of DNA are observed, a second preadsorption with Sepharose can be performed. Antibody to SC is added to the supernatant. Generally we use 2 µl of a 1:10 dilution of whole serum.

Immunoprecipitation is performed by placing the tubes on a gently rotating mixer for at least 90 minutes at room temperature, or overnight at 4° C. Twenty microliters of a 15% slurry of protein A-Sepharose (Pharmacia) are added and the tubes mixed for an additional 30 minutes. Beads are washed by brief (5 seconds) centrifugation, and resuspending in 1.4 ml of wash buffer. The beads are washed are four times with mixed micelle buffer and once with final wash buffer. The protein A-Sepharose beads are sucked dry with a 50 µl Hamilton syringe. Then, SDS-gel sample buffer is added directly to the beads, and the samples are boiled. The samples are analyzed on 10% polyacrylamide SDS gels. The gels are then dried and the distribution of radioactivity determined with a Molecular Dynamics, Inc. Storm® Phosphorimager.

The software included with the Molecular Dynamics Phosphorimager is used to calculate the amount of radioactivity associated with each band.

C. Preparation of SC-Containing Extract from MDCK Cells Expressing pIgR.

MDCK cells expressing pIgR (human, rat, rabbit, etc) can be used. Extracts can be made from cells grown in tissue culture dishes or on permeable supports, such as Corning Costar Transwell membranes. For SC harvest, 1 ml of the apical media is collected into a 1.5 ml tube and SDS is added to 0.5%. The sample is boiled for 5 minutes, followed by addition of 0.5 ml of 5% triton dilution buffer (5% Triton X-100, 100 mM NaCl, 5 mM EDTA, 100 units/ml Trasylol, 0.1% NaN$_3$, 50 mM triethanolamine-HCl, pH 8.6). Then 50

μl of a 50% slurry of Sepharose CL-2B is added, the tube is shaken, and centrifuged at 12,000×g. Antibody to SC is added to the supernatant. Generally, 2 μl of a 1:10 dilution of whole serum is used. Immunoprecipitation is performed by placing the tubes on a gently rotating mixer for at least 90 minutes at room temperature, or overnight at 4° C. Twenty microliters of a 15% slurry of protein A-Sepharose (Pharmacia) are added and the tubes mixed for an additional 30 minutes. Beads are washed by brief (5 seconds) centrifugation, and resuspended in 1.4 ml of wash buffer. Four washes are performed with mixed micelle buffer (20 mM Triethanolamine pH 8.6, 150 mM NaCl, 5 mM EDTA, 5% sucrose, 1% Triton X-100, 0.02% SDS, 10 Units/ml aprotinin, 0.02% sodium azide) and one with final wash buffer (20 mM Triethanolamine pH 8.6, 150 mM NaCl, 5 mM EDTA, 5% sucrose, 10 Units/ml aprotinin, 0.02% sodium azide). The protein A-Sepharose beads are sucked dry with a 50 μl Hamilton syringe. Then, SDS-gel sample buffer is added directly to the beads, and the samples are boiled and subjected to western blot analysis as described below.

D. Preparation of SC-Containing Extract from the Lumen of Cynomologous Monkey Intestine Rinse the lumen of freshly harvested monkey intestine (10 cm segment) into a dish or other container with 3 ml PBS. To the lumenal contents rinsed into the dish or other container, add the following protease inhibitors: 5 μg/ml pepstatin, 10 μg/ml chymostatin, 5 μg/ml leupeptin, 10 μg/ml antipain, 500 μM benzamidine, 0.01 U/ml aprotinin (trasylol, Bayer), and 1 mM PMSF. Add EDTA to a final concentration of 1 mM. Add SDS to a final concentration of 2%. Boil the sample for 5 minutes. Centrifuge at 12,000 g (full speed in a table top microcentrifuge) for 10 minutes at room temperature. Transfer the supernatant to a new tube. Vortex shake the sample for 5 minutes.

Add 1/10 volume of a 50% slurry of CL-2B. Mix by inverting 5 times, then centrifuge at 12,000 g for 5 minutes at room temp. Transfer the supernatant to a new tube. Repeat the procedure in this paragraph once. Optionally, the supernatant can be subjected to immunoprecipitation with an appropriate antibody to concentrate the sample.

To the sample add an equal volume of 2× Laemmli SDS gel sample buffer containing 100 mM DTT. Boil 3 minutes and load 10 μL on a 10% polyacrylamide gel (Laemmli). Electrophorese until the bromophenol blue is ~1 cm from the bottom.

E. Production of Antibody Against Secretory Component

Secretory component (SC) is a large proteolytic fragment of the pIgR and is easily purified from rabbit bile, rat bile, or bile from other species of interest. Rabbit bile can be purchased from Pel Freez Biologicals, Rogers, Ariz. Rat bile can be obtained by canulation of the bile duct of anesthetized rats. Phenylmethylsulfonyl fluoride (PMSF) is added to 1 mM, and the bile is dialyzed against three 12-hour changes of 100 volumes 0.15 M NaCl. About 1 ml of bile is loaded onto each of six preparative sodium dodecyl sulfate (SDS)-7% polyacrylamide gels (20×20×0.15 cm) using the Laemlli system. No reducing agent is used. As a molecular-weight standard, 1 microliter of whole serum can be run in a side lane. The gel is stained with Coomassie blue. The smeary complex of bands running slightly slower than serum albumin is SC and is excised. The gel slices are lyophilized and ground with a mortar and pestle. We have found that guinea pigs produce excellent antibodies against this preparation of SC, and the antibodies bind well to protein A. The animals are injected with 50 mg of ground gel every 3 weeks for six injections, using Ribi adjuvant (Ribi Immunochem Research, Inc., Hamilton, Mont.). Animals are bled 7-10 days after each of the last three injections. Whole serum can be used for immunoprecipitation F. Modified Rapid Western Blot Procedure:

Transfer the gels from steps C and D, above, to PVDF according to Millipore instructions for 1 hour (Millipore Corp., Bedford, Mass.). Transfer buffer: 25 mM Tris, 192 mM glycine, 10% (v/v) methanol. After transfer, dip the blot in methanol for 10 sec. then air dry for 20 minutes. Incubate blot for 1 hour with primary (Test) antibody in Ab dilution buffer (PBS containing 0.05% Tween 20 and 1% non-fat milk). Wash 3 times 10-60 seconds each with PBS. Incubate 30 minutes with appropriate secondary antibody in Ab dilution buffer at 1/10,000-1/20,000 or empirically determined dilution.

Wash as before. Develop with chemiluminescent substrate (Enhanced Chemiluminescence, "ECL", kit from Amersham (Amersham Pharmacia Biotech, Piscataway, N.J.)) and expose to appropriate film.

As a reference, all forms of pIgR SC can be visualized with a polyclonal anti-SC antibody. Sheep anti-SC antibody works for most primate species, including human.

G. Interpretation:

Duplicate gels should be run, with the following samples run side by side on each of the gels to facilitate comparison:
1. Intact pIgR from pIgR-expressing MDCK cells.
2. SC from apical medium of pIgR-expressing MDCK cells.
3. SC from monkey intestinal lumen.

The gels should then be blotted in a western blot as described above, with incubation and development steps as described in the previous section. One gel is probed with a sheep anti-SC antibody which will react with all forms of pIgR and SC in all three samples. The other duplicate gel is probed with the test ligand to the B region.

A ligand binding to the B region but not to the stalk and not to the major species of the SC present in a mammalian intestine will react with intact pIgR and with SC from the apical medium of pIgR expressing MDCK cells. This ligand will not react with the major form of SC present in the monkey intestinal lumen.

Example 8

This Example sets forth an exemplary assay for determining whether a ligand inhibits the cleavage of pIgR.

The principle of this assay is to metabolically pulse label the pIgR with radioactive amino acids. In a pulse-chase experiment, the cleavage of the pIgR to SC and its release into the apical medium overlying a MDCK cell monolayer is then followed. The rate of cleavage to SC and release is compared in the presence or absence of a ligand that may inhibit cleavage; if the rate of cleavage is decreased in the presence of the ligand, it is deemed to inhibit cleavage.

A. Production of Antibody Against Secretory Component

Antibody binding to SC is produced following the procedure set forth in part C of the preceding Example.

B. Expression of pIgR in Madin-Darby Canine Kidney (MDCK) Cells

Expression of pIgR in MDCK cells is performed as in the previous Example.

C. Screening of Clones and Immunoprecipitation

Screening of clones and immunoprecipitation are performed as described in section B of the preceding Example.

D. Growing MDCK Cells on Filters.

Growth of MDCK cells on filters leads to increased cell polarity and allows separate access to the apical and basolateral surfaces. In preferred embodiments, the filters are 12 mm diameter, 0.4 micron pore size polycarbonate Transwell filters from Corning (Transwell permeable supports, Corning Inc., Miami Fla.). Cells are maintained on 10-cm tissue culture plates in medium containing 5% FBS. However, 10% serum is used when the cells are actually on the filters. To plate cells on filters, a Transwell filter is placed in a 12-well tissue culture tray. Sufficient medium (containing 10% serum) is added to both the inside and outside of the Transwell filter to wet the filter. Cells from a confluent 10-cm dish are trypsinized, gently pelleted by centrifugation, and resuspended in 10 ml of medium containing 10% serum. 0.4 ml of cells are pipeted into the Transwell. Transwells are then placed in the 37° C. incubator, and are generally used after 3 or 4 days. The medium is changed after 1 or 2 days.

E. Pulse-Chase Analysis of Cells on Filters.

Confluent MDCK cell monolayers on polycarbonate filters are washed twice with PBS and starved in MEM minus cysteine for 15 min at 37° C. Proteins are then pulse-labeled by placing the Transwell on a 25 µl drop of MEM minus cysteine containing 44 µCi of [$^{35}$S] cysteine (specific activity: 1000 Ci/mmole) for 10 min at 37° C. For the chase, cells are then rinsed with MEM and by adding 0.2 ml MEM to the apical surface and 1 ml to the basolateral surface. Cells are then chased for various times, generally 0.5 h, 1 h, 2 h, 3 h, and 4 h. During the chase period, the test ligand directed against the pIgR that may or may not inhibit cleavage of the pIgR is included in the apical medium. In different samples, the test ligand is included at different concentrations, such as 10 µg/ml, 100 µg/ml, 1 mg/ml, and 5 mg/ml. In a negative control experiment, the test ligand is omitted, or a control ligand that is known not to inhibit cleavage of the pIgR is included in the apical medium. In a positive control experiment, leupeptin is included in the medium at a concentration of 0.1 mg/ml during the chase period.

At the conclusion of each chase period (i.e. 0, 0.5, 1, 2, 3 or 4 h), the apical medium is collected. To harvest the cells on filters, the filter is cut out from the holder with a scalpel. The filter is placed in a 1.5-ml tube containing 0.5 ml of SDS lysis buffer and boiled for 5 minutes. The liquid is then transferred to a new tube and immunoprecipitated as described earlier. To immunoprecipitate the medium, SDS is added to the medium to a final concentration of 0.8%, and the medium is boiled for 2 minutes. An equal volume of 5% Triton dilution buffer (same as 2.5% Triton dilution buffer, except with 5% Triton X-100) is added and the sample processed for immunoprecipitation in the same manner as the cell extract described above. The immunoprecipitates are analyzed by SDS-PAGE and the radioactivity in the different species quantitated using the Molecular Dynamics Phosphorimager.

F. Interpreting the Results of Pulse-Chase Experiments.

Immediately after the pulse period, the pIgR immunoprecipitated from the cells will have a Mr of approximately 105,000. After a chase of 0.5 or 1 h, the pIgR immunoprecipitated from the cells will have a Mr of approximately 120,000 due to modification of its oligosaccharide side chains to the complex type. Beginning at about 1 h and continuing thereafter, the pIgR will be cleaved to SC with an Mr of approximately 80,000 and released into the apical medium, where it will be immunoprecipitated. The rate of disappearance of the intact 120,000 Mr pIgR from the cells and the appearance of the 80,000 Mr SC in the apical medium is indicative of the rate of cleavage of pIgR to SC. The presence of a ligand that inhibits cleavage of pIgR to SC in the apical medium during the chase period will inhibit this process and will be reflected in a lower rate of appearance of the 80,000 Mr SC.

Example 9

This Example sets forth an exemplary protocol for in vivo testing of ligand binding. As discussed in more detail below, rats are anesthetized, the contents of the colon flushed, and radiolabeled ligand perfused through the colon. Ligand binding, transcytosis, delivery into the circulation and delivery into the organs is then monitored by measuring radioactivity in blood samples and in organs.

A. Animals

The experiments are performed on male Sprague Dawley Rats(Sasco), weighing 250-380 g. The rats are fasted overnight before each experiment. Anesthesia is induced by an i.m. injection of ketamine (70 mg/kg) and acepromazine(30 mg/kg).

B. Animal Surgery

The perfused segment is colon. The surgical procedure is similar to that described in earlier publications (Hu, et al., J Theor. Biol., 131:107-114 (1988); Zheng et al., Pharm. Res., 11: 1771-1776 (1994)), with minor modifications. In this study, the cannulation to the colon is through an inter-cannulae, which is 1.5-2 cm long and can be easily disconnected or reconnected. The bile duct is also cannulated for collecting the bile (see, Borchardt, R. T., et al., eds. *Models for Assessing Drug Absorption and Metabolism* (Plenum Press, New York, N.Y. 1996)). Briefly, after the cannulation of the colon, the bile duct is located and cannulated using PE10 tubing. The cannulae is secured with surgical silk suture. The incision is then covered with a paper towel wetted with normal saline. A piece of plastic wrap is put on the towel to keep the segment moist. To keep the temperature of the perfusate constant, the inlet cannulate is insulated and kept warm by a 37° C. circulating bath.

C. Perfusion

The colon is perfused in situ with a washing buffer (a modified Hank's Balanced Salt Solution with leupeptin (0.1 mg/ml), aprotinin (50 U/ml), BSA(1 mg/ml), chymostatin (0.05 mg/ml)and NaI 0.1 mM, with/without NAC (20 mM)) to clean up the content. A washing buffer is then introduced into the colon under mild pressure to ensure distention for 2 min, and then removed. This washing is repeated 3 times. The perfusate solution (washing buffer without NAC but with the ligand and with PEG-4000 (100 µM)) is then introduced at a flow rate of 0.192 ml/min for the first 15 min, and at a flow rate of 0.077 ml/min for additional 15 min.

D. Sampling

Samples of the perfusate are collected for two hours at 30 min intervals at a flow rate of 0.077 ml/min. The perfusion is then stopped, and the colon is closed and kept closed for the remainder of the study. After 8 hr of perfusion, the perfusate is pushed out of colon using a syringe and collected. The perfused segment is then collected and its length measured by wetting it with normal saline and carefully laying it flat without stretching. The outlet concentration of the test compound is determined by a Gamma counter.

In addition to perfusate sampling, the blood samples(0.15-0.20 ml) are taken at 15, 30, 60, 90, 120 150, 240, 330, 420 and 480 min after the start of the perfusion. The bile is collected from the cannulae of the bile duct from time zero to the end of the studies. The weights of the blood and the bile are recorded by weighing the tubes with heparin (for the blood) or without (for the bile) before and after sample collection.

Rats are euthanized and organs harvested at the end the study. Weights of heart, lung, liver, spleen, kidney, intestine, colon and cecum are measured. The amount of the test compound in each organ is determined by using the gamma counter. The appearance of the radiolabel in the organs is a measure of the binding, internalization, transcytosis, and release, of the ligand.

The stability of the perfused $^{125}$I-labeled proteins is checked by precipitation of the collected blood, bile and perfusate samples. Briefly, 100 μL (2 M) trichloracetic acid ("TCA") is added to 200 μL each of the samples. The mixture is centrifuged at 16,000 G, for 5 min at room temperature. The pellet is collected by discarding the supernatant. The efficiency of the precipitation is calculated from the measured CPM values before and after the precipitation.

Example 10

This Example describes the creation of an antibody bearing a "FLAG"® (SEQ ID NO:22). FIG. 5 sets forth the sequence of an exemplary antibody, antibody 4AF, bearing a FLAG® (SEQ ID NO:22) tag. Antibodies for detecting the FLAG® (SEQ ID NO:22) tag are commercially available from Sigma (St. Louis, Mo.).

For convenience in secreting the antibody, scFv are typically engineered to have a so-called "pelB" leader sequence, which improves periplasmic secretion when the antibody is produced in *E. coli*. The leader sequence is cleaved upon secretion by the bacteria. The sequence further contains, immediately following the carboxy-terminus of the scFv, a Not I restriction site and a "myc" tag (an epitope from the myc oncogne) which can be specifically bound by commercially available antibodies. Finally, the sequence includes at the carboxy end six histidines. This "6HIS" tag permits ready purification of the secreted protein by running the protein over a column packed with nickel immobilized on a resin, as the histidines chelate to the metal. The preferred immobilized metal affinity chromatography, or "IMAC," process used to purify the scFv is nickel-NTA-superflow.

The "FLAG®" (SEQ ID NO:22) tagged version of the scFv is made by amplifying the scFv DNA in the plasmid pSyn (a pUC119 derivative which contains the pelb leader sequence which improves secretion in *E. coli*), using a primer which hybridizes in the vector sequence 3' to the ScFv coding region. A second primer is used which adds a FLAG® (SEQ ID NO:22) tag to the N-terminus of the ScFv. This primer is designed to contain a Nco I restriction site. The primer hybridizes to the 5' end of the ScFv coding region in the conserved framework region. The resulting PCR product is cloned back into pSyn using the restriction enzymes Nco I and Not I. Myc is a second tag, which is identified by a mouse monoclonal antibody, 9E10, available from the American Type Culture Collection (Manassas, Va.).

Example 11

This Example sets forth an exemplary protocol for in vitro testing of binding, transcytosis, and release of anti-pIgR-antibodies.

The scFv or other antibody to be tested is radio-iodinated by the method of Goldstein et al., (Meth Enzymol. 96:241-249, 1983), except that the iodine monochloride is diluted an additional 5-fold before addition to the reaction mixture. For each scFv to be tested, three 12 mm 0.4 um pore size Tranrswell filters (Costar) containing MDCK cells transfected with the appropriate species of pIgR (that is, human, rat, etc.) and three filters containing non transfected MDCK cells as a control, are cultured for 4 days, as described in Breitfeld et al., (1989), supra. The iodinated scFvs (10 cpm in 300 ul of minimum essential medium ("MEM")/bovine serum albumin ("BSA") are added to the apical chamber of each Transwell, and 800 μl of MEM/BSA is added to the basal medium. The filter units are transferred to new cluster dishes containing fresh basal medium at the desired time points (typically 1, 2, 4, 8, and 12 hours). At the end of the assay, apical medium is collected, and the filters are washed four times with cold MEM/BSA. If the scFv is engineered to contain a tail containing six or more histidines, the intact scFv cam can be precipitated from the apical and basal media using immobilized nickel resin (Qiagen). If the scFv are not engineered to contain a repetitive histidine sequence, the scFv can be precipitated with an antibody to another tag on the ScFv, or by TCA precipitation. After washing with PBS to remove non-specific radioactivity, the basal media, apical media, and filters can be quantitated in a gamma counter (Beckman Instruments, Palo Alto, Calif.). The percentage of the total ligand added that is transcytosed can be determined, and specific transcytosis can be assessed by comparing the pIgR expressing cells with the non-transfected MDCK cells.

Example 12

This Example describes the epitopes to which various human scFvs displayed in filamentous phage bound.

A series of 87 "staggered" peptides of 15 amino acid residues each were created from the pIgR sequences of the human, rat and mouse pIgR sequences, respectively. Each peptide within a series (that is, from the peptide sequence of a particular species) overlapped by 12 amino acids the next peptide in that series. Additionally, peptides created from the sequence of rabbit pIgR were created. Peptide binding was tested by ELISA, following a protocol developed by Chiron Technologies (since acquired by Mimitopes Pty. LTD., Melbourne, Australia), as set forth in the Example below.

The studies revealed that antibody 4A bound to the epitope defined by the sequence QDPRLF in human pIgR (residues 600 to 605 of the human sequence as set forth in SWISS-PROT) and to the epitope defined by the sequence LDPRLF (SEQ ID NO:11) in rat pIgR (residues 605-610 of the rat pIgR sequence), an epitope also bound by antibody 5D. Antibody 5D also bound to the epitope defined by the sequence KAIQDPRLF (SEQ ID NO:12) of human pIgR. ScFv 2E bound to the epitope defined by the sequence LDPRLFA-DERI (SEQ ID NO:13) of rat pIgR. ScFv 2H bound to the epitope defined by the sequence DENKANLDPRLF (SEQ ID NO:14). ScFv IF bound to the epitope defined by the sequence RLFADERI (SEQ ID NO:15). ScFvs 5F, 10H, 1C, 7H, and 6B all bound to the epitope defined by the sequence LDPRLFADE (SEQ ID NO:16).

Example 13

This Example describes determining assaying for binding of scFv or other antibodies to peptides derived from pIgR.

The binding of scFv antibodies from a human library was mapped by creating 94 peptides derived from pIgR of human, mouse, rat, and rabbit. The peptides were tested pursuant to the following protocol:

Introduction

The use of peptides in solid-phase immunoassays requires an efficient method for immobilization of the peptides on the solid phase, i.e. a method which does not depend on the amino acid sequence of the peptide being tested (Geerligs, H. J. et al., J. Immunol. Meth. 106:239-244 (1988)). For this purpose, multiple synthetic peptides are biotinylated and attached to a plastic surface coated with avidin or streptavidin (Weiner, A. J. et al., Proc. Natl. Acad. Sci. USA 3468-3472 (1992)).

Materials Required

Biotinylated synthetic peptides; microtiter plates e.g. Nunc Immuno-Plate MaxiSorb F96 (Cat. No. 4-42404); streptavidin (Sigma Cat. No. S-4762); bovine serum albumin (BSA); sodium azide PBS/Tween 20 (0.1% Tween 20 in PBS); PBS/BSA/azide (0.1% BSA and 0.1% sodium azide in PBS); 2% BSA/PBS (PBS containing 2% BSA) conjugate substrate; and an ELISA plate reader.

Method

1. Coat Nunc Immuno-Plate MaxiSorb F96 flat bottomed plates (Cat. No. 4-42404) with 5 microgram/mL streptavidin (Sigma Cat. No. S-4762) diluted in purified water. Add 100 microlitres of the streptavidin solution to each well and leave plates exposed to the air at 37 degrees C. overnight to allow the solution to evaporate to dryness.

2. Wash plates with Phosphate Buffered Saline ("PBS," 0.01M sodium phosphate in 0.15M sodium chloride, pH7.2) containing 0.1% (v/v) Tween 20 (PBS/Tween 20). The washing technique is as follows: flood the plate, filling all the wells with solution, then vigorously flick the solution from the wells. This washing step is repeated 4 times. After the washings, excess buffer is removed from the wells by vigorously "slapping" the plates, wells down, on a benchtop covered with an absorbent material (paper towels).

3. To block non-specific absorption, add to each well 200 uL of a solution consisting of PBS containing 2% (w/v) bovine serum albumin (2% BSA/PBS) and incubate the plate at 20 degrees C. for 1 hr.

4. Repeat washes as described in Step 2.

5. The biotinylated peptides are supplied as a dry powder in Bio-Rad polypropylene tubes (Cat. No. 223-9390). The identity of the peptide in each tube is given in the information supplied with the peptides. For use, we recommend that the peptides are reconstituted in 200 microlitre of either a pure solvent (e.g. dimethyl sulfoxide or dimethyl formamide) or solvent/water mixture. Each peptide should be diluted just before use to a working strength of $1/1000$ in PBS/BSA/azide, i.e. PBS containing 0.1% BSA and 0.1% sodium azide. The peptide stock solution may be diluted further (down to $1/5000$), however some loss in ELISA sensitivity may occur if used too dilute.

6. An initial $1/100$ dilution is conveniently made using 1 mL capacity polypropylene tubes, held in an 8×12 format rack (Bio-Rad Cat. No. 223-9390 as used for supply of the peptides is suitable). Using a multichannel pipette, transfer a 10 uL aliquot of peptide solution into each tube, then add 1 mL of the PBS/BSA/azide, cap the tubes and invert several times to ensure thorough mixing. The diluted peptide solutions may be stored for several days at 4 degrees C. For longer storage the diluted peptide solutions should be stored frozen. The tubes containing the supplied peptides should be resealed and stored frozen immediately after sampling, at −70 degrees C. To react the streptavidin coated, BSA blocked plates with the biotinylated peptides, transfer 100 microlitre of each of the diluted peptide solutions into the corresponding well positions of the plate, place the plate shaker and allow the reaction to proceed for 1 hr at 20 degrees C. For convenience, several sets of immobilised peptides may be prepared simultaneously.

7. Repeat washes as described in Step 2. The plates should be dried at 37 degrees C. before storage at 4 degrees C. in the dry state if they are not to be used immediately.

8. Dilute the serum to be tested, using as diluent 2% BSA/PBS containing 0.1% sodium azide. The dilution of the serum will depend to some extent on the source and the level of antibodies present in sample. The recommended dilutions are $1/1000$ for hyperimmune serum from experimental animals and ascites fluid from hybridoma-bearing mice, and $1/500$ for human serum. For scFvs, a concentration of between about 10 and 100 µg/mL is desirable. Conveniently, an scFv with an epitope tag to faciliater later detection. Add 100 microliters of the scFv or diluted serum to each of the wells of the plate containing captured peptides. Place the plate on a shaker and incubate for 1 hr at 20 degrees C. or overnight at 4 degrees C. Better sensitivity has been observed for some antibodies with overnight reaction.

9. Repeat washes as described in Step 2.

10. Bound antibody is detected after reaction for 1 hr at 20 degrees C. with 100 microlitre conjugate comprising a saturating level of horse radish peroxidase-labelled anti-species antibody (for the diluted serum samples; use $1/2000$ dilution of the 0.5 mg pack size conjugate from Kirkegaard and Perry Labs, Maryland, to be made up in 2% BSA/PBS. Note: do not use a diluent containing azide for HRP conjugates. For an epitope-tagged scFv, use an antibody appropriate for the epitope tag employed.)

11. Repeat washes as described in Step 2.

12. Wash the plate twice with PBS only (no Tween): to remove traces of Tween remaining from the washing buffer.

13. The presence of enzyme is detected by reaction for up to 45 min at 20 degrees C. with 100 microlitre/well freshly prepared enzyme substrate solution. The substrate solution consists of 50 mg of (2,2'-Azino-di-[3-ethylbenzothiazoline sulphonate]; Boehringer Mannheim Cat. No. 122661) and 30microlitre of 35% (w/w) hydrogen peroxide solution in 100 mL of 0.1 M phosphate/0.08M citrate buffer, pH4.0. Using substrate the absorbance of the converted substrate solutions (product) in each well is read using a plate reader. The Titertek Multiskan MC plate reader in the dual wavelength mode at 405 nm against a wavelength of 492 nm is suitable. The absorbance values are recorded and stored on a diskette for later analysis. The plate-reading software suppied with peptide synthesis kits is suitable for this purpose.

Notes

Other brands of streptavidin, or avidin, may be used to coat plates; however, to obtain optimum results, coating conditions may need to be varied. Avidin is cheaper than streptavidin but avidin-coated plates tend to result in higher background absorbance readings.

Other ELISA enzyme/substrate systems may be used, but the sensitivity of the test will vary accordingly. conditions for each ELISA system should be optimised (substrate concentration, pH, temperature, time etc.). A test should be done using preimmune, negative or normal serum to verify that any binding observed was to specific antibodies. Likewise, a negative control test can be performed with direct addition of conjugate toplates coated with (strept)avidin-peptide to ensure that the positives are not due to conjugate binding directly the peptide.

Example 14

This Examples sets forth an exemplary protocol for the production of fusion proteins comprising the pIgR B region and the stalk, and for producing polyclonal antibodies directed against the B-region and the stalk.

A. Production of Glutathione-S-Transferase Fused to Rat pIgR Residues 547-643 (GST-ratpIgR547-643).

cDNA encoding rat pIgR was amplified by PCR to incorporate BamI and EcoRI sites. The resulting PCR product was cleaved with BamHI and EcoRI, and cloned into BamHI/EcoRI cleaved pGEX2tk (Pharmacia). The pGEX2tk had been previously modified so that it encodes an in-frame 6HIS tag downstream of the cloning sites. The ligation mixture was used to transform *E. coli* DH5alpha. Positive clones were screened for expression of fusion protein after induction of cultures with IPTG. Clones that expressed well were used to make large scale (1 Liter) cultures expressing fusion protein. The bacteria were pelleted, resuspended in 1/100th the original culture volume (10 ml) PBS containing 0.2 mM PMSF. Tubes containing 5-10 ml of the cell suspension were sonicated using a Branson Model 250 sonifier (8 15 sec burst at setting 7). Trion X-100 was added to a final concentration of 1%, and the sample was rotated at 4 degrees for 10 minutes. Fusion protein was then purified using Glutathione Sepharose according to the Pharmacia protocol. Yields from DH5alpha were typically 2 mg fusion protein per liter of bacterial culture.

The pGEX2tk vector with the 6HIS tag was also transformed into *E. coli* strain DH5alpha, and protein was prepared as described above.

B. Antibody Production

Fusion proteins were sent to to HTI Bioproducts (now called Strategic Biosolutions, Ramona, Calif.) for antibody production in goats, rabbits and chickens. For goats, 200 ug of fusion protein was used for the initial injection (Day 1) with Complete Freund's Adjuvant. Booster injections of 200 ug fusion protein with Incomplete Freund's Adjuvant were given on days 14, 28, and 42. All injections were subcutaneous. A test bleed was done on day 49, and the blood was screened by ELISA for reactivity with the fusion protein. Positive bleeds were tested by western blot to confirm reactivity with pIgR. Animals with high titers were subjected to plasmaphoresis. Goat IgG was purified from plasma ion-exchange chromatography. IgG was further purified by affinity purification on GST-ratpIgR547-643 coupled to Affi-Gel (Bio-Rad) according to the protocol supplied with Affi-Gel. Antibodies reactive with the GST portion of the molecule were removed by incubating the antibody preparation with GST protein coupled to Affi-Gel.

Epitope mapping of the antibodies was performed as described above with respect to testing of scFvs, using non-affinity purified IgG.

It is understood that the examples and embodiments described herein are for illustrative purposes only and that various modifications or changes in light thereof will be suggested to persons skilled in the art and are to be included within the spirit and purview of this application and scope of the appended claims. All publications and patents mentioned in this specification are herein incorporated by reference into the specification to the same extent as if each individual publication or patent was specifically and individually indicated to be incorporated herein by reference.

What is claimed is:

1. A method of targeting an effector moiety to an epithelial cell of an organ of interest in an animal, which cell has an apical surface and expresses a polymeric immunoglobulin receptor (pIgR), which pIgR when cleaved has a stalk region which remains attached to the cell and a secretory component which exists in the organ of interest in several forms, by contacting pIgR attached to said apical surface with an immunoconjugate comprising an effector moiety and an antibody, which antibody binds pIgR, with the provisos that
   (a) the antibody binds to a region of pIgR that is absent from the majority of free (cleaved) secretory component in the organ of interest, and
   (b) the antibody does not bind to the stalk region remaining attached to the cell after pIgR cleavage, under physiological conditions, thereby targeting said effector moiety to said cell.

2. A method of claim 1, wherein the antibody is a humanized antibody.

3. A method of claim 1, wherein the antibody is selected from the group consisting of a recombinant single chain variable region fragment of an antibody and a disulfide stabilized variable region fragment.

4. A method of claim 1, wherein the effector moiety is a nucleic acid which encodes the wildtype cystic fibrosis transmembrane conductance regulator.

5. A method of claim 1, wherein the effector moiety is a therapeutic agent.

6. A method of claim 1, wherein the cell is a mammalian cell.

7. A method of claim 1, wherein the organ of interest is selected from the group consisting of a small intestine, a large intestine, a liver-biliary tree, a stomach, a salivary gland, a lung, a vagina, a uterus, a lacrimal gland, a mammary gland, a nasal passage, and a sinus.

* * * * *

SEQUENCE LISTING

```
<160> NUMBER OF SEQ ID NOS: 26

<210> SEQ ID NO 1
<211> LENGTH: 764
<212> TYPE: PRT
<213> ORGANISM: Homo sapiens
<220> FEATURE:
<223> OTHER INFORMATION: human polymeric Immunoglobulin receptor (pIgR)

<400> SEQUENCE: 1

Met Leu Leu Phe Val Leu Thr Cys Leu Leu Ala Val Phe Pro Ala Ile
 1               5                  10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
 65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175
```

-continued

```
Ile Asp Ser Ser Gly Tyr Val Asn Pro Asn Tyr Thr Gly Arg Ile Arg
        180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
        210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
            245                 250                 255

Cys Ala Leu Gly Pro Glu Val Ala Asn Val Ala Lys Phe Leu Cys Arg
        260                 265                 270

Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
        290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
        340                 345                 350

Pro Arg Ser Pro Thr Val Val Lys Gly Val Ala Gly Ser Ser Val Ala
        355                 360                 365

Val Leu Cys Pro Tyr Asn Arg Lys Glu Ser Lys Ser Ile Lys Tyr Trp
        370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
            405                 410                 415

Glu Glu Pro Gly Asn Gly Thr Phe Thr Val Ile Leu Asn Gln Leu Thr
        420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
        450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
            485                 490                 495

Lys Trp Asn Asn Thr Gly Cys Gln Ala Leu Pro Ser Gln Asp Glu Gly
        500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
        530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
        580                 585                 590

Glu Ile Glu Asn Lys Ala Ile Gln Asp Pro Arg Leu Phe Ala Glu Glu
```

-continued

```
                595                 600                 605
Lys Ala Val Ala Asp Thr Arg Asp Gln Ala Asp Gly Ser Arg Ala Ser
            610                 615                 620
Val Asp Ser Gly Ser Ser Glu Glu Gln Gly Gly Ser Ser Arg Ala Leu
625                 630                 635                 640
Val Ser Thr Leu Val Pro Leu Gly Leu Val Leu Ala Val Gly Ala Val
                645                 650                 655
Ala Val Gly Val Ala Arg Ala Arg His Arg Lys Asn Val Asp Arg Val
            660                 665                 670
Ser Ile Arg Ser Tyr Arg Thr Asp Ile Ser Met Ser Asp Phe Glu Asn
            675                 680                 685
Ser Arg Glu Phe Gly Ala Asn Asp Asn Met Gly Ala Ser Ser Ile Thr
            690                 695                 700
Gln Glu Thr Ser Leu Gly Gly Lys Glu Glu Phe Val Ala Thr Thr Glu
705                 710                 715                 720
Ser Thr Thr Glu Thr Lys Glu Pro Lys Lys Ala Lys Arg Ser Ser Lys
                725                 730                 735
Glu Glu Ala Glu Met Ala Tyr Lys Asp Phe Leu Leu Gln Ser Ser Thr
            740                 745                 750
Val Ala Ala Glu Ala Gln Asp Gly Pro Gln Glu Ala
            755                 760

<210> SEQ ID NO 2
<211> LENGTH: 757
<212> TYPE: PRT
<213> ORGANISM: Bos taurus
<220> FEATURE:
<223> OTHER INFORMATION: bovine polymeric immunoglobulin receptor (pIgR)

<400> SEQUENCE: 2

Met Ser Arg Leu Phe Leu Ala Cys Leu Leu Ala Ile Phe Pro Val Val
1               5                   10                  15
Ser Met Lys Ser Pro Ile Phe Gly Pro Glu Glu Val Thr Ser Val Glu
                20                  25                  30
Gly Arg Ser Val Ser Ile Lys Cys Tyr Tyr Pro Pro Thr Ser Val Asn
            35                  40                  45
Arg His Thr Arg Lys Tyr Trp Cys Arg Gln Gly Ala Gln Gly Arg Cys
        50                  55                  60
Thr Thr Leu Ile Ser Ser Glu Gly Tyr Val Ser Asp Tyr Val Gly
65              70                  75                  80
Arg Ala Asn Leu Thr Asn Phe Pro Glu Ser Gly Thr Phe Val Val Asp
                85                  90                  95
Ile Ser His Leu Thr His Lys Asp Ser Gly Arg Tyr Lys Cys Gly Leu
            100                 105                 110
Gly Ile Ser Ser Arg Gly Leu Asn Phe Asp Val Ser Leu Glu Val Ser
        115                 120                 125
Gln Asp Pro Ala Gln Ala Ser His Ala His Val Tyr Thr Val Asp Leu
    130                 135                 140
Gly Arg Thr Val Thr Ile Asn Cys Pro Phe Thr Arg Ala Asn Ser Glu
145                 150                 155                 160
Lys Arg Lys Ser Leu Cys Lys Lys Thr Ile Gln Asp Cys Phe Gln Val
                165                 170                 175
Val Asp Ser Thr Gly Tyr Val Ser Asn Ser Tyr Lys Asp Arg Ala His
            180                 185                 190
Ile Ser Ile Leu Gly Thr Asn Thr Leu Val Phe Ser Val Val Ile Asn
```

-continued

```
              195                 200                 205
Arg Val Lys Leu Ser Asp Ala Gly Met Tyr Val Cys Gln Ala Gly Asp
    210                 215                 220

Asp Ala Lys Ala Asp Lys Ile Asn Ile Asp Leu Gln Val Leu Glu Pro
225                 230                 235                 240

Glu Pro Glu Leu Val Tyr Gly Asp Leu Arg Ser Ser Val Thr Phe Asp
                245                 250                 255

Cys Ser Leu Gly Pro Glu Val Ala Asn Val Pro Lys Phe Leu Cys Gln
                260                 265                 270

Lys Lys Asn Gly Gly Ala Cys Asn Val Val Ile Asn Thr Leu Gly Lys
            275                 280                 285

Lys Ala Gln Asp Phe Gln Gly Arg Ile Val Ser Val Pro Lys Asp Asn
        290                 295                 300

Gly Val Phe Ser Val His Ile Thr Ser Leu Arg Lys Glu Asp Ala Gly
305                 310                 315                 320

Arg Tyr Val Cys Gly Ala Gln Pro Glu Gly Glu Pro Gln Asp Gly Trp
                325                 330                 335

Pro Val Gln Ala Trp Gln Leu Phe Val Asn Glu Glu Thr Ala Ile Pro
                340                 345                 350

Ala Ser Pro Ser Val Val Lys Gly Val Arg Gly Gly Ser Val Thr Val
            355                 360                 365

Ser Cys Pro Tyr Asn Pro Lys Asp Ala Asn Ser Ala Lys Tyr Trp Cys
        370                 375                 380

His Trp Glu Glu Ala Gln Asn Gly Arg Cys Pro Arg Leu Val Glu Ser
385                 390                 395                 400

Arg Gly Leu Ile Lys Glu Gln Tyr Glu Gly Arg Leu Ala Leu Leu Thr
                405                 410                 415

Glu Pro Gly Asn Gly Thr Tyr Thr Val Ile Leu Asn Gln Leu Thr Asp
                420                 425                 430

Gln Asp Thr Gly Phe Tyr Trp Cys Val Thr Asp Gly Asp Thr Arg Trp
            435                 440                 445

Ile Ser Thr Val Glu Leu Lys Val Val Gln Gly Glu Pro Ser Leu Lys
        450                 455                 460

Val Pro Lys Asn Val Thr Ala Trp Leu Gly Glu Pro Leu Lys Leu Ser
465                 470                 475                 480

Cys His Phe Pro Cys Lys Phe Tyr Ser Phe Glu Lys Tyr Trp Cys Lys
                485                 490                 495

Trp Ser Asn Arg Gly Cys Ser Ala Leu Pro Thr Gln Asn Asp Gly Pro
                500                 505                 510

Ser Gln Ala Phe Val Ser Cys Asp Gln Asn Ser Gln Val Val Ser Leu
            515                 520                 525

Asn Leu Asp Thr Val Thr Lys Glu Asp Glu Gly Trp Tyr Trp Cys Gly
        530                 535                 540

Val Lys Glu Gly Pro Arg Tyr Gly Glu Thr Ala Ala Val Tyr Val Ala
545                 550                 555                 560

Val Glu Ser Arg Val Lys Gly Ser Gln Gly Ala Lys Gln Val Lys Ala
                565                 570                 575

Ala Pro Ala Gly Ala Ala Ile Gln Ser Arg Ala Gly Glu Ile Gln Asn
                580                 585                 590

Lys Ala Leu Leu Asp Pro Ser Phe Phe Ala Lys Glu Ser Val Lys Asp
            595                 600                 605

Ala Ala Gly Gly Pro Gly Ala Pro Ala Asp Pro Gly Arg Pro Thr Gly
        610                 615                 620
```

```
Tyr Ser Gly Ser Ser Lys Ala Leu Val Ser Thr Leu Val Pro Leu Ala
625                 630                 635                 640

Leu Val Leu Val Ala Gly Val Ala Ile Gly Val Val Arg Ala Arg
            645                 650                 655

His Arg Lys Asn Val Asp Arg Ile Ser Ile Arg Ser Tyr Arg Thr Asp
                660                 665                 670

Ile Ser Met Ser Asp Phe Glu Asn Ser Arg Asp Phe Glu Gly Arg Asp
            675                 680                 685

Asn Met Gly Ala Ser Pro Glu Ala Gln Glu Thr Ser Leu Gly Gly Lys
        690                 695                 700

Asp Glu Phe Ala Thr Thr Thr Glu Asp Thr Val Glu Ser Lys Glu Pro
705                 710                 715                 720

Lys Lys Ala Lys Arg Ser Ser Lys Glu Glu Ala Asp Glu Ala Phe Thr
                725                 730                 735

Thr Phe Leu Leu Gln Ala Lys Asn Leu Ala Ser Ala Thr Gln Asn
            740                 745                 750

Gly Pro Thr Glu Ala
        755

<210> SEQ ID NO 3
<211> LENGTH: 769
<212> TYPE: PRT
<213> ORGANISM: Rattus sp.
<220> FEATURE:
<223> OTHER INFORMATION: rat polymeric immunoglobulin receptor (pIgR)

<400> SEQUENCE: 3

Met Arg Leu Ser Leu Phe Ala Leu Leu Val Thr Val Phe Ser Gly Val
1               5                   10                  15

Ser Thr Gln Ser Pro Ile Phe Gly Pro Gln Asp Val Ser Ser Ile Glu
            20                  25                  30

Gly Asn Ser Val Ser Ile Thr Cys Tyr Tyr Pro Asp Thr Ser Val Asn
        35                  40                  45

Arg His Thr Arg Lys Tyr Trp Cys Arg Gln Gly Ala Asn Gly Tyr Cys
    50                  55                  60

Ala Thr Leu Ile Ser Ser Asn Gly Tyr Leu Ser Lys Glu Tyr Ser Gly
65                  70                  75                  80

Arg Ala Ser Leu Ile Asn Phe Pro Glu Asn Ser Thr Phe Val Ile Asn
                85                  90                  95

Ile Ala His Leu Thr Gln Glu Asp Thr Gly Ser Tyr Lys Cys Gly Leu
            100                 105                 110

Gly Thr Thr Asn Arg Gly Leu Phe Phe Asp Val Ser Leu Glu Val Ser
        115                 120                 125

Gln Val Pro Glu Phe Pro Asn Asp Thr His Val Tyr Thr Lys Asp Ile
    130                 135                 140

Gly Arg Thr Val Thr Ile Glu Cys Arg Phe Lys Glu Gly Asn Ala His
145                 150                 155                 160

Ser Lys Lys Ser Leu Cys Lys Lys Arg Gly Glu Ala Cys Glu Val Val
                165                 170                 175

Ile Asp Ser Thr Glu Tyr Val Asp Pro Ser Tyr Lys Asp Arg Ala Ile
            180                 185                 190

Leu Phe Met Lys Gly Thr Ser Arg Asp Ile Phe Tyr Val Asn Ile Ser
        195                 200                 205

His Leu Ile Pro Ser Asp Ala Gly Leu Tyr Val Cys Gln Ala Gly Glu
    210                 215                 220
```

```
Gly Pro Ser Ala Asp Lys Asn Asn Ala Asp Leu Gln Val Leu Glu Pro
225                 230                 235                 240

Glu Pro Glu Leu Leu Tyr Lys Asp Leu Arg Ser Ser Val Thr Phe Glu
            245                 250                 255

Cys Asp Leu Gly Arg Glu Val Ala Asn Asp Ala Lys Tyr Leu Cys Arg
            260                 265                 270

Lys Asn Lys Glu Thr Cys Asp Val Ile Ile Asn Thr Leu Gly Lys Arg
            275                 280                 285

Asp Pro Ala Phe Glu Gly Arg Ile Leu Leu Thr Pro Arg Asp Asp Asn
290                 295                 300

Gly Arg Phe Ser Val Leu Ile Thr Gly Leu Arg Lys Glu Asp Ala Gly
305                 310                 315                 320

His Tyr Gln Cys Gly Ala His Ser Ser Gly Leu Pro Gln Glu Gly Trp
                325                 330                 335

Pro Val Gln Ala Trp Gln Leu Phe Val Asn Glu Glu Ser Thr Ile Pro
            340                 345                 350

Asn Ser Arg Ser Val Val Lys Gly Val Thr Gly Gly Ser Val Ala Ile
            355                 360                 365

Val Cys Pro Tyr Asn Pro Lys Glu Ser Ser Leu Lys Tyr Trp Cys
370                 375                 380

His Trp Glu Ala Asp Glu Asn Gly Arg Cys Pro Val Leu Val Gly Thr
385                 390                 395                 400

Gln Ala Leu Val Gln Glu Gly Tyr Glu Gly Arg Leu Ala Leu Phe Asp
                405                 410                 415

Gln Pro Gly Ser Gly Ala Tyr Thr Val Ile Leu Asn Gln Leu Thr Thr
            420                 425                 430

Gln Asp Ser Gly Phe Tyr Trp Cys Leu Thr Asp Gly Asp Ser Arg Trp
            435                 440                 445

Arg Thr Thr Ile Glu Leu Gln Val Ala Glu Ala Thr Lys Lys Pro Asp
450                 455                 460

Leu Glu Val Thr Pro Gln Asn Ala Thr Ala Val Ile Gly Glu Thr Phe
465                 470                 475                 480

Thr Ile Ser Cys His Tyr Pro Cys Lys Phe Tyr Ser Gln Glu Lys Tyr
                485                 490                 495

Trp Cys Lys Trp Ser Asn Asp Gly Cys His Ile Leu Pro Ser His Asp
            500                 505                 510

Glu Gly Ala Arg Gln Ser Ser Val Ser Cys Asp Gln Ser Ser Gln Ile
            515                 520                 525

Val Ser Met Thr Leu Asn Pro Val Lys Lys Glu Asp Glu Gly Trp Tyr
530                 535                 540

Trp Cys Gly Val Lys Glu Gly Gln Val Tyr Gly Glu Thr Thr Ala Ile
545                 550                 555                 560

Tyr Val Ala Val Glu Glu Arg Thr Arg Gly Ser Pro His Ile Asn Pro
                565                 570                 575

Thr Asp Ala Asn Ala Arg Ala Lys Asp Ala Pro Glu Glu Glu Ala Met
            580                 585                 590

Glu Ser Ser Val Arg Glu Asp Glu Asn Lys Ala Asn Leu Asp Pro Arg
            595                 600                 605

Leu Phe Ala Asp Glu Arg Glu Ile Gln Asn Ala Gly Asp Gln Ala Gln
            610                 615                 620

Glu Asn Arg Ala Ser Gly Asn Ala Gly Ser Ala Gly Gly Gln Ser Gly
625                 630                 635                 640
```

-continued

```
Ser Ser Lys Val Leu Phe Ser Thr Leu Val Pro Leu Gly Leu Val Leu
            645                 650                 655

Ala Val Gly Ala Val Ala Val Trp Val Ala Arg Val Arg His Arg Lys
        660                 665                 670

Asn Val Asp Arg Met Ser Ile Ser Ser Tyr Arg Thr Asp Ile Ser Met
    675                 680                 685

Gly Asp Phe Arg Asn Ser Arg Asp Leu Gly Gly Asn Asp Asn Met Gly
690                 695                 700

Ala Thr Pro Asp Thr Gln Glu Thr Val Leu Glu Gly Lys Asp Glu Ile
705                 710                 715                 720

Glu Thr Thr Thr Glu Cys Thr Thr Glu Pro Glu Ser Lys Lys Ala
            725                 730                 735

Lys Arg Ser Ser Lys Glu Glu Ala Asp Met Ala Tyr Ser Ala Phe Leu
        740                 745                 750

Phe Gln Ser Ser Thr Ile Ala Ala Gln Val His Asp Gly Pro Gln Glu
            755                 760                 765

Ala
```

```
<210> SEQ ID NO 4
<211> LENGTH: 771
<212> TYPE: PRT
<213> ORGANISM: Mus sp.
<220> FEATURE:
<223> OTHER INFORMATION: mouse polymeric immunoglobulin receptor (pIgR)

<400> SEQUENCE: 4
```

```
Met Arg Leu Tyr Leu Phe Thr Leu Leu Val Thr Val Phe Ser Gly Val
  1               5                  10                  15

Ser Thr Lys Ser Pro Ile Phe Gly Pro Gln Glu Val Ser Ser Ile Glu
             20                  25                  30

Gly Asp Ser Val Ser Ile Thr Cys Tyr Tyr Pro Asp Thr Ser Val Asn
         35                  40                  45

Arg His Thr Arg Lys Tyr Trp Cys Arg Gln Gly Ala Ser Gly Met Cys
     50                  55                  60

Thr Thr Leu Ile Ser Ser Asn Gly Tyr Leu Ser Lys Glu Tyr Ser Gly
 65                  70                  75                  80

Arg Ala Asn Leu Ile Asn Phe Pro Glu Asn Asn Thr Phe Val Ile Asn
                 85                  90                  95

Ile Glu Gln Leu Thr Gln Asp Asp Thr Gly Ser Tyr Lys Cys Gly Leu
            100                 105                 110

Gly Thr Ser Asn Arg Gly Leu Ser Phe Asp Val Ser Leu Glu Val Ser
        115                 120                 125

Gln Val Pro Glu Leu Pro Ser Asp Thr His Val Tyr Thr Lys Asp Ile
    130                 135                 140

Gly Arg Asn Val Thr Ile Glu Cys Pro Phe Lys Arg Glu Asn Ala Pro
145                 150                 155                 160

Ser Lys Lys Ser Leu Cys Lys Lys Thr Asn Gln Ser Cys Glu Leu Val
                165                 170                 175

Ile Asp Ser Thr Glu Lys Val Asn Pro Ser Tyr Ile Gly Arg Ala Lys
            180                 185                 190

Leu Phe Met Lys Gly Thr Asp Leu Thr Val Phe Tyr Val Asn Ile Ser
        195                 200                 205

His Leu Thr His Asn Asp Ala Gly Leu Tyr Ile Cys Gln Ala Gly Glu
    210                 215                 220

Gly Pro Ser Ala Asp Lys Lys Asn Val Asp Leu Gln Val Leu Ala Pro
```

-continued

```
              225                 230                 235                 240

Glu Pro Glu Leu Leu Tyr Lys Asp Leu Arg Ser Ser Val Thr Phe Glu
                        245                 250                 255

Cys Asp Leu Gly Arg Glu Val Ala Asn Glu Ala Lys Tyr Leu Cys Arg
                    260                 265                 270

Met Asn Lys Glu Thr Cys Asp Val Ile Ile Asn Thr Leu Gly Lys Arg
                275                 280                 285

Asp Pro Asp Phe Glu Gly Arg Ile Leu Ile Thr Pro Lys Asp Asp Asn
            290                 295                 300

Gly Arg Phe Ser Val Leu Ile Thr Gly Leu Arg Lys Glu Asp Ala Gly
        305                 310                 315                 320

His Tyr Gln Cys Gly Ala His Ser Ser Gly Leu Pro Gln Glu Gly Trp
                        325                 330                 335

Pro Ile Gln Thr Trp Gln Leu Phe Val Asn Glu Glu Ser Thr Ile Pro
                    340                 345                 350

Asn Arg Arg Ser Val Val Lys Gly Val Thr Gly Gly Ser Val Ala Ile
                355                 360                 365

Ala Cys Pro Tyr Asn Pro Lys Glu Ser Ser Leu Lys Tyr Trp Cys
            370                 375                 380

Arg Trp Glu Gly Asp Gly Asn Gly His Cys Pro Val Leu Val Gly Thr
        385                 390                 395                 400

Gln Ala Gln Val Gln Glu Tyr Glu Gly Arg Leu Ala Leu Phe Asp
                        405                 410                 415

Gln Pro Gly Asn Gly Thr Tyr Thr Val Ile Leu Asn Gln Leu Thr Thr
                    420                 425                 430

Glu Asp Ala Gly Phe Tyr Trp Cys Leu Thr Asn Gly Asp Ser Arg Trp
                435                 440                 445

Arg Thr Thr Ile Glu Leu Gln Val Ala Glu Ala Thr Arg Glu Pro Asn
        450                 455                 460

Leu Glu Val Thr Pro Gln Asn Ala Thr Ala Val Leu Gly Glu Thr Phe
        465                 470                 475                 480

Thr Val Ser Cys His Tyr Pro Cys Lys Phe Tyr Ser Gln Glu Lys Tyr
                        485                 490                 495

Trp Cys Lys Trp Ser Asn Lys Gly Cys His Ile Leu Pro Ser His Asp
                    500                 505                 510

Glu Gly Ala Arg Gln Ser Ser Val Ser Cys Asp Gln Ser Ser Gln Leu
                515                 520                 525

Val Ser Met Thr Leu Asn Pro Val Ser Lys Glu Asp Glu Gly Trp Tyr
            530                 535                 540

Trp Cys Gly Val Lys Gln Gly Gln Thr Tyr Gly Glu Thr Thr Ala Ile
        545                 550                 555                 560

Tyr Ile Ala Val Glu Glu Arg Thr Arg Gly Ser Ser His Val Asn Pro
                        565                 570                 575

Thr Asp Ala Asn Ala Arg Ala Lys Val Ala Leu Glu Glu Val Val
                    580                 585                 590

Asp Ser Ser Ile Ser Glu Lys Glu Asn Lys Ala Ile Pro Asn Pro Gly
                595                 600                 605

Pro Phe Ala Asn Glu Arg Glu Ile Gln Asn Val Gly Asp Gln Ala Gln
            610                 615                 620

Glu Asn Arg Ala Ser Gly Asp Ala Gly Ser Ala Asp Gly Gln Ser Arg
        625                 630                 635                 640

Ser Ser Ser Ser Lys Val Leu Phe Ser Thr Leu Val Pro Leu Gly Leu
                        645                 650                 655
```

```
Val Leu Ala Val Gly Ala Ile Ala Val Trp Val Ala Arg Val Arg His
            660                 665                 670

Arg Lys Asn Val Asp Arg Met Ser Ile Ser Ser Tyr Arg Thr Asp Ile
            675                 680                 685

Ser Met Ala Asp Phe Lys Asn Ser Arg Asp Leu Gly Gly Asn Asp Asn
            690                 695                 700

Met Gly Ala Ser Pro Asp Thr Gln Gln Thr Val Ile Glu Gly Lys Asp
705                 710                 715                 720

Glu Ile Val Thr Thr Thr Glu Cys Thr Ala Glu Pro Glu Ser Lys
                725                 730                 735

Lys Ala Lys Arg Ser Ser Lys Glu Glu Ala Asp Met Ala Tyr Ser Ala
            740                 745                 750

Phe Leu Leu Gln Ser Ser Thr Ile Ala Ala Gln Val His Asp Gly Pro
            755                 760                 765

Gln Glu Ala
    770

<210> SEQ ID NO 5
<211> LENGTH: 732
<212> TYPE: PRT
<213> ORGANISM: Didelphis sp.
<220> FEATURE:
<223> OTHER INFORMATION: possum polymeric immunoglobulin receptor (pIgR)

<400> SEQUENCE: 5

Met Ala Phe Phe Leu Ala Cys Leu Leu Ala Leu Leu Pro Val Val Ser
1               5                   10                  15

Met Lys Ser Pro Ile Phe Gly Pro Lys Gln Val Thr Gly Val Glu Gly
            20                  25                  30

Gly Ser Val Ser Ile Gln Cys Phe Tyr Pro Ser Ser Ser Val Asn Arg
        35                  40                  45

His Gly Arg Lys Tyr Phe Cys Leu Gln Asn Leu Arg Gln Ser Cys Glu
    50                  55                  60

Thr Ile Val Ser Ser Asn Gly Phe Val Ser Glu Arg Phe Ser Gly Arg
65                  70                  75                  80

Ala Lys Leu Thr Asn Phe Pro Gly Asn Asn Ser Phe Leu Ile Gln Ile
            85                  90                  95

Ser Gln Leu Glu Lys Glu Asp Ile Gly Leu Tyr Lys Cys Gly Leu Gly
            100                 105                 110

Thr Ser Asn Arg Gly Leu Ser Phe Asp Ile Thr Leu Glu Val Gly Glu
            115                 120                 125

Gly Pro Asn Leu Pro Asn Asn Thr Glu Val Ile Val Thr Glu Val Gly
        130                 135                 140

Lys Thr Val Ser Ile Asn Cys Pro Phe Gln Glu Gln Asn Thr Gln Asp
145                 150                 155                 160

Arg Lys Phe Leu Cys Lys Lys Asp Gly Glu Ser Cys Ala Leu Val Ile
            165                 170                 175

Asp Ser Gln Glu Gln Val Gly Pro Asp Tyr Thr Gly Arg Ala Arg Leu
            180                 185                 190

Ser Ile Ser Gly Thr Ser Ser Arg Val Phe Val Val Thr Ile Ser Gln
        195                 200                 205

Ile Lys Arg Gln Asp Val Gly Met Tyr Val Cys Gly Val Gly Glu Asp
    210                 215                 220

Ser Asp Thr Gly Ile Gln Lys Asn Val Asp Leu Lys Leu Leu Glu Pro
225                 230                 235                 240
```

```
Glu Pro Glu Leu Leu Tyr Ala Glu Leu Gly Gly Ser Val Thr Leu Asn
                245                 250                 255

Cys Ala Leu Gly Ser Thr Val Ala Ser Val Pro Lys Phe Leu Cys Gln
            260                 265                 270

Met Arg Ala Lys Glu Thr Cys Asp Leu Val Ile Asn Ser Lys Gly Phe
        275                 280                 285

Thr Asn Asn Ala Thr His Gly Arg Ile Leu Phe Ser His Thr Thr Glu
    290                 295                 300

Thr Gly Ser Phe Ser Ile Met Ile Thr Gln Val Arg Lys Glu Asp Glu
305                 310                 315                 320

Gly Val Tyr His Cys Gly Ala Gln Glu Asp Gly Gln Pro Ser Glu Glu
                325                 330                 335

Gly Pro Ile Arg Ala Leu Gln Leu Phe Val Ser Glu Glu Thr Thr Val
            340                 345                 350

Pro Lys Ser Pro Leu Val Val Lys Gly Pro Ser Gly Gly Ser Val Thr
        355                 360                 365

Ile Thr Cys His Tyr Asp Pro Lys Lys Asn Asn Thr Leu Lys Tyr Trp
    370                 375                 380

Cys Lys Trp Glu Gly Ser Ser His Cys Thr Lys Leu Val Asp Ser Leu
385                 390                 395                 400

Gly Met Val Asp Glu Ser Tyr Glu Gly Arg Val Ala Leu Trp Asp Glu
                405                 410                 415

Pro Glu Asn Gly Ile Phe Thr Val Ile Leu Asn Gln Leu Thr Pro Gln
            420                 425                 430

Asp Ala Gly Tyr Tyr Trp Cys Leu Ser Asn Gly Glu His Asn Arg Lys
        435                 440                 445

Ser Ser Val Lys Ile Glu Ile Asn Asp Gly Gln Pro Leu Leu Ile Ala
    450                 455                 460

Pro Lys Thr Val Thr Ala Gln Leu Gly Gln Ser Leu Thr Ile Ser Cys
465                 470                 475                 480

His Tyr Pro Cys Lys Phe Tyr Ser Tyr Glu Lys Tyr Trp Cys Lys Trp
                485                 490                 495

Ser Asn Gln Gly Cys Glu Thr Leu Pro Thr Gln Glu Glu Gly Ser Ser
            500                 505                 510

Gln Ala Phe Val Asp Cys Asn Gln Asn Ser Arg Asn Val Ser Leu Thr
        515                 520                 525

Leu Asn Ser Val Thr Arg Asp His Glu Gly Trp Tyr Trp Cys Gly Val
    530                 535                 540

Lys Asn Gly Gln Asn Tyr Gly Glu Thr Ile Ala Val Ser Val Ala Ser
545                 550                 555                 560

Glu Glu Glu Val Ser Gly Asn Ala Ile Gln Pro Thr Asn Ala Val Leu
                565                 570                 575

Asn Glu Asp Ala Val Glu Pro Lys Val Arg Gly Lys Glu Ile Glu Val
            580                 585                 590

Pro Thr Asp Leu Gly Ser Thr Glu Glu His Ser Gly Ser Ser Val
        595                 600                 605

Leu Val Ser Thr Leu Val Pro Leu Ala Leu Val Leu Thr Val Gly Ala
    610                 615                 620

Val Ala Leu Gly Ile Ile Lys Ala Arg Arg Trp Arg Phe Ser Asp Arg
625                 630                 635                 640

Val Ser Val Gly Ser Tyr Arg Thr Asp Leu Ser Met Ser Glu Leu Glu
                645                 650                 655
```

-continued

```
Asn Asn Pro Arg Gln Phe Gly Ala Asn Glu Asn Met Asp Ala Ser Val
            660                 665                 670

Gln Glu Thr Thr Leu Gly Gly Glu Asp Glu Leu Ala Thr Ala Thr Glu
            675                 680                 685

Ser Thr Val Glu Ile Glu Pro Lys Lys Ala Lys Arg Ser Ser Lys
            690                 695                 700

Glu Glu Ala Asp Leu Ala Tyr Ser Ala Phe Leu Leu Gln Ser Asn Thr
705                 710                 715                 720

Ile Ala Ala Glu His Gln Asp Gly Pro Lys Glu Ala
                725                 730

<210> SEQ ID NO 6
<211> LENGTH: 773
<212> TYPE: PRT
<213> ORGANISM: Oryctolagus cuniculus
<220> FEATURE:
<223> OTHER INFORMATION: rabbit polymeric immunoglobulin receptor (pIgR)

<400> SEQUENCE: 6

Met Ala Leu Phe Leu Leu Thr Cys Leu Leu Ala Val Phe Ser Ala Ala
  1               5                  10                  15

Thr Ala Gln Ser Ser Leu Leu Gly Pro Ser Ser Ile Phe Gly Pro Gly
             20                  25                  30

Glu Val Asn Val Leu Glu Gly Asp Ser Val Ser Ile Thr Cys Tyr Tyr
         35                  40                  45

Pro Thr Thr Ser Val Thr Arg His Ser Arg Lys Phe Trp Cys Arg Glu
     50                  55                  60

Glu Ser Gly Arg Cys Val Thr Leu Ala Ser Thr Gly Tyr Thr Ser
 65                  70                  75                  80

Gln Glu Tyr Ser Gly Arg Gly Lys Leu Thr Asp Phe Pro Asp Lys Gly
                 85                  90                  95

Glu Phe Val Val Thr Val Asp Gln Leu Thr Gln Asn Asp Ser Gly Ser
            100                 105                 110

Tyr Lys Cys Gly Val Gly Val Asn Gly Arg Gly Leu Asp Phe Gly Val
            115                 120                 125

Asn Val Leu Val Ser Gln Lys Pro Glu Pro Asp Asp Val Val Tyr Lys
        130                 135                 140

Gln Tyr Glu Ser Tyr Thr Val Thr Ile Thr Cys Pro Phe Thr Tyr Ala
145                 150                 155                 160

Thr Arg Gln Leu Lys Lys Ser Phe Tyr Lys Val Glu Asp Gly Glu Leu
                165                 170                 175

Val Leu Ile Ile Asp Ser Ser Lys Glu Ala Lys Asp Pro Arg Tyr
            180                 185                 190

Lys Gly Arg Ile Thr Leu Gln Ile Gln Ser Thr Thr Ala Lys Glu Phe
            195                 200                 205

Thr Val Thr Ile Lys His Leu Gln Leu Asn Asp Ala Gly Gln Tyr Val
        210                 215                 220

Cys Gln Ser Gly Ser Asp Pro Thr Ala Glu Glu Gln Asn Val Asp Leu
225                 230                 235                 240

Arg Leu Leu Thr Pro Gly Leu Tyr Gly Asn Leu Gly Gly Ser Val
                245                 250                 255

Thr Phe Glu Cys Ala Leu Asp Ser Glu Asp Ala Asn Ala Val Ala Ser
            260                 265                 270

Leu Arg Gln Val Arg Gly Gly Asn Val Val Ile Asp Ser Gln Gly Thr
        275                 280                 285
```

-continued

```
Ile Asp Pro Ala Phe Glu Gly Arg Ile Leu Phe Thr Lys Ala Glu Asn
290                 295                 300
Gly His Phe Ser Val Val Ile Ala Gly Leu Arg Lys Glu Asp Thr Gly
305                 310                 315                 320
Asn Tyr Leu Cys Gly Val Gln Ser Asn Gly Gln Ser Gly Asp Gly Pro
            325                 330                 335
Thr Gln Leu Arg Gln Leu Phe Val Asn Glu Glu Ile Asp Val Ser Arg
            340                 345                 350
Ser Pro Pro Val Leu Lys Gly Phe Pro Gly Gly Ser Val Thr Ile Arg
            355                 360                 365
Cys Pro Tyr Asn Pro Lys Arg Ser Asp Ser His Leu Gln Leu Tyr Leu
        370                 375                 380
Trp Glu Gly Ser Gln Thr Arg His Leu Leu Val Asp Ser Gly Glu Gly
385                 390                 395                 400
Leu Val Gln Lys Asp Tyr Thr Gly Arg Leu Ala Leu Phe Glu Glu Pro
                405                 410                 415
Gly Asn Gly Thr Phe Ser Val Val Leu Asn Gln Leu Thr Ala Glu Asp
            420                 425                 430
Glu Gly Phe Tyr Trp Cys Val Ser Asp Asp Glu Ser Leu Thr Thr
            435                 440                 445
Ser Val Lys Leu Gln Ile Val Asp Gly Glu Pro Ser Pro Thr Ile Asp
450                 455                 460
Lys Phe Thr Ala Val Gln Gly Glu Pro Val Glu Ile Thr Cys His Phe
465                 470                 475                 480
Pro Cys Lys Tyr Phe Ser Ser Glu Lys Tyr Trp Cys Lys Trp Asn Asp
                485                 490                 495
His Gly Cys Glu Asp Leu Pro Thr Lys Leu Ser Ser Ser Gly Asp Leu
            500                 505                 510
Val Lys Cys Asn Asn Asn Leu Val Leu Thr Leu Thr Leu Asp Ser Val
        515                 520                 525
Ser Glu Asp Asp Glu Gly Trp Tyr Trp Cys Gly Ala Lys Asp Gly His
530                 535                 540
Glu Phe Glu Glu Val Ala Ala Val Arg Val Glu Leu Thr Glu Pro Ala
545                 550                 555                 560
Lys Val Ala Val Glu Pro Ala Lys Val Pro Val Asp Pro Ala Lys Ala
                565                 570                 575
Ala Pro Ala Pro Ala Glu Glu Lys Ala Lys Ala Arg Cys Pro Val Pro
            580                 585                 590
Arg Arg Arg Gln Trp Tyr Pro Leu Ser Arg Lys Leu Arg Thr Ser Cys
            595                 600                 605
Pro Glu Pro Arg Leu Leu Ala Glu Val Ala Val Gln Ser Ala Glu
        610                 615                 620
Asp Pro Ala Ser Gly Ser Arg Ala Ser Val Asp Ala Ser Ser Ala Ser
625                 630                 635                 640
Gly Gln Ser Gly Ser Ala Lys Val Leu Ile Ser Thr Leu Val Pro Leu
            645                 650                 655
Gly Leu Val Leu Ala Ala Gly Ala Met Ala Val Ala Ile Ala Arg Ala
            660                 665                 670
Arg His Arg Arg Asn Val Asp Arg Val Ser Ile Gly Ser Tyr Arg Thr
        675                 680                 685
Asp Ile Ser Met Ser Asp Leu Glu Asn Ser Arg Glu Phe Gly Ala Ile
    690                 695                 700
Asp Asn Pro Ser Ala Cys Pro Asp Ala Arg Glu Thr Ala Leu Gly Gly
```

```
                705                 710                 715                 720
Lys Asp Glu Leu Ala Thr Ala Thr Glu Ser Thr Val Glu Ile Glu Glu
                    725                 730                 735
Pro Lys Lys Ala Lys Arg Ser Ser Lys Glu Glu Ala Asp Leu Ala Tyr
            740                 745                 750
Ser Ala Phe Leu Leu Gln Ser Asn Thr Ile Ala Ala Glu His Gln Asp
        755                 760                 765
Gly Pro Lys Glu Ala
    770

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence:
      extracellular residues of rabbit pIgR that precede
      membrane-spanning segment

<400> SEQUENCE: 7

Asp Pro Ala Ser Gly Ser Arg Ala Ser Val Asp Ala Ser Ser Ala Ser
 1               5                  10                  15

Gly Gln Ser Gly Ser Ala Lys
            20

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence:
      extracellular membrane proximal amino acids of rabbit pIgR with
      C-terminal Cys added for conjugation

<400> SEQUENCE: 8

Asp Pro Ala Ser Gly Ser Arg Ala Ser Val Asp Ala Ser Ser Ala Ser
 1               5                  10                  15
Gly Gln Ser Gly Ser Ala Lys Cys
            20

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence:
      extracellular membrane proximal amino acids of rabbit pIgR with
      C-terminal Cys added for conjugation

<400> SEQUENCE: 9

Ala Ser Val Asp Ala Ser Ser Ala Ser Gly Gln Ser Gly Ser Ala Lys
 1               5                  10                  15

Cys

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:human
      pIgRepitope for scFv and antibody 4A

<400> SEQUENCE: 10

Gln Asp Pro Arg Leu Phe
 1               5
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:rat
    pIgRepitope for scFv and antibody 4A and 5D

<400> SEQUENCE: 11

Leu Asp Pro Arg Leu Phe
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:human
    pIgRepitope for antibody 5D

<400> SEQUENCE: 12

Lys Ala Ile Gln Asp Pro Arg Leu Phe
 1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence:rat
    pIgRepitope for scFv 2E

<400> SEQUENCE: 13

Leu Asp Pro Arg Leu Phe Ala Asp Glu Arg Glu Ile
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:rat
    pIgRepitope for scFv 2H

<400> SEQUENCE: 14

Asp Glu Asn Lys Ala Asn Leu Asp Pro Arg Leu Phe
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:rat
    pIgRepitope for scFv 1F

<400> SEQUENCE: 15

Arg Leu Phe Ala Asp Glu Arg Glu Ile
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:rat pIgR
    epitoe for scFvs 5F, 10H, 1C, 7H and 6B -continued

```
<400> SEQUENCE: 16

Leu Asp Pro Arg Leu Phe Ala Asp Glu
1               5

<210> SEQ ID NO 17
<211> LENGTH: 90
<212> TYPE: PRT
<213> ORGANISM: Artificial Sequence
<220> FEATURE:
<223> OTHER INFORMATION: Description of Artificial Sequence:portion of
      human pIgR encompassing part of domain 5 and domain 6

<400> SEQUENCE: 17

Gly His Phe Tyr Gly Glu Thr Ala Ala Val Tyr Val Ala Val Glu Glu
1               5                   10                  15

Arg Lys Ala Ala Gly Ser Arg Asp Val Ser Leu Ala Lys Ala Asp Ala
            20                  25                  30

Ala Pro Asp Glu Lys Val Leu Asp Ser Gly Phe Arg Glu Ile Glu Asn
        35                  40                  45

Lys Ala Ile Gln Asp Pro Arg Leu Phe Ala Glu Glu Lys Ala Val Ala
    50                  55                  60

Asp Thr Arg Asp Gln Ala Asp Gly Ser Arg Ala Ser Val Asp Ser Gly
65                  70                  75                  80

Ser Ser Glu Glu Gln Gly Gly Ser Ser Arg
                85                  90

<210> SEQ ID NO 18
<211> LENGTH: 93
<212> TYPE: PRT
<213> ORGANISM: Artificial Sequence
<220> FEATURE:
<223> OTHER INFORMATION: Description of Artificial Sequence:portion of
      rat pIgR encompassing part of domain 5 and domain 6

<400> SEQUENCE: 18

Gly Gln Val Tyr Gly Glu Thr Thr Ala Ile Tyr Val Ala Val Glu Glu
1               5                   10                  15

Arg Thr Arg Gly Ser Pro His Ile Asn Pro Thr Asp Ala Asn Ala Arg
            20                  25                  30

Ala Lys Asp Ala Pro Glu Glu Glu Ala Met Glu Ser Ser Val Arg Glu
        35                  40                  45

Asp Glu Asn Lys Ala Asn Leu Asp Pro Arg Leu Phe Ala Asp Glu Arg
    50                  55                  60

Glu Ile Gln Asn Ala Gly Asp Gln Ala Gln Glu Asn Arg Ala Ser Gly
65                  70                  75                  80

Asn Ala Gly Ser Ala Gly Gly Gln Ser Gly Ser Ser Lys
                85                  90

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence:human pIgR
      stalk

<400> SEQUENCE: 19

Glu Lys Ala Val Ala Asp Thr Arg Asp Gln Ala Asp Gly Ser Arg Ala
1               5                   10                  15

Ser Val Asp Ser Gly Ser Ser Glu Glu Gln Gly Gly Ser Ser Arg
```

-continued

```
                     20                  25                  30

<210> SEQ ID NO 20
<211> LENGTH: 95
<212> TYPE: PRT
<213> ORGANISM: Artificial Sequence
<220> FEATURE:
<223> OTHER INFORMATION: Description of Artificial Sequence:portion of
      human pIgR

<400> SEQUENCE: 20

Cys Gly Val Lys Gln Gly His Phe Tyr Gly Glu Thr Ala Ala Val Tyr
  1               5                  10                  15

Val Ala Val Glu Glu Arg Lys Ala Ala Gly Ser Arg Asp Val Ser Leu
                 20                  25                  30

Ala Lys Ala Asp Ala Ala Pro Asp Glu Lys Val Leu Asp Ser Gly Phe
             35                  40                  45

Arg Glu Ile Glu Asn Lys Ala Ile Gln Asp Pro Arg Leu Phe Ala Glu
         50                  55                  60

Glu Lys Ala Val Ala Asp Thr Arg Asp Gln Ala Asp Gly Ser Arg Ala
     65                  70                  75                  80

Ser Val Asp Ser Gly Ser Ser Glu Glu Gln Gly Ser Ser Arg
                 85                  90                  95

<210> SEQ ID NO 21
<211> LENGTH: 98
<212> TYPE: PRT
<213> ORGANISM: Artificial Sequence
<220> FEATURE:
<223> OTHER INFORMATION: Description of Artificial Sequence:portion of
      rat pIgR

<400> SEQUENCE: 21

Cys Gly Val Lys Glu Gly Gln Val Tyr Gly Glu Thr Thr Ala Ile Tyr
  1               5                  10                  15

Val Ala Val Glu Glu Arg Thr Arg Gly Ser Pro His Ile Asn Pro Thr
                 20                  25                  30

Asp Ala Asn Ala Arg Ala Lys Asp Ala Pro Glu Glu Gly Ala Met Glu
             35                  40                  45

Ser Ser Val Arg Glu Asp Glu Asn Lys Ala Asn Leu Asp Pro Arg Leu
         50                  55                  60

Phe Ala Asp Glu Arg Glu Ile Gln Asn Ala Gly Asp Gln Ala Gln Glu
     65                  70                  75                  80

Asn Arg Ala Ser Gly Asn Ala Gly Ser Ala Gly Gly Gln Ser Gly Ser
                 85                  90                  95

Ser Lys

<210> SEQ ID NO 22
<211> LENGTH: 288
<212> TYPE: PRT
<213> ORGANISM: Artificial Sequence
<220> FEATURE:
<223> OTHER INFORMATION: Description of Artificial
      Sequence:Pelb/4AF/myc/6HIS

<400> SEQUENCE: 22

Met Lys Tyr Leu Leu Pro Thr Ala Ala Ala Gly Leu Leu Leu Leu Ala
  1               5                  10                  15

Ala Gln Pro Ala Met Ala Gln Val Gln Leu Val Gln Ser Gly Gly Gly
                 20                  25                  30
```

-continued

```
Leu Val Gln Pro Gly Gly Ser Leu Arg Leu Ser Cys Ala Ala Ser Gly
         35                  40                  45

Phe Thr Phe Ser Ser Tyr Ala Met Ser Trp Val Arg Gln Ala Pro Gly
     50                  55                  60

Lys Gly Leu Glu Trp Val Ser Ala Ile Ser Gly Ser Gly Gly Ser Thr
 65                  70                  75                  80

Tyr Tyr Ala Asp Ser Val Lys Gly Arg Phe Thr Ile Ser Arg Asp Asn
                 85                  90                  95

Ser Lys Asn Thr Leu Tyr Leu Gln Met Asn Ser Leu Arg Ala Glu Asp
             100                 105                 110

Thr Ala Val Tyr Tyr Cys Ala Arg Ser Phe Thr Val Asn Ser Gly Tyr
         115                 120                 125

Phe Gln His Trp Gly Gln Gly Thr Leu Val Thr Val Ser Ser Gly Gly
     130                 135                 140

Gly Gly Ser Gly Gly Gly Gly Ser Gly Gly Gly Gly Ser Glu Ile Val
145                 150                 155                 160

Leu Thr Gln Ser Pro Ser Thr Leu Ser Ala Ser Ile Gly Asp Arg Val
                 165                 170                 175

Thr Ile Thr Cys Arg Ala Ser Glu Gly Ile Tyr His Trp Leu Ala Trp
             180                 185                 190

Tyr Gln Gln Lys Pro Gly Lys Ala Pro Lys Leu Leu Ile Tyr Lys Ala
         195                 200                 205

Ser Ser Leu Ala Ser Gly Val Pro Ser Arg Phe Ser Gly Ser Gly Ser
     210                 215                 220

Gly Thr Asp Phe Thr Leu Thr Ile Ser Ser Leu Gln Pro Glu Asp Phe
225                 230                 235                 240

Ala Thr Tyr Tyr Cys Gln His Tyr Asp Ser Thr Pro Pro Thr Phe Gly
                 245                 250                 255

Gln Gly Thr Lys Val Asp Ile Lys Arg Ala Ala Ala Glu Gln Lys Leu
             260                 265                 270

Ile Ser Glu Glu Asp Leu Asn Gly Ala Ala His His His His His His
         275                 280                 285
```

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 23

Gly Gly Gly Ser
 1

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:peptide
      linker

<400> SEQUENCE: 24

Gly Gly Gly Ser Gly Gly Gly
 1               5

<210> SEQ ID NO 25
<211> LENGTH: 5

```
<212> TYPE: PRT
<213> ORGANISM: Artificial Sequence
<220> FEATURE:
<223> OTHER INFORMATION: Description of Artificial Sequence:peptide
      linker

<400> SEQUENCE: 25

Gly Gly Gly Gly Ser
  1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:scFv 4A
      epitope

<400> SEQUENCE: 26

Asp Pro Arg Leu Phe
  1               5
```